(12) United States Patent
Andersson et al.

(10) Patent No.: US 7,285,385 B2
(45) Date of Patent: Oct. 23, 2007

(54) METHODS FOR ANALYZING ANIMAL PRODUCTS

(75) Inventors: Leif Andersson, Uppsala (SE); James Kijas, Ithaca, NY (US); Elisabetta Giuffra, Uppsala (SE); Gary Jon Evans, Cambridge (GB); Richard Wales, Cambridge (GB); Graham Stuart Plastow, Cambridge (GB)

(73) Assignee: Pig Improvement Company UK Limited, Oxfordshire (GB)

( * ) Notice: Subject to any disclaimer, the term of this patent is extended or adjusted under 35 U.S.C. 154(b) by 345 days.

(21) Appl. No.: 10/758,422

(22) Filed: Jan. 16, 2004

(65) Prior Publication Data

US 2005/0059123 A1 Mar. 17, 2005

Related U.S. Application Data

(63) Continuation of application No. 09/450,651, filed on Nov. 30, 1999, now abandoned, which is a continuation of application No. PCT/GB98/01531, filed on May 27, 1998.

(30) Foreign Application Priority Data

May 30, 1997 (GB) .................................. 9711214.8
Jan. 31, 1998 (GB) .................................. 9801990.4

(51) Int. Cl.
*C12Q 1/68* (2006.01)
*C12Q 1/44* (2006.01)
*C07H 21/02* (2006.01)

(52) U.S. Cl. .............................. 435/6; 536/23.1; 435/4; 435/18; 435/19

(58) Field of Classification Search ..................... None
See application file for complete search history.

(56) References Cited

FOREIGN PATENT DOCUMENTS

| WO | WO94/04674 | 3/1994 |
| WO | WO96/34982 | 11/1996 |
| WO | WO97/05278 | 2/1997 |

OTHER PUBLICATIONS

McPherron et al. Regulation of skeletal muscle mass in mice by a new TGF-beta superfamily member. May 1, 1997. Nature, vol. 387, pp. 83-90.*

Mariani et al. The extension coat color locus and the loci for blood group O and tyrosine aminotransferase are on pig chromosome 6. Journal of Heredity (1996) vol. 87, pp. 272-276.*

Adalsteinsson et al. Inhertiance of the palomino color in Icelandic horses. J Hered. Jan.-Feb. 1974;65(1):15-20.

Adalsteinsson et al. Fox colors in relation to colors in mice and sheep. J Hered. Jul.-Aug. 1987;78(4):235-7.

Georges and Andersson Livestock genomics comes of age. Genome Res. Oct. 1996;6(10):907-21.

Grobet et al. A deletion in the bovine myostatin gene causes the double-muscled phenotype in cattle. Nat. Genet. Sep. 1997;17(1):71-4.

Joerg et al. Red coat color in Holstein cattle is associated with a deletion in the MSHR gene. Mamm Genome. Apr. 1996;7(4):317-8.

Kambadur et al. Mutations in myostatin (GDF8) in double-muscled Belgian Blue and Piedmontese cattle. Genome Res. Sep. 1997;7(9):910-6.

Klungland et al. The role of melanocyte-stimulating hormone (MSH) receptor in bovine coat color determination. Mamm Genome. Sep. 1995;6(9):636-9.

Legault (1997) The Genetics of the Pig, Ed. Rothschild M.F. and Ruvinsky A, Publ. CAB International.

Marklund et al. (Dec. 1996) A missense mutation in the gene for melanocyte-stimulating hormone receptor (MC1R) is associated with the chestnut coat color in horses. Mamm Genome. 7(12):895-9.

Moller et al. (Nov. 1996) Pigs with the dominant white coat color phenotype carry a duplication of the KIT gene encoding the mast/stem cell growth factor receptor 7(11): 822-830.

Ollivier & Sellier (1982) *Ann. Génét. Sél. Anim. 14*: 481-544.

Porter "PIGS A Handbook to breeds of the world." Helm Inf. Ltd, ISBN 1-873403-17-8 (1993) p. 16 "What is a Breed?".

Robbins et al. (Mar. 26, 1993) Pigmentation phenotypes of variant extension locus alleles result from point mutations that alter MSH receptor function Cell 72(6): 827-834.

Valverde et al. (Nov. 1995) Variants of the melanocyte-stimulating hormone receptor gene are associated with red hair and fair skin in humans Nature Genetics 11(3): 328-330.

Vanetti et al. FEBS Lett. 348 268-272 (1994).

* cited by examiner

*Primary Examiner*—Gary Benzion
*Assistant Examiner*—Samuel Woolwine
(74) *Attorney, Agent, or Firm*—Hunton & Williams LLP

(57) ABSTRACT

The present invention provides methods for analysing animal products. In particular methods for differentiating animal products on the basis of breed origin or validating an animal product are provided.

2 Claims, 17 Drawing Sheets

FIG. 1 a: Nucleotide sequence

```
                                                              1                                                   27
Wild Boar    CTCCCTGCTCCCTGCTCCCTGGCGGGACG ATG CCT GTG CTT GGC CCG GAG AGG AGG
Meishan      ............................. ... ... ... ... ... ... ... ...
Pietrain     ............................. ... ... ... ... ... ... ... ...

75
Wild Boar    CTG CTG GCT TCC CTC AGC TCC GCG CCC CCA GCC GCC CCC ** CGG CCG CCA
Meishan      ... ... ... ... ... ... ... ... ... ... ... ... ... ** ... ... ...
Pietrain     ... ... ... ... ... ... ... ... ... ... ... ... ... CC ... ... ...

126
Wild Boar    ACG CCT CGG GCT CAG ACC AAC CAG ACG GGC CCC CAG TGC CTG GAG GTG TCC
Meishan      ... ... ... ... ... ... ... ... ... ... ... ... ... ... ... ... ...
Pietrain     ... ... ... ... ... ... ... ... ... ... ... ... ... ... ... ... ...

177
Wildboar     ATT CCC GAC GGG CTC TTC CTC AGC CTG GGG CTG GTG AGC CTC GTG GAG AAC
Meishan      ... ... ... ... ... ... ... ... ... ... ... ... ... ... ... ... ...
Pietrain     ... ... ... ... ... ... ... ... ... ... ... ... ... ... ... ... ...
Largewhite   ... ... ... ... ... ... ... ... ... ... ... ... ... ... ... ... ...
Hampshire    ... ... ... ... ... ... ... ... ... ... ... ... ... ... ... ... ...
Duroc        ... ... ... ... ... ... ... ... ... ... ... ... ... ... ... ... ...

228
Wildboar     GTG CTG GTG GTG GCC GCC ATC GCC AAG AAC CGC AAC CTG CAC TCG CCC ATG
Meishan      ... ... ... ... ... ... ... ... ... ... ... ... ... ... ... ... ...
Pietrain     ... ... ... ... ... ... ... ... ... ... ... ... ... ... ... ... ...
Largewhite   ... ... ... ... ... ... ... ... ... ... ... ... ... ... ... ... ...
Hampshire    ... ... ... ... ... ... ... ... ... ... ... ... ... ... ... ... ...
Duroc        ... ... ... ... ... ... ... ... ... ... ... ... ... ... ... ... ...

279
Wildboar     TAC TAC TTC GTC TGC TGC CTG GCC GTG TCG GAC CTG CTG GTG AGC GTG AGC
Meishan      ... ... ... ... ... ... ... ... ... ... ... ... ... ... ... ... ...
Pietrain     ... ... ... ... ... ... ... ... ... ... ... ... ... ... ... ... ...
Largewhite   ... ... ... ... ... ... ... ... ... ... ... ... ... ... ... ... ...
Hampshire    ... ... ... ... ... ... ... ... ... ... ... ... ... ... ... ... ...
Duroc        ... ... ... ... ... ... ... ... ... ... ... ... ... ... ... ... ...

330
Wildboar     AAC GTG CTG GAG ACG GCC GTG CTG CTG CTG CTG GAG GCG GGC GCC CTG GCC
Meishan      ... A.. ... ... ... ... ... ... .C. ... ... ... ... ... ... ... ...
Pietrain     ... ... ... ... ... ... ... ... ... ... ... ... ... ... ... ... ...
Largewhite   ... ... ... ... ... ... ... ... ... ... ... ... ... ... ... ... ...
Hampshire    ... ... ... ... ... ... ... ... ... ... ... ... ... ... ... ... ...
Duroc        ... ... ... ... ... ... ... ... ... ... ... ... ... ... ... ... ...

381
Wildboar     GCC CAG GCC GCC GTG GTG CAG CAG CTG GAC AAT GTC ATG GAC GTG CTC ATC
Meishan      ... ... ... ... ... ... ... ... ... ..C ... ... ... ... ... ... ...
Pietrain     ... ... ... ... ... ... ... ... ... ... ... ... A.. ... ... ... ...
Largewhite   ... ... ... ... ... ... ... ... ... ... ... ... A.. ... ... ... ...
Hampshire    ... ... ... ... ... ... ... ... ... ... ... ... A.. ... ... ... ...
Duroc        ... ... ... ... ... ... ... ... ... ... ... ... ... ... ... ... ...
```

```
                                                                                          432
Wildboar    TGC GGC TCC ATG GTG TCC AGC CTC TGC TTC CTG GGC GCC ATC GCC GTG GAC
Meishan     ... ... ... ... ... ... ... ... ... ... ... ... ... ... ... ... ...
Pietrain    ... ... ... ... ... ... ... ... ... ... ... ... ... ... ... ... ...
Largewhite  ... ... ... ... ... ... ... ... ... ... ... ... ... ... ... ... ...
Hampshire   ... ... ... ... ... ... ... ... ... ... ... ... ... ... ... ... ...
Duroc       ... ... ... ... ... ... ... ... ... ... ... ... ... ... ... ... ...

483
Wildboar    CGC TAC GTG TCC ATC TTC TAC GCG CTG CGC TAC CAC AGC ATC GTG ACG CTG
Meishan     ... ... ... ... ... ... ... ... ... ... ... ... ... ... ... ... ...
Pietrain    ... ... ... ... ... ... ... ... ... ... ... ... ... ... ... ... ...
Largewhite  ... ... ... ... ... ... ... ... ... ... ... ... ... ... ... ... ...
Hampshire   ... ... ... ... ... ... ... ... ... ... ... ... ... ... ... ... ...
Duroc       ... ... ... ... ... ... ... ... ... ... ... ... ... ... ... ... ...

534
Wildboar    CCC CGC GCG GGG CGG GCT ATC GCG GCG ATC TGG GCG GGC AGC GTG CTC TCC
Meishan     ... ... ... ... ... ... ... ... ... ... ... ... ... ... ... ... ...
Pietrain    ... ... ... ... ... ... ... ... ... ... ... ... ... ... ... ... ...
Largewhite  ... ... ... ... ... ... ... ... ... ... ... ... ... ... ... ... ...
Hampshire   ... ... ... ... ... ... ... ... ... ... ... ... ... ... ... ... ...
Duroc       ... ... .T. ... ... ... ... ... ... ... ... ... ... ... ... ... ...

585
Wildboar    AGC ACC CTC TTC ATC GCC TAC TAC CAC CAC ACG GCC GTC CTG CTG GGC CTC
Meishan     ... ... ... ... ... ... ... ... ... ... ... ... ... ... ... ... ...
Pietrain    ... ... ... ... ... ... ... ... ... ... ... ... ... ... ... ... ...
Largewhite  ... ... ... ... ... ... ... ... ... ... ... ... ... ... ... ... ...
Hampshire   ... ... ... ... ... ... ... ... ... ... ... ... ... ... ... ... ...
Duroc       ... ... ... ... ... ... ... ... ... ... ... ... ... ... ... ... ...

636
Wildboar    GTC AGC TTC TTC GTG GCC ATG CTG GCG CTC ATG GCG GTA CTG TAC GTC CAC
Meishan     ... ... ... ... ... ... ... ... ... ... ... ... ... ... ... ... ...
Pietrain    ... ... ... ... ... ... ... ... ... ... ... ... ... ... ... ... ...
Largewhite  ... ... ... ... ... ... ... ... ... ... ... ... ... ... ... ... ...
Hampshire   ... ... ... ... ... ... ... ... ... ... ... ... ... ... ... ... ...
Duroc       ... ... ... ... ... ... ... ... ... ... ... ... ... ... ... ... ...

687
Wildboar    ATG CTG GCC CGG GCC TGC CAG CAC GGC CGG CAC ATC GCC CGG CTC CAC AAG
Meishan     ... ... ... ... ... ... ... ... ... ... ... ... ... ... ... ... ...
Pietrain    ... ... ... ... ... ... ... ... ... ... ... ... ... ... ... ... ...
Largewhite  ... ... ... ... ... ... ... ... ... ... ... ... ... ... ... ... ...
Hampshire   ... ... ... ... ... ... ... ... ... ... ... ... ... ... ... ... ...
Duroc       ... ... ... ... ... ... ... ... ... ... ... ... ... ... ... ... ...

738
Wildboar    ACG CAG CAC CCC ACC CGC CAG GGC TGC GGC CTC AAG GGC GCG GCC ACC CTC
Meishan     ... ... ... ... ... ... ... ... ... ... ... ... ..A ... ... ... ...
Pietrain    ... ... ... ... ... ... ... ... ... ... ... ... ... ... ... ... ...
Largewhite  ... ... ... ... ... ... ... ... ... ... ... ... ... ... ... ... ...
Hampshire   ... ... ... ... ... ... ... ... ... ... ... ... ... ... ... ... ...
Duroc       ... ... ... ... ... ... ... ... ... ... ... ... ... A.. ... ... ...
```

FIG. 1 CONT'D

```
                                                                              789
Wildboar    ACC ATC CTG CTG GGC GTC TTC CTC CTC TGC TGG GCA CCC TTC TTC CTG CAC
Meishan     ... ... ... ... ... ... ... ... ... ... ... ... ... ... ... ... ...
Pietrain    ... ... ... ... ... ... ... ... ... ... ... ... ... ... ... ... ...
Largewhite  ... ... ... ... ... ... ... ... ... ... ... ... ... ... ... ... ...
Hampshire   ... ... ... ... ... ... ... ... ... ... ... ... ... ... ... ... ...
Duroc       ... ... ... ... ... ... ... ... ... ... ... ... ... ... ... ... ...

840
Wildboar    CTC TCC CTC GTC GTC CTC TGC CCC CAG CAC CCC ACC TGC GGC TGC GTC TTC
Meishan     ... ... ... ... ... ... ... ... ... ... ... ... ... ... ... ... ...
Pietrain    ... ... ... ... ... ... ... ... ... ... ... ... ... ... ... ... ...
Largewhite  ... ... ... ... ... ... ... ... ... ... ... ... ... ... ... ... ...
Hampshire   ... ... ... ... ... ... ... ... ... ... ... ... ... ... ... ... ...
Duroc       ... ... ... ... ... ... ... ... ... ... ... ... ... ... ... ... ...

885
Wildboar    AAG AAC GTC AAC CTC TTT CTG GCC CTC GTC ATC TGC AAC TCC ATC
Meishan     ... ... ... ... ... ... ... ... ... ... ... ... ... ... ...
Pietrain    ... ... ... ... ... ... ... ... ... ... ... ... ... ... ...
Largewhite  ... ... ... ... ... ... ... ... ... ... ... ... ... ... ...
Hampshire   ... ... ... ... ... ... ... ... ... ... ... ... ... ... ...
Duroc       ... ... ... ... ... ... ... ... ... ... ... ... ... ... ...
``` b. Amino acid sequence

```
                                                                                 99
Wildboar    ?PNGLFLSLG LVSLVENVLV VAAIAKNRNL HSPMYYFVCC LAVSDLLVSV SNVLETAVLL
Meishan     .......... .......... .......... .......... .......... ..M......P
Largewhite  .......... .......... .......... .......... .......... ..........
Hampshire   .......... .......... .......... .......... .......... ..........
Duroc       .......... .......... .......... .......... .......... ..........

159
Wildboar    LLEAGALAAQ AAVVQQLDNV MDVLICGSMV SSLCFLGAIA VDRYVSIFYA LRYHSIVTLP
Meishan     .......... .......... .......... .......... .......... ..........
Largewhite  .......... .......... .N........ .......... .......... ..........
Hampshire   .......... .......... .N........ .......... .......... ..........
Duroc       .......... .......... .......... .......... .......... ..........

219
Wildboar    RAGRAIAAIW AGSVLSSTLF IAYYHHTAVL LGLVSFFVAM LALMAVLYVH MLARACQHGR
Meishan     .......... .......... .......... .......... .......... ..........
Largewhite  .......... .......... .......... .......... .......... ..........
Hampshire   .......... .......... .......... .......... .......... ..........
Duroc       .V........ .......... .......... .......... .......... ..........

279
Wildboar    HIARLHKTQH PTRQGCGLKG AATLTILLGV FLLCWAPFFL HLSLVVLCPQ HPTCGCVFKN
Meishan     .......... .......... .......... .......... .......... ..........
Largewhite  .......... .......... .......... .......... .......... ..........
Hampshire   .......... .......... .......... .......... .......... ..........
Duroc       .......... .......... T......... .......... .......... ..........

Wildboar    VNLFLALVIC NSI
Meishan     .......... ...
Largewhite  .......... ...
Hampshir    .......... ...
Duroc       .......... ...
```

FIG. 1 CON'T

Sequence Alignment Across the Exon /Intron Border of KIT Exon 17

```
Allele  Gene Copy           Sequence
                    Exon 17    Intron 17
                                      |↓
  I       KIT1    AAT TAC GTG GTC AAA GGA AAC|GTG AGT ACC CAC GCT CTC CTG ACA GTC
          KIT2    ... ... ... ... ... ... ...|A.. ... ... ... ... ... ... ... ...

Iᴾ      KIT1    ... ... ... ... ... ... ...|G... ... ... ... ... ... ... ... ...
          KIT1    ... ... ... ... ... ... ...|G.. ... ... ... ... ... ... ... ...

i       KIT1    ... ... ... ... ... ... ...|G.. ... ... ... ... ... ... ... ...
```

FIG. 5

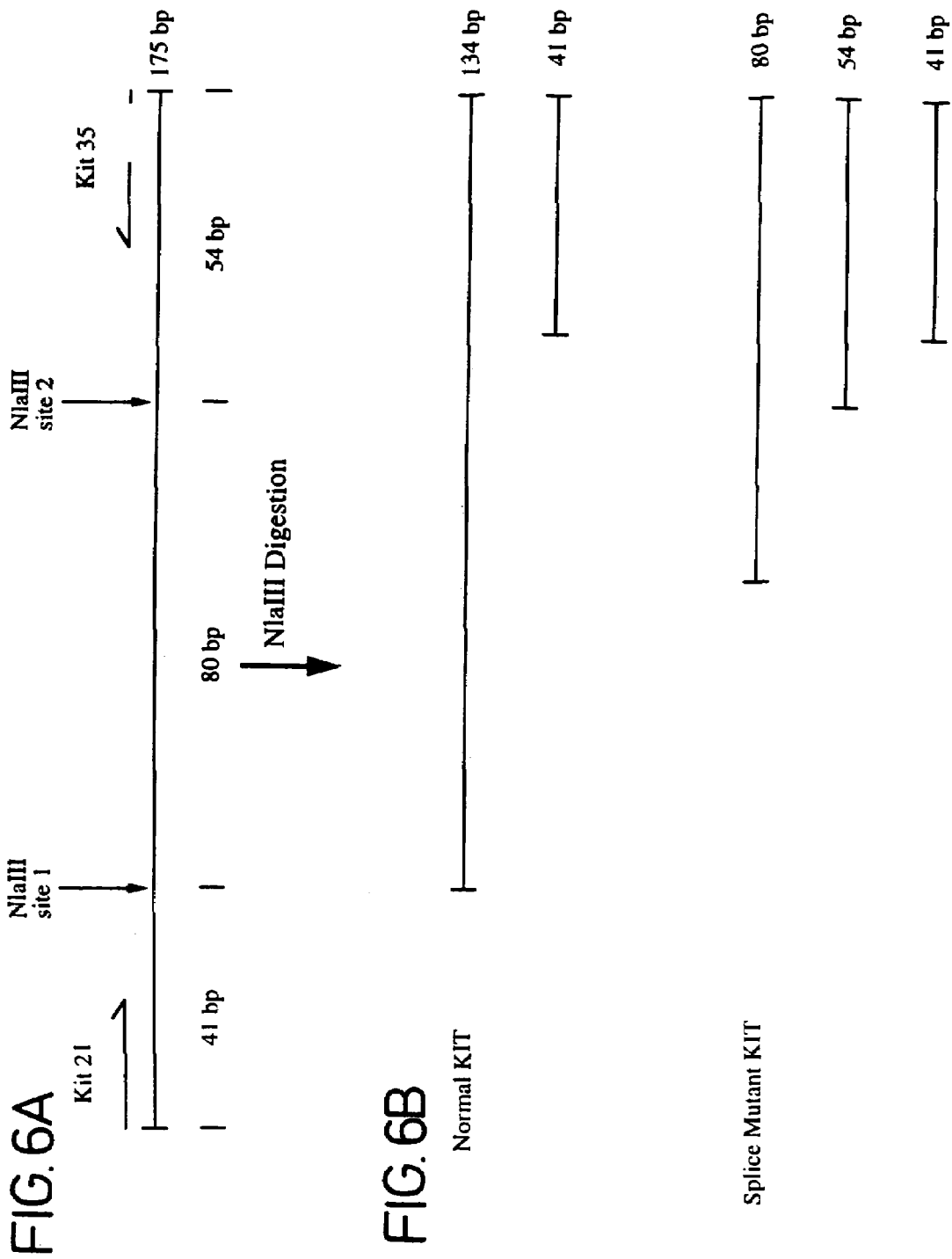

```
1
ATG AGA GGC GCT CGC CGC GCC TGG GAT TTT CTC TTC GTC CTG CAG CTC TTG
52
CTT CGC GTC CAG ACA GGC TCT TCT CAG CCA TCT GTG AGT CCA GAG GAA CTG
103
TCT CCA CCA TCC ATC CAT CCA GCA AAA TCA GAG TTA ATC GTC AGT GCT GGC
154
GAT GAG ATT AGG CTG TTC TGC ACC GAT CCA GGA TCT GTC AAA TGG ACT TTT
205
GAG ACC CTG GGT CAG CTG AGT GAG AAT ACA CAC GCA GAG TGG ATC GTG GAG
256
AAA GCA GAG GCC ATG AAT ACA GGC AAT TAT ACA TGC ACC AAT GAA GGC GGT
307
TTA AGC AGT TCC ATT TAT GTG TTT GTT AGA GAT CCT GAG AAG CTT TTC CTC
358
GTC GAC CCT CCC TTG TAT GGG AAG GAG GAC AAT GAC GCG CTG GTC CGA TGT
409
CCT CTG ACG GAC CCA GAG GTG ACC AAT TAC TCC CTC ACG GGC TGC GAG GGG
460
AAA CCC CTT CCC AAG GAT TTG ACC TTC GTC GCG GAC CCC AAG GCC GGC ATC
511
ACC ATC AGA AAC GTG AAG CGC GAG TAT CAT CGG CTC TGT CTC CAC TGC TCC
562
GCC AAC CAG GGG GGC AAG TCC GTG CTG TCG AAG AAA TTC ACC CTG AAA GTG
613
AGG GCA GCC ATC AGA GCT GTA CCT GTT GTG GCT GTG TCC AAA GCA AGC TAC
664
CTT CTC AGG GAA GGG GAG GAA TTT GCC GTG ATG TGC TTG ATC AAA GAC GTG
715
TCT AGT CCG TGA CTC CAT GTG GAT CAG GAG AAC AGC CAG ACT AAA GCA
766
CAG GTG AAG AGG AAT AGC TGG CAT CAG GGT GAC TTC AAT TTT CTG CGG CAG
817
GAA AGG CTG ACA ATC AGC TCA GCA AGA GTT AAT GAT CTG GCG TG TTC ATG
868
TGT TAC GCC AAT AAT ACT TTT GGA TCT GCA AAT GTC ACA ACC ACC TTA GAA
919
GTA GTA GAT AAA GGA TTC ATT AAT ATC TTC CCT ATG ATG AAT ACC ACT GTG
970
TTT GTA AAC GAT GGA GAG GAT GTG GAT CTA ATT GTT GAG TAC GAG GCG TAC
1021
CCC AAA CCT GAA CAC CGA CAG TGG ATA TAT ATG AAC CGC ACT GCC ACT GAT
1072
AAG TGG GAG GAT TAT CCC AAG TCT GAG AAT GAA AGT AAC ATC AGA TAT GTA
1123
AGT GAA CTT CAC TTG ACC AGA TTA AAA GGG ACC GAA GGA GGC ACT TAC ACA
1174
TTT CTC GTG TCC AAT GCT GAT GTC AAT TCT CTG TGA CAT TTA ATG TTA C
1225
GTG AAC ACA AAA CCA GAA ATC CTG ACT CAT GAC AGG CTC ATG AAC GGC ATG
1276
CTC CAG TGT GTG GCG GCA GGC TTC CCA GAG CCC ACC ATC GAT TGG TAT TTC
1327
TGT CCA GGC ACC GAG CAG AGA TGT TCC GTT CCC GTT GGG CCA GTG GAC GTG
1378
CAG ATC CAA AAC TCA TCT GTA TCA CCG TTT GGA AAA CTA GTG ATT CAC AGC
1429
```

FIG. 10

```
TCC ATT GAT TAC AGT GCA TTC AAA CAC AAC GGC ACG GTG GAG TGC AGG GCT
1480
TAC AAC GAT GTG GGC AAG AGT TCT GCC TTT TTT AAC TTT GCA TTT AAA GAA
1531
CAA ATC CAT GCC CAC ACC CTC TTC ACG CCT TTG CTG ATT GGT TTT GTG ATC
1582
GCA GCG GGT ATG ATG TGT ATC ATC GTG ATG ATT CTC ACC TAT AAA TAT CTA
1633
CAG AAG CCC ATG TAT GAA GTA CAG TGG AAG GTT GTC GAG GAG ATA AAT GGA
1684
AAC AAT TAT GTC TAC ATA GAC CCA ACG CAA CTT CCT TAT GAT CAC AAA TGG
1735
GAA TTT CCC AGG AAC AGG CTG AGT TTT GGC AAA ACC TTG GGT GCT GGC GCC
1786
TTC GGG AAA GTC GTT GAG GCC ACT GCA TAC GGC TTA ATT AAG TCA GAT GCG
1837
GCC ATG ACC GTT GCC GTG AAG ATG CTC AAA CCA AGT GCC CAT TTA ACG GAA
1888
CGA GAA GCC CTA ATG TCT GAA CTC AAA GTC TTA AGT TAC CTC GGT AAT CAC
1939
ATG AAT ATT GTG AAT CTT CTC GGC GCC TGC ACC ATT GGA GGG CCC ACC CTG
1990
GTC ATT ACA GAA TAT TGT TGC TAT GGT GAT CTC CTG AAT TTT TTG AGA CGG
2041
AAA CGT GAT TCG TTT ATT TGC TCA AAG CAG GAA GAT CAC GCA GAA GCG GCG
2092
CTT TAT AAG AAC CTT CTG CAT TCA AAG GAG TCT TCC TGC AGT GAC AGT ACT
2143
AAC GAG TAC ATG GAC ATG AAA CCC GGA GTG TCT TAT GTG GTA CCA ACC AAG
2194
GCA GAC AAA AGG AGA TCT GCG AGA ATA GGC TCA TAC ATA GAA CGA GAT GTG
2245
ACT CCT GCC ATC ATG GAA GAT GAT GAG TTG GCC CTA GAC CTG GAG GAC TTG
2296
CTC AGC TTT TCT TAC CAA GTG GCA AAG GGC ATG GCC TTC CTC GCC TCG AAG
2347
AAT TGT ATT CAC AGA GAC TTG GCG GCC AGA AAT ATC CTC CTT ACT CAT GGT
2398
CGA ATC ACA AAG ATT TGT GAT TTT GGT CTA GCC AGA GAC ATC AAG AAT GAT
2449
TCT AAT TAC GTG GTC AAA GGA AAC GCT CGG CTA CCC GTG AAG TGG ATG GCA
2500
CCT GAG AGC ATT TTC AAC TGT GTC TAC ACA TTT GAA AGC GAT GTC TGG TCC
2551
TAT GGG ATT TTT CTG TGG GAG CTC TTC TCT TTA GGG AGC AGC CCC TAC CCC
2602
GGA ATG CCA GTT GAT TCT AAA TTC TAC AAG ATG ATC AAG GAG GGT TTC CGA
2653
ATG CTC AGC CCT GAG CAT GCA CCT GCG GAA ATG TAT GAC ATC ATG AAG ACT
2704
TGC TGG GAT GCG GAT CCC CTC AAA AGA CCA ACG TTT AAG CAG ATC GTG CAG
2755
CTG ATT GAG AAG CAG ATT TCG GAG AGC ACC AAT CAC ATT TAT TCC AAC TTA
2806
GCG AAC TGC AGC CCC CAC CGG GAG AAC CCC GCG GTG GAT CAT TCT GTG CGG
2857
ATC AAC TCC GTG GGC AGC AGT GCC TCC TCC ACG CAG CCT CTG CTT GTC CAC
2908
GAA GAT GTC TGA
```

FIG. 10 CONT'D

```
                                                                             1012
Wild Boar                           CTGCAGTGCT CCTGGTGAGG GGGGACGGGC
Meishan                             ---------- ---------- ----------
Large Black                         ---------- ---------- ----------
Hampshire                           ---------- ---------- ----------
Pietrain                            ---------- ---------- ----------
Duroc                               ---------- ---------- ----------

1062
Wild Boar    GCTGGAGCCA GGCTGCGGGG CTGAGGGCAG TGGTGCCGTC CTGCGGCCCG
Meishan      ---------- ---------- ---------- ---------- ----------
Large Black  ---------- ---------- ---------- ---------- ----------
Hampshire    ---------- ---------- ---------- ---------- ----------
Pietrain     ---------- ---------- ---------- ---------- ----------
Duroc        ---------- ---------- ---------- ---------- ----------

1112
Wild Boar    GTTCCTACGT GGCTGGGCAG CCCCTTGGCA GAGAGGACGG GCCGGACATC
Meishan      ---------- ---------- ---------- ---------- ----------
Large Black  ---------- ---------- ---------- ---------- ----------
Hampshire    ---------- ---------- ---------- ---------- ----------
Pietrain     ---------- ---------- ---------- ---------- ----------
Duroc        ---------- ---------- ---------- ---------- ----------

1162
Wild Boar    TCTGAAGGTA TGGACGCTGG ACCCTCTGGG GCCCGACAGA GGAAGAGCCA
Meishan      ---------- ---------- ---------- ---------- ---------G
Large Black  ---------- ---------- ---------- ---------- ---------G
Hampshire    ---------- ---------- ---------- ---------- ---------G
Pietrain     ---------- ---------- ---------- ---------- ---------G
Duroc        ---------- ---------- ---------- ---------- ---------G 1212
Wild Boar    GCACTTCCAG GAGGCATGGG GAGTGGGGGA GGCTGGAGAG ACGGCGGGGA
Meishan      ---------- ---------- ---------- ---------- ----------
Large Black  ---------- ---------- ---------- ---------- ----------
Hampshire    ---------- ---------- ---------- ---------- ----------
Pietrain     ---------- ---------- ---------- ---------- ----------
Duroc        ---------- ---------- ---------- ---------- ----------

1262
Wild Boar    GCGCCACCTC CATCCAGAGA CCACCACGCC CGCCTTTGGG GCGCGCTCTG
Meishan      ---------- ---------- ---------- ---------- ----------
Large Black  ---------- ---------- ---------- ---------- ----------
Hampshire    ---------- ---------- ---------- ---------- ----------
Pietrain     ---------- ---------- ---------- ---------- ----------
Duroc        ---------- ---------- ---------- ---------- ----------
```

FIG. 12

```
                                                                          1312
Wild Boar     GGGACTTTGC CCCCCACTGG GGTGGGACGT GTGCGGGCAG AAGCTGTCCG
Meishan       ---------- ---------- ---------- ---------- ----------
Large Black   ---------- ---------- ---------- ---------- ----------
Hampshire     ---------- ---------- ---------- ---------- ----------
Pietrain      ---------- ---------- ---------- ---------- ----------
Duroc         ---------- ---------- ---------- ---------- ----------

1362
Wild Boar     GGTGTTGCTC ACTGCAGGAC CTCAGGGGAA GGCCTTCGTG ACTGCTAGGA
Meishan       ---------- ---------- ---------- ---------- ----------
Large Black   ---------- ---------- ---------- ---------- ----------
Hampshire     ---------- ---------- ---------- ---------- ----------
Pietrain      ---------- ---------- ---------- ---------- ----------
Duroc         ---------- ---------- ---------- ---------- ----------

1412
Wild Boar     AGCAGGCGCA GCGCCCCGGC GGAGGGCGGG GCCCCTCTCT TCTACGGCTC
Meishan       ---------- ---------- ---------- ---------- ----------
Large Black   ---------- ---------- ---------- ---------- ----------
Hampshire     ---------- ---------- ---------- ---------- ----------
Pietrain      ---------- ---------- ---------- ---------- ----------
Duroc         ---------- ---------- ---------- ---------- ----------

Wild Boar     AGTG
Meishan       ----
Large Black   ----
Hampshire     ----
Duroc         ----
```

FIG. 12 CONT'D

METHODS FOR ANALYZING ANIMAL PRODUCTS

REFERENCE TO RELATED APPLICATIONS

This application is a Continuation of U.S. patent application Ser. No. 09/450,651, filed Nov. 30, 1999 now abandoned, which is a Continuation of PCT/GB98/01531, filed May 27, 1998, the disclosures of each of which are herein incorporated by reference in their entireties.

The present invention relates to methods for analyzing animals and their products. In particular, the invention relates to methods for differentiating animal products on the basis of breed origin, determining or testing the breed origin of an animal product and for validating an animal product, as well as to kits for carrying out such methods. In addition, the present invention provides methods for the determination of pig genotype with respect to coat colour.

Introduction

Animal Breeds

For thousands of years, selective pressure has been applied by humans in the course of animal husbandry to produce livestock exhibiting certain desirable characteristics. These characteristics have been selected to meet aesthetic, technical, ritual, social and economic needs. The result has been the production of a large number of different animal breeds.

The term "breed" is a term of art used to define a homogenous, subspecific group of domestic livestock with definable and identifiable external characteristics that enable it to be separated by visual appraisal from other similarly defined groups within the same species. The term therefore defines a group of animals to which selective pressure has been applied by humans to give rise to a uniform appearance that is inheritable and distinctive with respect to other members of the species.

As breeds become established, their integrity is maintained by breed societies, herdbooks and pedigree records.

Breed Selection

Conventional breed selection methods are based on direct measurement of the phenotype of an animal and/or its relatives. Thus, the implementation of breeding schemes requires extensive phenotypic record keeping. For example, dairy herd improvement programs in the United States and Western Europe relied in part on the collection of individual records (milk yield and composition, type traits, health traits, etc.) performed on a monthly basis for millions of cows. Likewise, breeding companies carefully monitor their pig and poultry breeding stock for a whole range of phenotypic measurements.

However, some important characteristics are not immediately apparent at the level of the living animal. For example, many parameters of meat quality are determined by subtle physiological or biochemical characteristics which are not readily apparent and so cannot serve as the basis for efficient artificial selection.

Breeding for qualities of this type has relied in part upon selection for other (more readily apparent traits) which are to some extent coinherited (linked or associated) with the desirable characteristics. For example, in the pig industry lop ears have in the past been associated with mothering ability and so have been used as a marker for this trait.

Conventional breed selection methods are limited by the fact that some phenotypes are expressed only in one sex or at a specific developmental stage. Moreover, some phenotypes are difficult and costly to measure. Indirect detection of such phenotypic traits via DNA-based diagnosis (for use in marker-assisted selection or MAS) is therefore seen as a desirable alternative to direct measurement of phenotypic parameters (see Georges and Andersson (1996), *Livestock genomics comes of age*, Genome Research, Vol. 6: 907-921). However, the gene structure-function relationships underlying many of the desirable traits are often highly complex and not yet sufficiently well-established to make such an approach feasible in practice.

Breed Identification

The definition of animal breeds is currently at a watershed. Whereas previously they have been defined by overt physical characteristics and pedigree records, in the future as new breeds are developed from specific breeding lines they will be defined by sets of DNA markers. The work described herein allows not only the most accurate approach to breed determination currently possible in a range of products but also allows the integration in a common format of breed determinant information obtained through use of the present invention with that which will be used in the future. The present invention therefore allows not only the determination of source breed in the current environment but also links this to the development of future breeds and their unique identification.

It is generally recognized that the only definitive way to identify a particular animal as a representative of a given breed is through its pedigree. Thus, despite the fundamental importance of overt phenotypic traits in the breeding process and in the maintenance of breed purity, those skilled in the art generally consider that breed identity cannot be definitively characterized on the basis of visual inspection of such traits. By way of example, the genetic factor causing the belt phenotype in pigs is dominant to the non-belted form. Thus, a belted animal may result from an animal of a belted breed such as Hampshire being crossed with a non-belted breed.

As stated in PIGS A handbook to breeds of the world, V. porter, Helm Inf. Ltd, ISBN 1-873403-17-8, 1993, page 16, "What is a Breed?":

Appearances can be deceptive: never judge a pig breed by its coat!

However, in many circumstances breed identification on the basis of direct evidence of pedigree is difficult or impossible. Thus, in practice, so-called "breed markers" may be used to determine breed identity.

The term "breed marker" is a term of art which defines a measurable characteristic which on the basis of empirical data appears to be breed specific. Breed markers include genotypic features such as DNA polymorphisms, chemical features such as protein and water contents of meats, epigenetic/biochemical features (such as protein polymorphisms), chromosome structure, gene copy number, DNA fingerprinting, microsatellite analysis and RAPD DNA markers.

Other useful markers include breed determinants. The term "breed determinant" is used herein to indicate an overt phenotypic characteristic which is used (at least in part) as the basis of artificial selection during breeding programmes. It is used in contradistinction to the term "breed marker", which (as explained above) is used herein to define other characteristics which appear to be breed specific on the basis of empirical data. The term "breed determinant gene" is used to indicate a gene which is involved (at least in part) in the expression of the corresponding overt phenotypic characteristic.

Some breed determinants (e.g. coat colour) have traditionally been used as breed "trademarks", and so have long served as an indication of pedigree (and breed identity). Other breed determinants that have also been selected for in breed development include features such as ear carriage, face shape and general anatomical conformation. The advantage of breed determinants relative to simple breed markers is the inseverable link between the characteristics of the breed and the determinant.

Biochemical and Genetic Tests for Breed Identity

Many of the breed markers discussed above can be characterized using biochemical or genetic tests. Such markers include genotypic features (e.g. DNA polymorphisms), biochemical features (e.g. protein polymorphisms), chromosome structure, gene copy number, DNA fingerprints, microsatellite patterns and RAPD DNA markers.

However, there are significant problems associated with such tests, as discussed below:

Tests based on the chemical composition of animal products (e.g. meat or seminal plasma) may be compromised by the fact that the chemical profile varies between sites in the animal (i.e. different muscles) and is affected by diet, age, sex and sample storage conditions. Moreover, the results obtained are usually quantitative in nature, leading to problems with interpretation and comparison between different test sites.

Tests based on protein polymorphisms are limited by the fact that the distribution of any given protein is unlikely to be uniform, so that the protein of interest is absent in certain tissues. Thus, a number of different polymorphism markers may be required to check all products of interest for breed provenance. Moreover, such tests are based on antibody assays, and a significant investment is also required to develop the reagents for a specific antibody test.

Chromosome structure analyses are compromised by the high level of skill required for cytogenetical methodology and interpretation and the elaborate precautions and care required for sample preservation. Such markers are poorly applicable on anything but materials derived from living or newly deceased animals.

Classical DNA fingerprinting is based upon regions of repeated DNA sequence that due to their structure show a large degree of variation in length within a population. Such regions are often present in a number of copies within the DNA of an individual, thus increasing the potential for individual variation. By separating fragments of the total DNA according to size and then defining the position (and so size) of the hypervariable region using a specific probe, a fingerprint of a series of bands for a particular individual can be obtained. A number of probes for hypervariable regions of DNA have been examined in pigs (including M13 viral sequences and human minisatellite probes) and it is claimed that specific bands were found in each breed.

Random Amplified Polymorphic DNA (RAPD) markers are based upon PCR amplification of DNA fragments using primers of random sequence. Such reactions generally give rise to a number of DNA fragments which can be characterised according to size by gel electrophoresis. If the products of reactions based upon DNA from different breeds are examined there is the possibility of finding certain DNA bands which are breed specific. However, there is in most cases no direct link between the alleles of such repeat series present and the features determining the actual nature of the breed. This, combined with the hypervariable nature of these regions of DNA, results in them rarely being breed specific (similar alleles being found in a number of different breeds).

As there is no link to the phenotype of the breed there is a greater risk that cross specific alleles could exist or arise in a breed, whereas this is unlikely with breed determinants as they define the phenotype itself. Given the large number of populations of animals of specific breeds that exist, extensive research would have to be carried out to exclude a DNA marker from breeds other than that with which it is claimed to be linked.

However, a major drawback with this approach is that RAPD markers are considered to be unreliable and found to be subject to variation between laboratories. Such problems are exacerbated when samples of different types and history must be analyzed and compared.

There is therefore a need for reliable breed markers which can be used as the basis for rapid and inexpensive methods for identifying the breed provenance of various animal products and for validating animal products (such as foodstuffs and semen for use in breeding programmes).

It has now been recognized that breed determinants as hereinbefore defined (such as coat colour) have unexpected advantages as breed identifiers or breed specific markers. In particular, it has surprisingly been discovered that the use of overt phenotypic characteristics as the basis for selection over long periods of time has led to particular alleles becoming fixed in most breeds. Such breed markers can be used to provide industry standard profiles for a particular breed that has application to all materials derived from a particular species.

Thus, it has now been found that many breeds are in fact genetically homogenous with respect to breed determinant genes (as hereinbefore defined), so that these genes may serve as the basis of reliable breed-specific markers (contrary to the prejudice in the art mentioned earlier regarding the utility of breed determinants per se, such as coat colour, in breed identification).

Moreover, it has surprisingly been found that the nature of the breed determinant genes (or alleles thereof) underlying any one breed determinant (such as coat colour) may be highly polymorphic. Thus, variation in breed determinant genes and/or alleles between different breeds may exist, notwithstanding the fact that the different breed determinant genes/alleles may contribute to the expression of the same overt phenotypic characteristic.

Prior to the present invention, it was assumed that the corresponding genetic determinants would be insufficiently polymorphic to provide a useful basis for distinguishing between breeds. For example, coat colour was known to be shared among different breeds of pig and (as mentioned above) was therefore not regarded as a good candidate for a breed specific marker. However, the present inventors have found that the alleles underlying the coat phenotype in such breeds are in fact highly polymorphic and often distinctive (and so useful as the basis for breed identification).

Similar considerations apply to other overt physical traits (breed determinants), which may therefore be shared by different breeds while nevertheless associated with distinct genes/alleles in each breed. An example of this is seen in cattle exhibiting the double muscled phenotype. Work by Kambadur et alia (1997, Genome Research 7, 910-915) and Grobet et alia (1997, Nature Genetics 17, 71-74) illustrates that the double muscled phenotype of cattle is caused by mutations in the myostatin gene. However, in the Belgian Blue and Asturiana breeds, this gene contains an 11 bp deletion whereas in the Piedmontese breed a G to A transition is present. Thus, as with porcine coat colour a single selected characteristic is caused by a number of potential polymorphisms. However, the nature of the arisal and selection history for such overt physical characteristics leads to the fixation of particular alleles within the breeds contributing to the breed specific profile of determinants.

In the light of these findings, it has now been recognized that genetic analysis of breed determinants (such as coat colour) provides an effective means for validating animal products (e.g. foodstuffs) and may advantageously be incorporated into animal product (e.g. food) processing lines to monitor and maintain product quality and into quality control protocols in the food industry.

Coat Colour

Pig breeds show a variety of coat colours and these are often associated with particular production characteristics. For example, white is the predominant coat colour among European commercial breeds e.g. Large White and Landrace, and these breeds are associated with larger litters and good mothering ability. However, there are a number of commercially important coloured breeds, demonstrating a number of colours and combinations. The Duroc, associated with meat tenderness, is red, the Pietrain, a heavily muscled animal which produces a very lean carcass, is spotted, and the Hampshire, also heavily muscled, is black with a white saddle over its shoulders. In addition, there may be other useful local breeds which have traits of potential commercial interest, and which are coloured. For example, the Chinese Meishan breed has been imported into Europe and the US because of its very large litter size. The European Wild Boar is brown when adult and striped when juvenile, and this breed is utilised to satisfy consumer demand for traditional meat products. It is also claimed that other local breeds or landraces are important because of their adaptation to local environments, e.g. temperature, endemic diseases and local feedstuffs.

Coat colour is important to the pig industry for a number of reasons. Firstly, gross variation in appearance (i.e. a range of coat colours) of pigs claimed to be genetically consistent for traits other than coat colour can lead to questions about the consistency and quality of the animals in the mind of pig-producers. Thus, the coat colour of the pig is often used as a trademark of the breed and the breeders want to ensure that their animals breed true for colour. For example, in several markets, local, traditional, coloured breeds are marketed for their meat quality or in terms of the production system used to rear them. However, this is not a trivial task since the coat colour is controlled by a number of genes. The inheritance is also complicated by the presence of dominance and interaction between genes. There is also an application in the assessment of the purity of the genetics of traditional breeds used as the basis for modern synthetic lines and the confirmation of the derivation of the latter.

Secondly, in a number of markets there is a preference for white skinned meat. This is due to the fact that pork is often marketed with the skin still attached, and skin from coloured pigs, even if dehaired, can still exhibit colour, which can lead to negative perception by the consumer partly, since the surface of the meat may appear to be spotted by mould. It is therefore necessary in these markets to remove the skin from such carcasses, entailing additional cost. For example, in the US, coloured carcasses are associated with approximately 1% skin defects requiring dehairing and skinning to remove pigment. As a result of this, coloured pig carcasses are generally discounted.

One example of the problem concerns the presence of black pigmented spots occurring in production animals that are crossbreds between a white and a pigmented line. This may occur because the dominant white gene inherited from the white breed is not always fully dominant in the heterozygous condition which occurs in this cross. A possible solution to this problem would be to ensure that the production animals are homozygous for the recessive red allele present in breeds such as the Duroc. In this case the pigmented spots would be red instead of black and much less conspicuous. To achieve this one needs to breed the recessive red allele to homozygosity in both the white and pigmented line used for cross-breeding. However, this would be very difficult using phenotypic selection as selection for a red background colour in a white line could only be accomplished with very expensive progeny testing schemes.

In addition, pig breeders would like to be able to be in a position to ensure consistency in breeding populations. Breeders may wish to ensure that progeny produced by breeding crosses were always white. Alternatively, a breeder of Duroc or Hampshire pigs may wish to ensure that breeding crosses always produced the characteristic Duroc or Hampshire colouring. Traditional animal breeding practices have in the past, been used to attempt to eliminate untypical colour from pig lines. For example purebred breeders must submit potential boars for progeny testing in order to demonstrate that they are suitable for inclusion in the breeding herd. This procedure incurs significant cost, including the substantial delay to confirm sufficient matings and progeny have been produced before the animal can be used commercially.

Therefore, selection based on a diagnostic DNA test for mutations in coat colour genes would be a major advance compared with phenotypic selection. Coat colour is determined by the action of a number of different gene loci. For example, the gene determining whether a pig is white or coloured is designated I (for inhibition of coat colour). The version of the gene preventing the expression of any colour (I) is dominant to that which allows colour to develop (i). Traditional selection for white animals has reduced the frequency of i, but it still remains in the population of white heterozygous carrier animals. Recently, a number of structural differences in the alleles of the KIT gene were identified and found to be involved with this aspect of coat colour determination which allowed the development of methods of distinguishing between alleles at this locus.

However, animals which carry two copies of the recessive allele, i, at this locus have non-white coat colours (Johansson-Moller et al., *Mamm. Genome*, 7:822-830 (1996), WO-A-97/05278, the disclosure of which is incorporated herein by reference). Pigs of this type can be all one colour, such as the Duroc (which is red), or have combinations of colours (particularly spotted or striped or banded patterns, such as the Pietrain and Hampshire, respectively). Many other combinations are possible and are observed (see the table, below):

| Genotype | Colour |
|----------|--------|
| I/I | White |
| I/i | White |
| i/i | Coloured |
| I$^P$/I$^P$ | White with coloured spots |
| I$^P$/I | White |
| I$^P$/i | White with coloured patches |

The non-white colour in such animals may be varying shades of red or black. The type of colour expressed is determined by the action of a second gene which is designated E (for extension of coat colour). Based on the literature, animals which contain the E version of the gene are completely black, and this version of the gene is dominant to that which results in red coat colour (e). Patched or spotted animals, such as the Pietrain breed, contain a third version of the gene designated EP. This version of the gene is dominant to e but not to E. For example, black animals may have the genotype, iiEe, iiE$^p$ or iiEE. A black sow and a black boar which were both heterozygous at the E locus and which were of the genotype iiEe would produce both black and red piglets in the ratio 3:1. The black piglets would be iiEE or iiEe and the red piglets would be iiee.

The density and coverage of coat colour and the position of bands of white are determined by additional loci, one of which, the belt locus, is discussed later in this application. For example, the Hampshire breed is background black with a white band across its shoulders, the width of this band may vary, however, the colour should be black. There is evidence that some Hampshire animals are derived from herds that have been crossed previously with red breeds, such as the Duroc. In this situation, the red version of the gene can be maintained silently in the heterozygous state. When two heterozygotes are crossed 25% of the offspring will contain red. In some cases such pigs will have the appearance of the Duroc breed, being solid red, however, in other cases, the animals will have the white band inherited from the Hampshire and have the appearance of red Hampshires. It is the presence of the atypical coat colour rather than the pattern that is important in this situation.

The extension locus is known in other breeds of domestic animals, such as the horse, where e is associated with chestnut colour (Adalsteinsson et al., *J. Hered.* 65:15-20 (1974)), cattle (Klungland et al., *Mammalian Genome* 6: 636-639 (1995)), the fox (Adalsteinsson, *J. Hered.* 78:15-20 (1987)) and the mouse (Jackson, *Ann Rev Genet.* 28: 189-217 (1994)). The extension locus encodes the alpha melanocyte-stimulating hormone receptor (αMSHR). It has been shown that recessive alleles at this locus do not express a functional αMSH receptor (Robbins et al., *Cell*, 72: 827-834(1993), Klungland et al., *Mammalian Genome* 6: 636-639 (1995)) and these workers have identified mutations in the sequence of the αMSHR gene in these species associated with different coat colours.

Classical segregation analyses have identified a minimum of three alleles at the pig extension locus: E for uniform black, E$^p$ for black spotting and e for uniform red (Ollivier and Sellier, *Ann. Génét. Sél. Anim.,* 14:481-544, (1982)). The dominance relationship among the three alleles is as follows E>E$^p$>e. We have now found that these coat colour variations are associated with sequence polymorphism in the αMSHR gene in the pig. We have analysed the DNA sequence of this gene using samples from the following breeds with different coat colour: Wild Boar which is wild type coloured, Meishan and Hampshire which carry alleles for uniform black (E), Pietrain and Large White which carry alleles for black spotting (E$^p$) and Duroc which is uniform red (e). In Large White the patches or spots of colour that might be expected due to the presence of the E$^p$ allele are hidden as this breed also carries the dominant white gene which prevents any expression of colour. Five different αMSHR sequences were obtained one from the Wild Boar, one from Meishan, one from Duroc, one from Hampshire, and one found in Pietrain and Large White. We have designated the allele found in the Wild Boar as E$^+$ and assume that the presence of this allele is necessary for the expression of the wild type colour. The E alleles for uniform black carried by Meishan and Hampshire pigs were associated with different αMSHR sequences. We have denoted these two alleles E$^m$ and E$^h$, respectively. The DNA sequence associated with the allele for black spotting found in Pietrain was denoted E$^p$. The similarity of the E$^p$ and E$^h$ alleles suggests that they are derived from a common origin. The sequence differences presented here can be used as the basis of methods and kits to determine the genotype of pigs in relation to coat colour. Alternatively, alleles of linked markers, such as microsatellite or AFLP markers, found to be in linkage disequilibrium with these alleles could be used to predict colour genotype. In conclusion we have found five different αMSHR sequences associated with five different extension alleles i.e. E$^+$, E$^m$, E$^h$, E$^p$ and e.

Except for the 2 base pair insertion at the 5' end of the E$^p$ allele and the 1 bp deletion in the 3' untranslated region of the E$^m$ allele the DNA sequence differences identified in the αMSHR gene are single base pair changes. Some of these are silent, however, a number lead to changes in the amino acid sequence of the αMSHR protein. For example, the differences between e and the other alleles are two missense mutations in the coding sequence of the αMSHR gene. Importantly, the differences in the pig gene are different from that found in other species. The cattle and mouse e mutations are one base pair deletions (Robbins et al, *Cell*, 72: 827-834 (1993); Klungland et al, *Mammalian Genome* 6: 636-639 (1995), Joerg et al, *Genome* 7: 317-318 (1996)), whilst the mutations identified here include a missense mutation (G727 changed to A) in a region which is conserved among human, mouse, cattle and horse gene sequences (Wikberg et al, WO 94/04674 (1994), Valverde et al, *Nature Genet.* 11: 328-330 (1995), Robbins et al, *Cell*, 72: 827-834 (1993), , Klungland et al, *Mammalian Genome* 6: 636-639 (1995), Joerg et al, *Genome* 7: 317-318 (1996), Marklund et al, *Mamm. Genome,* 7:895-899 (1996)). The E$^p$ group has a dinucleotide insertion in the 5' end of the gene after nucleotide position 66 of the Wild boar sequence which leads to the creation of a stop codon further into the gene resulting in a predicted mutant polypeptide of only 54 amino acids. Finally, the Meishan allele (E$^m$) shows four amino acid changes in the protein. Two of these differences are in the same region of the gene which is altered in cattle.

The colours of a series of pig breeds, the classical genotypes for I and E and the determined genotypes for E based on sequencing and testing studies are shown in the table below:

| Breed | I locus | E locus | Colour |
| --- | --- | --- | --- |
| Hampshire | i/i | E$^h$/E$^h$ | Black with white belt |
| Large White | I/I | E$^p$/E$^p$ | White |
| Landrace | I/I | E$^p$/E$^p$ | White |
| Pietrain | i/i | E$^p$/E$^p$ | White with black patches |
| Berkshire | i/i | E$^p$/E$^p$ | Black with white points |
| Meishan | i/i | E$^m$/E$^m$ | Black or black with white points |
| Duroc | i/i | e/e | Red |
| Wild Boar | i/i | E$^+$/E$^+$ | Brown (banded hair) |

Thus, it is possible to distinguish between the alleles of E$^+$, E$^m$, E$^h$, E$^p$ and e and so determine the genotype of individual pigs (or the genetic provenance of products derived therefrom) with respect to non-white coat colour. Interestingly, the white breeds that have been examined all appear to be fixed for alleles E$^p$ at the E locus. There is considered to be potentially some modifying effect of the E locus on the phenotype conferred by the I locus. While the basis of this is not established, the fixing of E$^p$ in these lines illustrates the subtle effects on loci involved with coat colour upon selection for breed characteristics thus providing more determinants among such loci than might be expected.

Associations can be determined between extension locus genotype and linked markers, eg microsatellite sequences which are linked to the gene. A number of microsatellite markers have been located to the region of porcine chromosome 6 to which the αMSHR gene has been mapped.

A number of pig breeds characteristically show the belt phenotype consisting of a continuous white belt over the shoulders and white fore legs. Examples of breeds demonstrating this characteristic are the British Saddleback (derived from the Wessex and Essex breeds) and the Hampshire, which show a white belt upon a black background and the Bavarian Landschwein characterised by a white belt upon a red background. The characteristic is controlled by a dominantly acting locus Belt designated Be for which there are thought to be two alleles (Legault 1997 in The Genetics of the Pig, Ed Rothschild M. F. and Ruvinsky A, Publ. CAB International) (Ollivier and Sellier, Ann. Génét. Sél. Anim., 14:481-544, (1982)). Be giving rise to a belt and be which in the homozygous form leads to the absence of a belt. The heterozygous animal Be/be carries a belt but in this genotype the belt is generally narrower in character.

To identify the actual genetic basis of the belted and non belted phenotype studies were carried out using animals from a Pietrain x (Pietrain x Hampshire) cross. The Pietrain is be/be while the Hampshire is Be/Be. Thus the F1 generation all have the genotype Be/be. Further crossing of the F1 back to the Pietrain (be/be) leads to the segregation of the Be allele between offspring, giving rise to Be/be animals showing belts and be/be non belted offspring. A correlation was then established between the inheritance of the belted condition and certain microsatellite markers within these pedigrees. This work surprisingly identified the actual gene involved as the KIT gene also described above as involved in dominant white. Further analysis showed correlation of the phenotype in this pedigree with a polymorphism at KIT nucleotide 2678 with a C or T occurring at this position. The presence of a C creates a restriction site for Aci I which is absent when T is present. Based upon these unexpected findings a number of approaches can be taken to the determination of the genotype for an animal at the belt locus using either single nucleotide polymorphisms or linked markers including microsatellites or other single nucleotide polymorphisms. Thus animals can be genotyped by a number of approaches to determine their genetic status for this particular overt characteristic.

SUMMARY OF THE INVENTION

According to the present invention there is provided a method for differentiating animals and animal products on the basis of breed origin, for determining or testing the breed origin of an animal product or for validating an animal product, wherein the method comprises the steps of: (i) providing a sample of the animal product; and (ii) analyzing the allele(s) of one or more breed determinant genes present in the sample.

As explained above, the breed determinant is an overt phenotypic trait. As used herein, an overt phenotypic trait is one which can be visually recognized.

Differentiation of animal products on the basis of breed origin involves the partition of members of a class of different animal products into a number of different products sharing the same breed origin. It does not necessarily imply identification of the nature of the breed source. Animal product differentiation of this kind basis may be sufficient where the consistency of source of animal products must be monitored (but its actual breed provenance is not important).

In contrast, determination of the breed origin of an animal product implies identification of the breed source, while testing the breed origin implies analysis sufficient to determine whether a breed source other than that desired has been used (without necessarily identifying such other breed sources in cases where they are indicated).

Validating an animal product implies confirming that it meets stipulated specifications as to breed provenance. Such validation may involve differentiation, determination and/or testing, depending on the circumstances under which the analysis is performed and the nature and extent of ancillary data which may be available.

The sample for use in the invention may be in any convenient form. In many cases, the sample will be a sample of a food (e.g. meat product). For most applications, the sample is pre-treated (e.g. extracted, purified and/or fractionated) in such a way so as to make the alleles of a breed determinant gene or genes available for analysis (either at the level of nucleic acids (such as RNA or DNA) and/or proteins). The sample is preferably a nucleic acid sample, in which case the analysing step (ii) comprises DNA or RNA analysis. Alternatively, the sample may be a protein sample (where the nature of the protein reflects a breed determinant allele), in which case the analysing step (ii) comprises protein analysis.

The breed determinant of the invention may be a monogenic or polygenic trait. Monogenic traits are preferred, since the genes conferring such traits are relatively easily identified and analyzed. However, in some cases it may be useful to analyze the alleles of polygenic traits (i.e. traits which are controlled by a plurality of genes), since the underlying allele polymorphism is often greater in such cases (so increasing the potential for breed differentiation).

Typically, overt phenotypic traits are those traits which have been used as the basis for artificial selection during the breeding programme. The overt phenotypic trait is preferably a behavioural or morphological, physiological or behavioural trait.

The overt phenotypic trait may vary qualitatively or quantitatively between breeds. Preferred are traits which vary qualitatively between breeds, since such traits are often reflected by qualitative differences in the alleles of the corresponding breed determinant gene(s). In such cases, analysis yields relatively robust positive-negative results, which are easily interpreted and compared between testing stations/laboratories.

The breed determinant gene analysed in step (ii) may be any suitable breed determinant gene. Such genes may be identified and analysed by methods well known in the art using routine trial and error. Preferably, they are selected from any of a coat colour, pattern, texture, density or length gene; a ear aspect gene; a double muscling gene; a horn morphology gene; a tusk morphology gene; an eye colour gene; a plumage gene; a beak colour/morphology gene; a vocalization (e.g. barking) gene; a comb or wattle gene; and/or a gene controlling display behaviour.

In preferred embodiments, the breed determinant gene is the KIT and/or αMSHR coat colour gene (for example, the pig KIT and/or αMSHR gene).

The analysis step (ii) may comprise any of a wide range of known nucleic acid/protein analytical techniques. The nature of the analytical technique selected is not critical to the practice of the invention, and those skilled in the art can readily determine the appropriate technique according to the circumstances in which the analysis is to be conducted and the type of data required.

Preferably, the analysis step (ii) comprises selectively amplifying a specific fragment of nucleic acid (e.g. by PCR), testing for the presence of one or more restriction endonuclease sites within the breed determinant gene(s) (e.g. restriction fragment length polymorphism (RFLP) analysis), determining the nucleotide sequence of all or a portion of the breed determinant gene(s), probing the nucleic acid sample with an allele-specific DNA or RNA probe, or carrying out one or more PCR amplification cycles of the nucleic acid sample using at least one pair of suitable primers and then carrying out RFLP analysis on the amplified nucleic acid so obtained.

Alternatively, the analysis step (ii) comprises probing the protein sample with an antibody (e.g. a monoclonal antibody) specific for an allele-specific epitope, electrophoretic analysis, chromatographic analysis, amino-acid sequence analysis, proteolytic cleavage analysis or epitope mapping. For example the E$^p$ allele might be distinguished by any method capable of detecting an alteration in the size of the encoded protein.

In particularly preferred embodiments, the analysis step (ii) comprises determining the nucleotide sequence of the KIT and/or αMSHR gene or the amino acid sequence of the KIT and/or αMSHR protein. Here, the analysis may comprise establishing the presence or absence of at least one mutation in the KIT and/or αMSHR gene. Any method for identifying the presence of the specific sequence change may be used, including for example single-strand conformation polymorphism (SSCP) analysis, ligase chain reaction, mutagenically separated PCR, RFLP analysis, heteroduplex analysis, denaturing gradient gel electrophoresis, temperature gradient electrophoresis, DNA sequence analysis and non-gel based systems such as TaqMan™ (Perkin-Elmer).

In the TaqMan™ system, oligonucleotide PCR primers are designed that flank the mutation in question and allow PCR amplification of the region. A third oligonucleotide probe is then designed to hybridize to the region containing the base subject to change between different alleles of the gene. This probe is labelled with fluorescent dyes at both the 5' and 3' ends. These dyes are chosen such that while in this proximity to each other the flourescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the florescence from the dye at the 3' end of the probe. The discrimination between different DNA sequences arises through the fact that if the hybridization of the probe to the template molecule is not complete (i.e. there is mismatch of some form), then cleavage of the dye does not take place. Thus only if the nucleotide sequence of the oligonucleotide probe is completely complementary to the template molecule to which it is bound will quenching be removed. A reaction mix can contain two different probe sequences each designed against different alleles that might be present thus allowing the detection of both alleles in one reaction.

Although the TaqMan™ system is currently capable of distinguishing only two alleles, labelled probe primer sets could be developed in which the probes for certain target allele(s) are labelled with a different fluorescent dye from non target alleles. For example, if one wished to confirm that a group of Duroc breed pigs carried only allele e one could have a probe present capable of detecting this allele labelled with one fluorescent dye and probes capable of detecting all the other alleles labelled with the second dye. Thus one would detect the presence of any non Duroc type alleles at this locus. Such probe sets could be designed and labelled according to the needs of the experiment.

The analysis step (ii) may further comprise determining the association between one or more microsatellite marker alleles linked to the KIT and/or αMSHR gene and to particular alleles of the KIT and/or αMSHR gene.

Alternatively, the analysis step (ii) may be based on the identification of microsatellite markers present in the nucleic acid sample.

The analysis step (ii) preferably comprises: (a) determining the association between one or more microsatellite marker alleles linked to the KIT and/or αMSHR gene and to particular alleles of the KIT and/or αMSHR gene; determining which microsatellite marker allele or alleles are present in the nucleic acid sample.

The analysis step (ii) preferably further comprises the step of determining the genotype of at least one additional locus, for example an additional breed determinant (e.g. coat colour) locus. Particularly preferred as an additional locus is the KIT gene locus (e.g. the pig KIT gene locus).

The analysis step (ii) preferably comprises PCR using at least one pair of suitable primers. In the case where the gene is the pig αMSHR gene, the at least one pair of suitable primers is:

```
αMSHR Forward Primer 1:           (SEQ ID NO:1)
(5'-TGT AAA ACG ACG GCC AGT RGT GCC TGG AGG TGT-3')

αMSHR Reverse Primer 5:           (SEQ ID NO:2)
(5'-CGC CCA GAT GGC CGC GAT GGA CCG-3'); or αMSHR Forward Primer 2:           (SEQ ID NO:3)
(5'-CGG CCA TCT GGG CGG GCA GCG TGC-3')

αMSHR Reverse Primer 2:           (SEQ ID NO:4)
(5'-GGA AGG CGT AGA TGA GGG GGT CCA-3'); or αMSHR Forward Primer 3:           (SEQ ID NO:5)
(5'-GCA CAT CGC CCG GCT CCA CAA GAC-3')

αMSHR Reverse Primer 3:           (SEQ ID NO:6)
(5'-GGG GCA GAG GAC GAC GAG GGA GAG-3')
```

The analysis step (ii) may also comprise restriction fragment length polymorphism (RFLP) analysis, for example involving digesting the pig nucleic acid with one or more of the restriction enzymes BstUI, HhaI and/or BspHI. In cases where the gene is the pig αMSHR gene, this analysis may involve identification of a polymorphism at any of the nucleotide positions shown to be polymorphic including 283, 305, 363, 370, 491, 727, 729, 1162 or between nucleotide positions 60 and 70 or between nucleotide positions 1005 and 1010 of the pig αMSHR gene.

The analysis step (ii) may involve carrying out one or more PCR amplification cycles of the nucleic acid sample using at least one pair of suitable primers and then carrying out RFLP analysis on the amplified nucleic acid so obtained to determine the KIT or αMSHR genotype of the pig. Here, when the gene is the pig αMSHR gene the at least one pair of suitable primers is as defined above.

The animal product preferably comprises or consists of meat (e.g. processed and/or canned meat), egg, egg swab or washing, semen, blood, serum, sputum, wool, biopsy sample or leather. It may comprise genomic DNA, RNA or mitochondrial DNA.

The animal is preferably a mammal (e.g. pig, cattle, dog, cat, horse, sheep, rodent or rabbit), fish (e.g. salmon or trout) or bird (e.g. chicken or turkey).

The invention may be used with extremely small samples and can be used to screen large numbers of samples quickly and inexpensively. The invention may be adapted to yield absolute results, and quantification is not essential. Moreover, only small fragments of nucleic acid are required, and the same tests can be used on the majority of animal products.

Applications

The invention finds application in a number of areas. For example, certain breeds are considered to yield meat of higher eating quality, and a number of retailers now market products which claim to be derived from specific or traditional breeds (for example, Wild Boar crosses). The invention enables consumer organisations to validate these claims and also permits retailers to monitor the quality of the products with which they are being supplied (i.e. perform product validation). The invention finds particular application in validation studies carried out and used by retailers to support consumer confidence, since the linkage between a genetic marker and an overt physical feature is more readily grasped by the lay person than the concept of breed specific markers. This makes the use of such breed determinants attractive and also offers marketing opportunities for retailers to underpin validation schemes.

There are also a number of reports of breed influences on the quality of hams produced by various meat processing techniques. For example, in one report hams from three different pig breeds were reliably classified on the basis of sensory descriptors of marbling, saltiness and dry cure flavour. The breed identification processes of the invention enables producers to validate raw materials as part of quality control.

The ability to enforce and validate raw material source uniformity also yields improved process control, lower costs and greater product consistency, since it has now been found that heterogeneity in chemical composition of products from different breeds is an important factor in flavour profile variation and there may also be differences in the functionality of other meat components between breeds.

The invention also finds utility in the maintenance of stock purity by animal (e.g. pig) breeders. The small size of traditional breed populations means that the maintenance of a gene pool of sufficient size to avoid the effects of inbreeding requires the importation and movement of stock between separate populations. A risk of genetic contamination is associated with such movements, and the invention may be used to reduce or eliminate these risks. The maintenance of biodiversity and the rare breeds providing the reservoir for this diversity provides an increasing need for breed identifiers. There is for example a problem for breeders of the British Saddleback. Certain bloodlines of this breed carry a higher frequency of the be allele of the belt locus which can result in the production of belt-less animals which do not reach the required breed standard and decrease the value not only of that individual animal but of the whole litter. The ability to select against this allele when new bloodlines are introduced to an existing population would enable breeders to increase the genetic diversity without the risk of lowering the relative standard of the particular population to that of the breed in general.

The invention may also be used as part of a breeding programme to confirm particular crosses. This may be of enormous value in the establishment of pyramid breeding schemes. Particular breed characteristics such as coat colour, body shape and ear aspect are often altered in such crosses, yet there is a need to be able to confirm the presence of genetics of the desired parents.

Such visible breed characteristics for the visible confirmation of crosses are also absent in the use of artificial insemination, where semen may be supplied from pigs in distant geographical locations.

In addition, the skilled person will appreciate that based on the information described herein, it is possible to provide tests for determining pig genotype, with respect to coat colour. Thus, the present invention also provides a method of determining the coat colour genotype of a pig which comprises:

(i) obtaining a sample of pig nucleic acid; and
(ii) analysing the nucleic acid obtained in (i) to determine which allele or alleles of the αMSHR gene are present.

In one embodiment of this aspect of the invention the determination in step (ii) is carried out by determining the nucleotide sequence of the αMSHR gene and, in particular, is based on determining which missense, insertion or deletion mutation is present in the coding region of the gene.

In another embodiment one could first determine the association between microsatellite or other linked marker alleles linked to the αMSHR gene and particular alleles of the αMSHR gene. Thus, the determination in step (ii) would be based on identification of microsatellite marker alleles present in the nucleic acid sample.

In a further aspect, therefore, the present invention provides a method of determining the coat colour genotype of a pig which comprises:

(i) determining the association between one or more microsatellite or other linked marker alleles linked to the αMSHR gene and particular alleles of the αSHR gene;
(ii) obtaining a sample of pig nucleic acid; and
(iii) analysing the nucleic acid obtained in (ii) to determine which microsatellite or other linked marker allele or alleles are present.

The determination of the alleles at the extension locus will indicate the background colour of the animal and in some cases the pattern of mixed colouration, i.e. spotting, but will not necessarily determine the coat colour of resulting progeny. This will be dependent on the genotype at other loci such as the dominant white locus, I. The genotype at the I locus can be determined separately as described in WO-A-97/05278.

Thus, suitably, the methods as described above may further comprise the step:

(iii)/(iv) determining the genotype of additional coat colour loci.

An example of such an additional coat colour locus is the belt locus.

In a preferred method PCR is carried out using primers that amplify a regions of the KIT gene containing nucleotide 2678. An example of a suitable pair of primers is:

```
forward primer
LA93                                          (SEQ ID NO:7)
5'-GAGCAGCCCCTACCCCGGAATGCCAGTTGA-3' and the reverse primer

KIT56                                         (SEQ ID NO:8)
5'-CTTTAAAACAGAACATAAAAGCGGAAACATCATGCGAAGG-3'
```

The method of analysis enables determination of the presence of a C or T at position 2678. Suitable, the restriction enzyme Aci I can be used since the presence of a C creates a restriction site which is absent when a T is present.

Similar examinations within a pedigree will allow the determination of the genotype of offspring.

Thus, in additional aspect, the present invention provides A method of determining the coat colour genotype of a pig which comprises:

(i) obtaining a sample of pig nucleic acid: and
(ii) analysing the nucleic acid obtained in (i) to determine whether the KIT gene carries any polymorphism associated with Belt genotype.

Preferably, the method comprises RFLP analysis which is suitably carried out on a sample of pig genomic DNA which has been amplified using PCR and a pair of suitable primers.

Preferred methods for identifying the presence of the specific sequence change are described above in relation to breed determinants.

BRIEF DESCRIPTION OF THE FIGURES

FIG. 1: Partial nucleotide sequence (a) and the derived amino acid sequence (b) of the porcine αMSHR gene as determined from a number of pig breeds. Position numbers for the nucleotide sequence are based upon nucleotide 1 being the A of the ATG initiation codon. Numbers of the amino acids are in accordance with the bovine BDF3 sequence (Vanetti et alia, *FEBS Lett.*, 348: 268-272 (1995)) to allow comparison.

FIG. 2: Agarose gel electrophoresis of DNA fragments obtained by digestion of DNA fragments amplified from the porcine αMSH-R gene with BstUI or HhaI. Lanes labelled M contain DNA markers of 50, 150, 300, 500, 750, 1000 bp. The other samples were derived from:

| | |
|---|---|
| 1. | Pietrain |
| 2. | Pietrain |
| 3. | Large White |
| 4. | Large White |
| 5. | Large White |
| 6. | Duroc |
| 7. | Duroc |
| 8. | Hampshire |
| 9. | Meishan |
| 10. | Berkshire |
| 11. | Berkshire |

Figure 3:
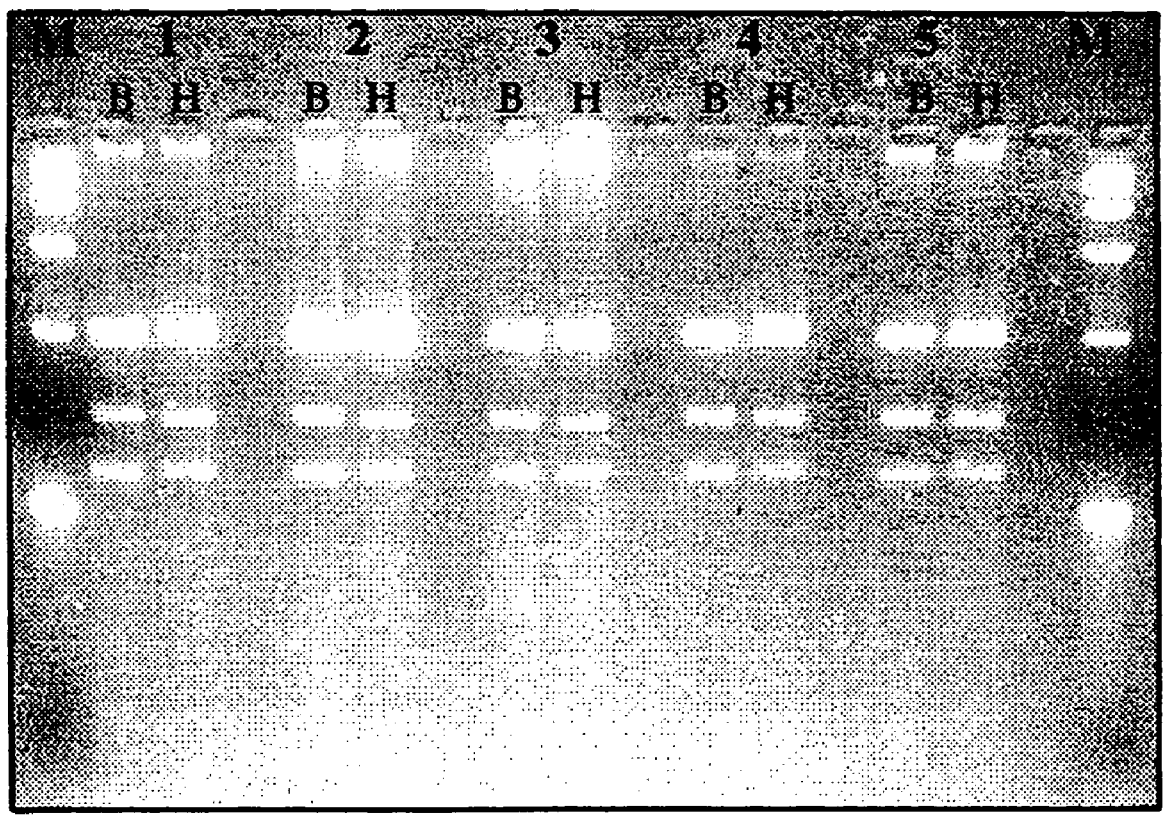

FIG. 3: Agarose gel electrophoresis of DNA fragments obtained by digestion of DNA fragments amplified from the porcine αMSH-R gene with BstUI (lanes labelled B) or HhaI (lanes labelled H). Lanes labelled M contain DNA markers of 50, 150, 300, 500, 750, 1000 bp. The other samples were derived from:

| | |
|---|---|
| 1. | Retailer 1. Skin |
| 2. | Retailer 1. Fat |
| 3. | Retailer 1. Muscle |
| 4. | Retailer 2. Fat |
| 5. | Retailer 2. Muscle |

Figure 4:
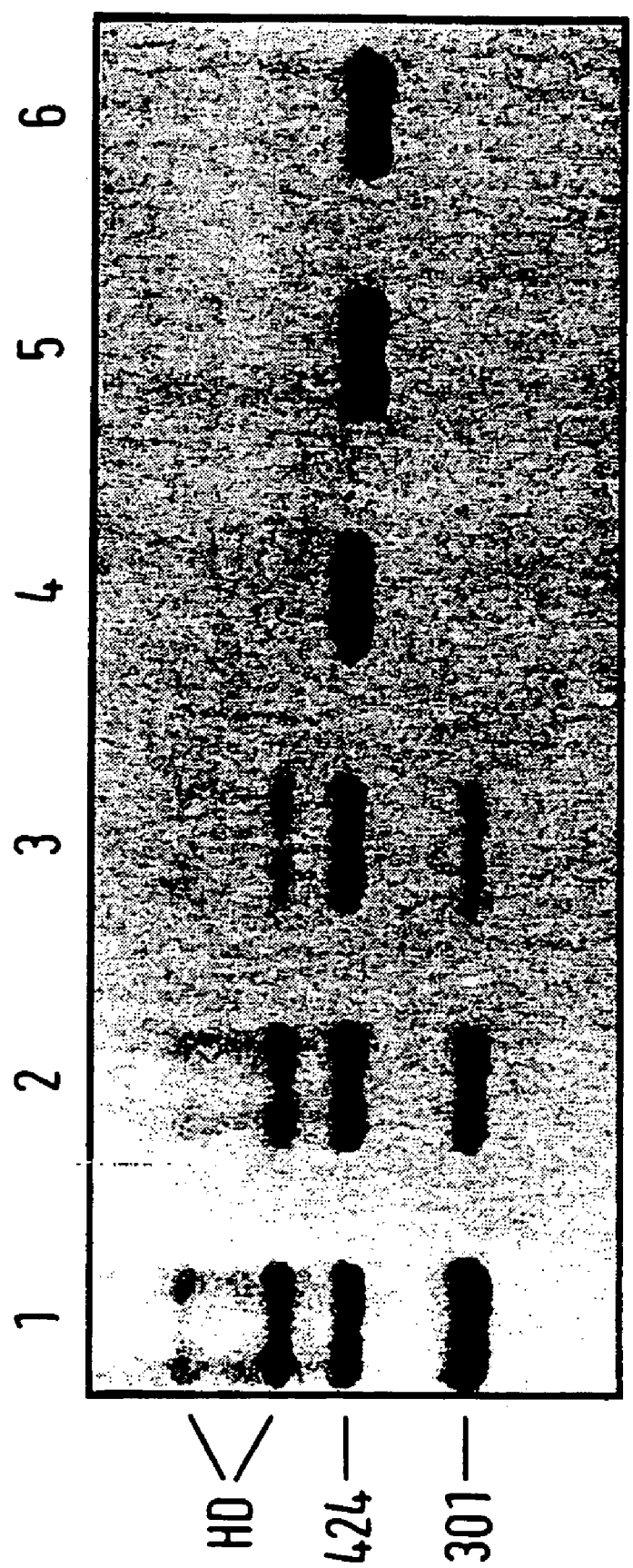

FIG. 4: Electropherogram (4% agarose) showing RT-PCR products of KIT exon 16-19 with the primers KIT1F and KIT7R. The samples 1-3 and 4-6 are Swedish Large White and Hampshire pigs respectively. The size difference between the 424 and 301 bp fragments is due to lack of exon 17 in the latter fraction. The two upper bands of the Yorkshire pigs were interpreted as heteroduplexes (HD).

FIG. 5: A 48 bp sequence is shown comprising 21 bp of KIT exon 17 and 27 bp of KIT intron 17. The position of the intron/exon border is marked with a vertical line and the splice site mutation (nt1$^{G \rightarrow A}$) indicated with a vertical arrow. Identical bases in alleles I$^P$ and i are marked with a dot.

Figure 6C:
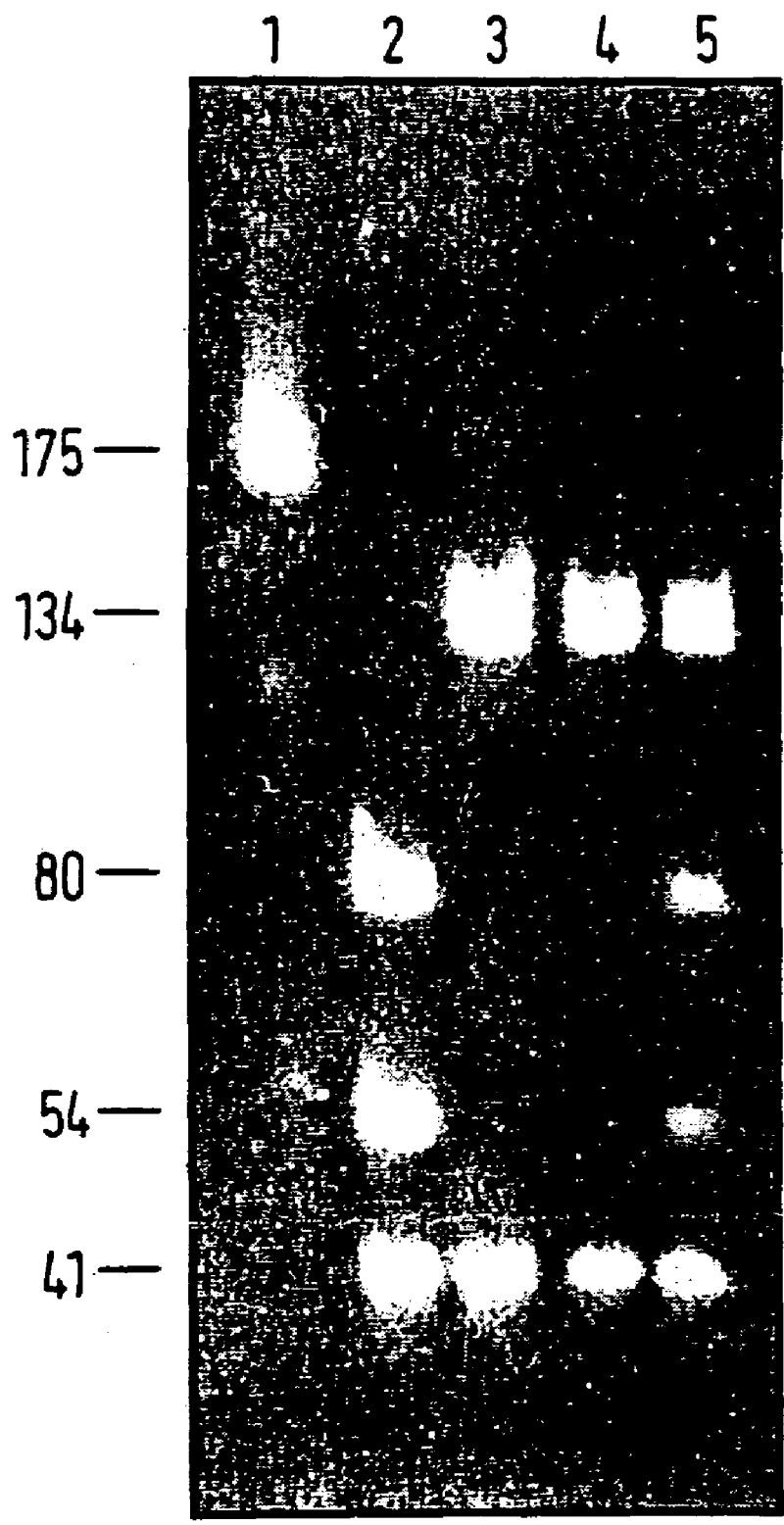

FIG. 6: NlaIII PCR RFLP test used to detect the presence of a splice site mutation in intron 17 of the KIT gene. FIG. 6A shows the position of two NlaIII recognition sites within the PCR product amplified using primer pair KIT21 and KIT35. All distances are given in base pairs. FIG. 6B shows the size of fragments which result following NlaIII digestion of either normal KIT or splice mutant KIT. FIG. 6C illustrates use of the PCR RFLP test. Lane 1 shows the KIT21/KIT35 amplified fragment undigested. Digestion was performed on PCR products amplified from, in Lane 2: a clone which contains the splice site mutation; Lane 3: a clone which contains the normal splice site sequence; Lane 4: genomic DNA from a coloured pig; Lane 5: genomic DNA from a white pig. Fragment sizes are given in base pairs.

Figure 7:
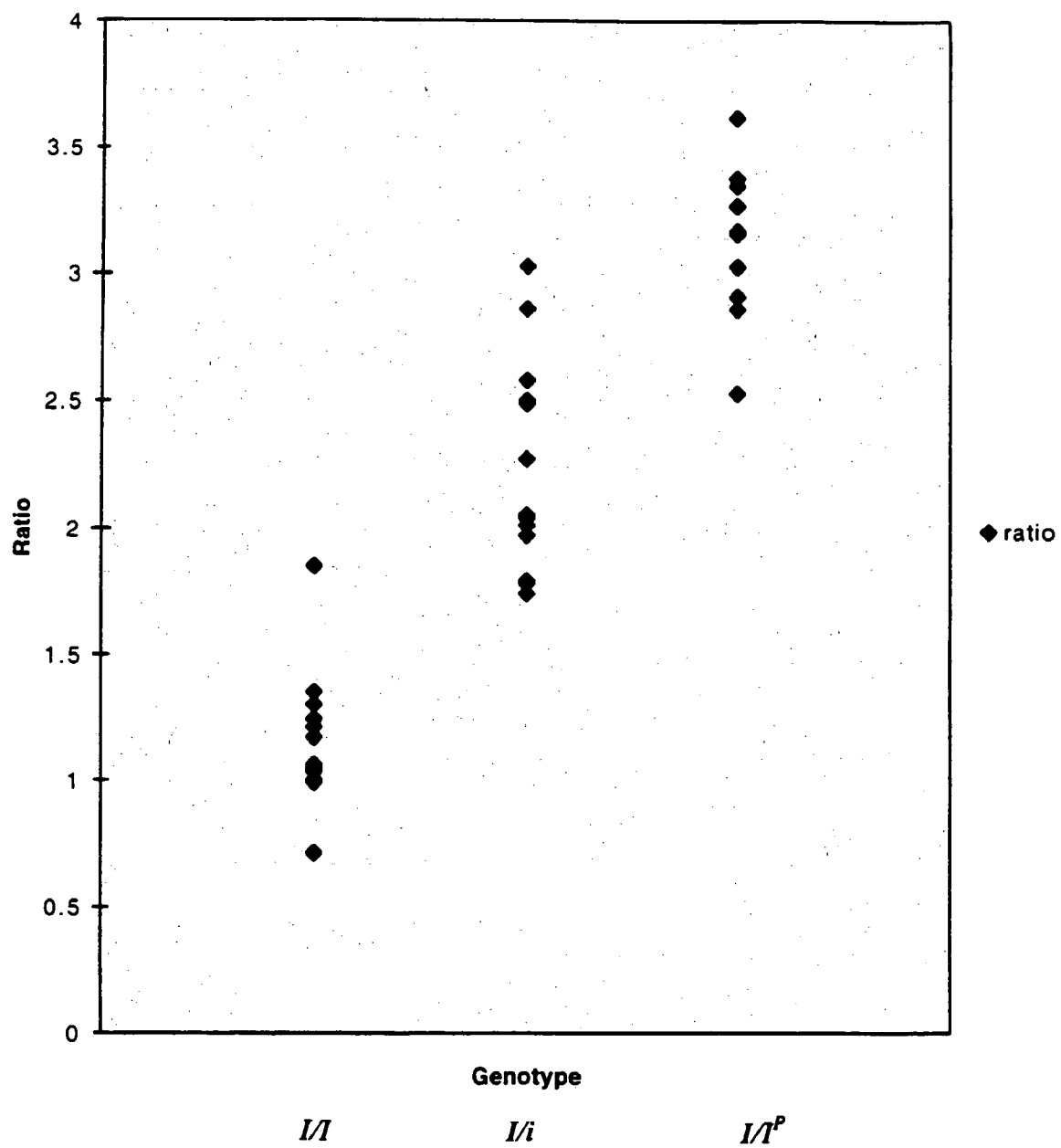

FIG. 7: Comparison of the ratio of normal to splice mutant KIT for three classes of genotype.

Figure 8:
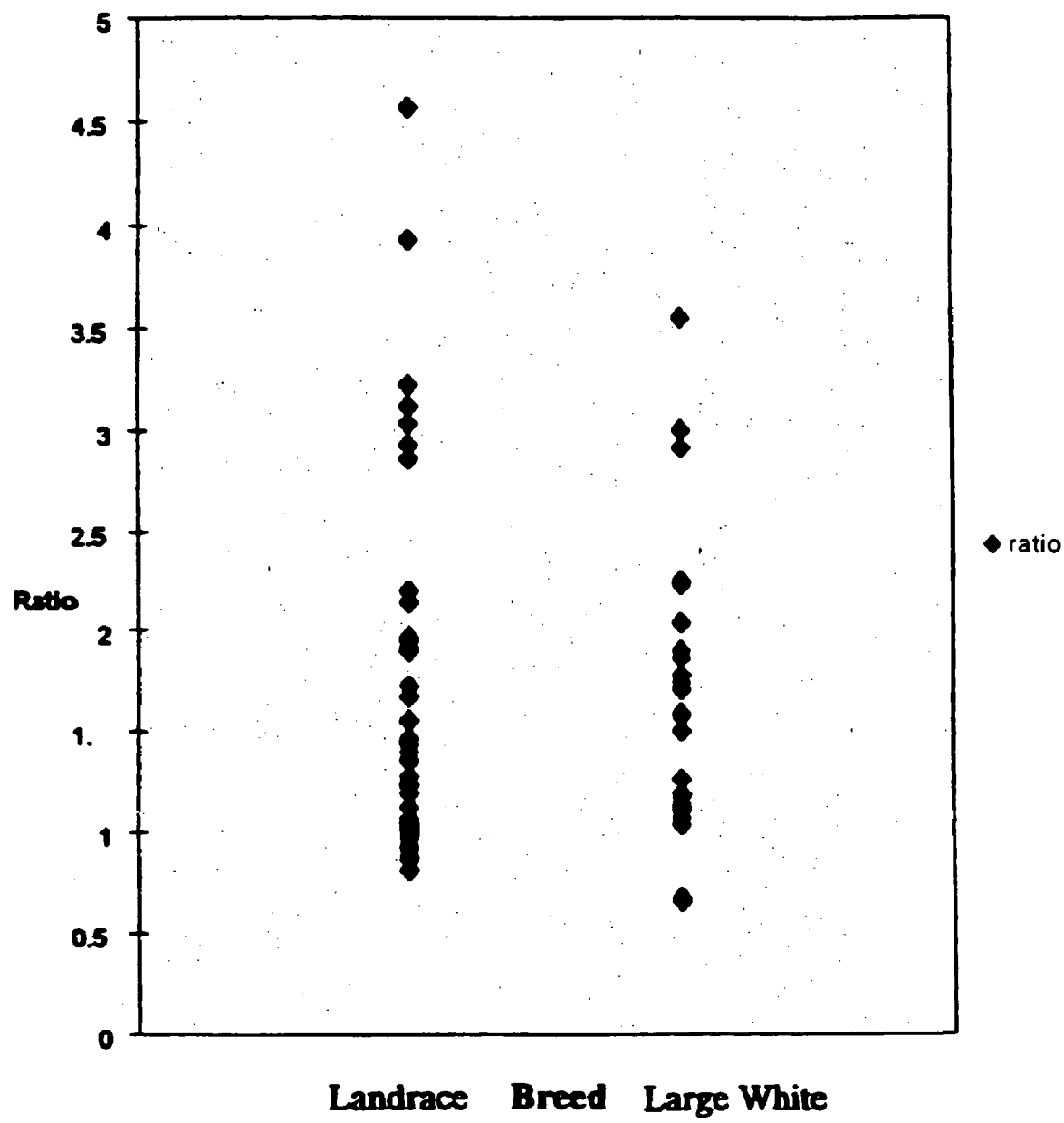

FIG. 8: Comparison of the ratio of normal to splice mutant KIT for two breeds of pig.

Figure 9:
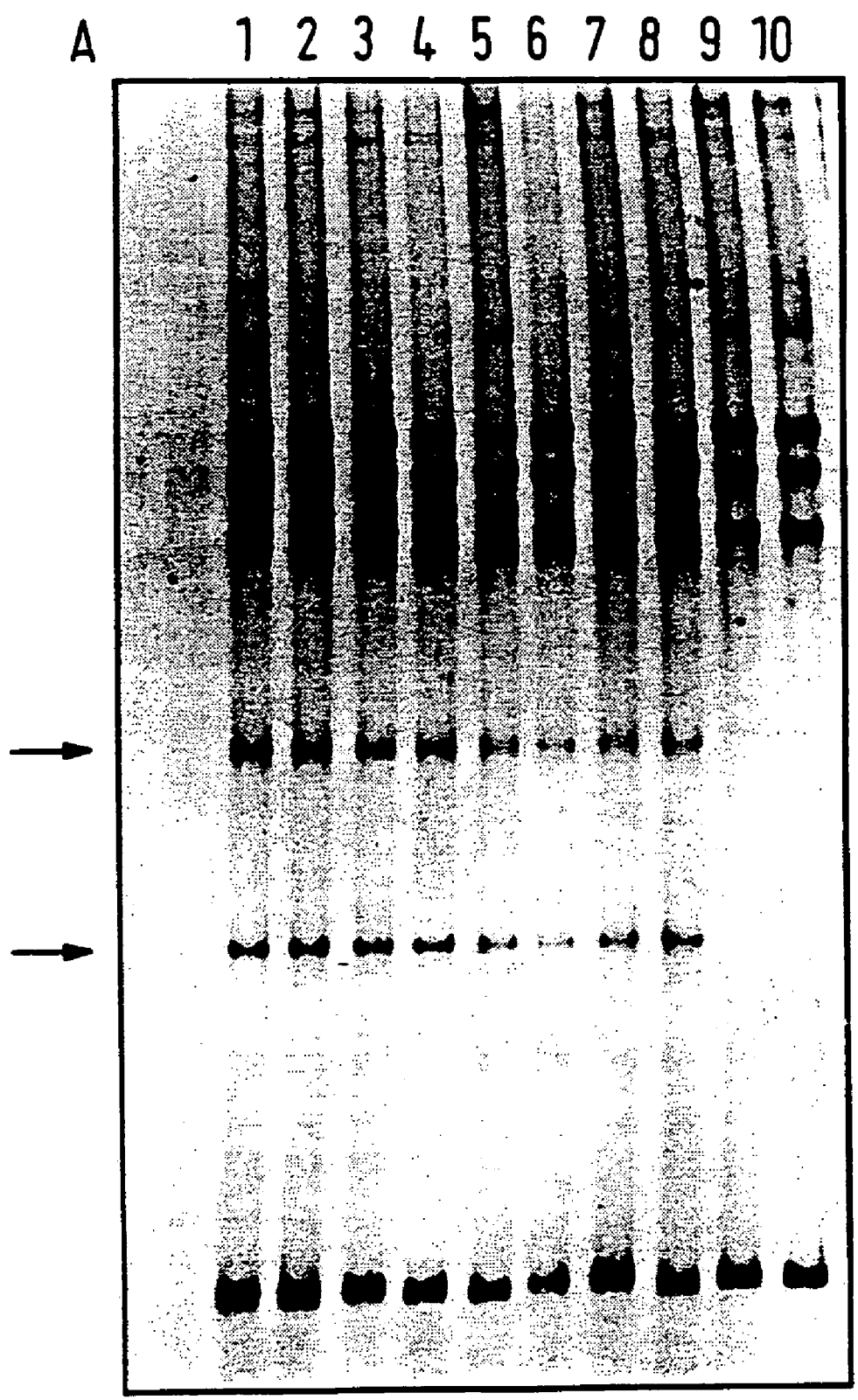

FIG. 9: SSCP analysis of the KIT gene in Swedish Landrace (lanes 1-8) and Wild Boar (lanes 9 & 10) breeds. The two polymorphic bands are indicated.

FIG. 10: Nucleotide sequence of the porcine KIT cDNA from an animal of the Hampshire breed. The sequence is numbered with the first nucleotide of the N terminal methionine codon taken as 1.

Figure 11:
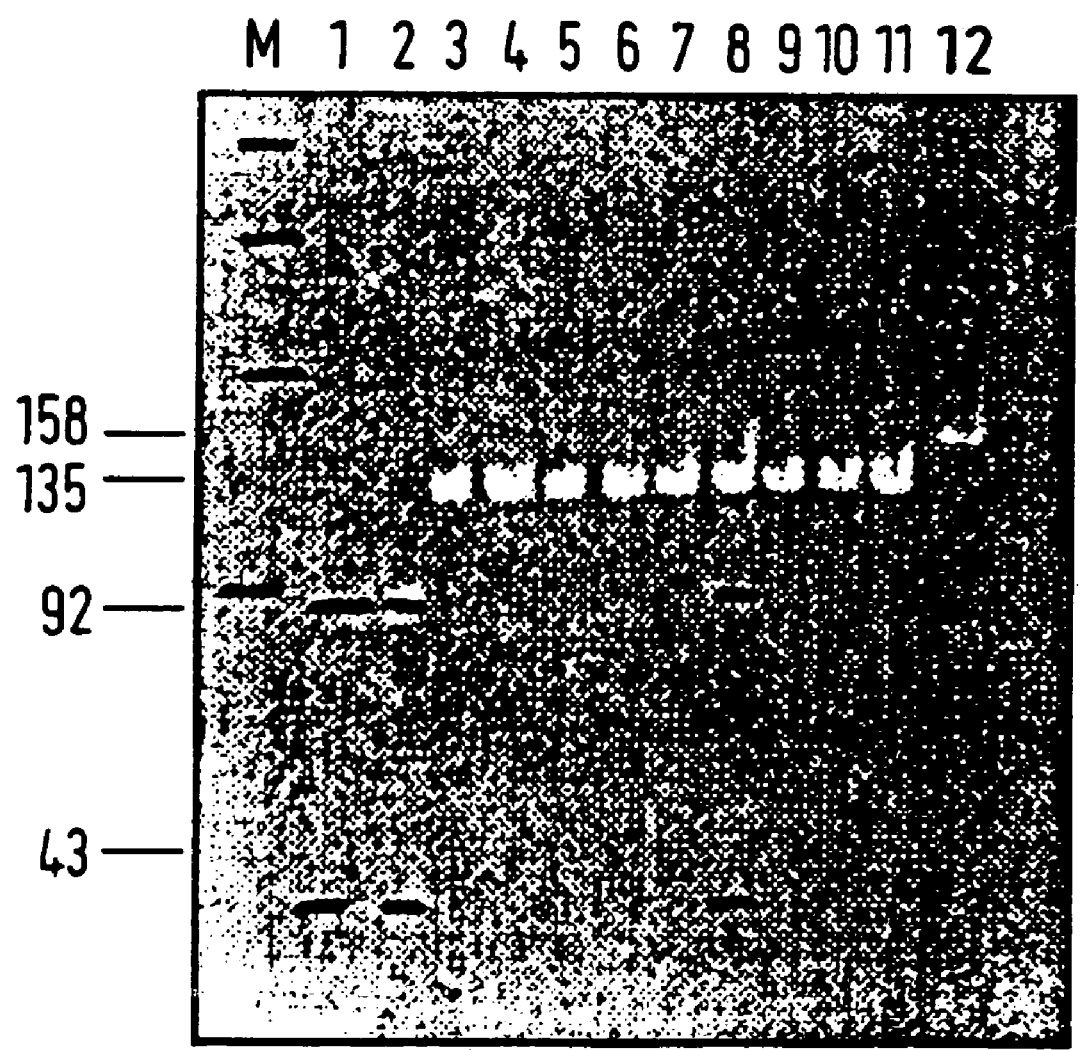

FIG. 11: Polyacrylamide gel electrophoresis of PCR-RFLP analysis of KIT gene at polymorphic nucleotide 2678 in a number of animals. Lanes: 1 & 2, Hampshire Wild Boar respectively, both homozygous for the C at position 2678. Lanes 3-7 and 9 & 10, unrelated Large White sows all homozygous for T at position 2678. Lane 11, a Pietrain, homozygous for T at this position and lane 8 a Large White sow heterozygous for C and T. Lane 12 contains undigested PCR product and lane M DNA size standards.

FIG. 12: Nucleotide sequence of the 3' end of the porcine αMSHR coding region and adjacent 3' untranslated region. The TGA stop codon is highlighted in bold, the primer binding sites for EPIG14 is shown in italics. Numbering is based on the system using in FIG. 1a in which nucleotide 1 is the A of the ATG initiation codon of the Wild Boar sequence. Bases in common with the European Wild Boar are marked with a dash. Missing bases are marked with a.

EXAMPLES

Example 1

Determination of the Sequence of the αMSHR Gene

The DNA sequence of the porcine αMSHR gene was determined through the DNA sequencing of a combination of PCR products and cloned portions of porcine DNA.

Preparation of Template DNA for PCR

DNA can be prepared from any source of tissue containing cell nuclei, for example white blood cells, hair follicles, ear notches and muscle. The procedure here relates to blood cell preparations; other tissues can be processed similarly by directly suspending material in K buffer and then proceeding from the same stage of the blood procedure. The method outlined here produces a cell lysate containing crude DNA which is suitable for PCR amplification. However, any method for preparing purified, or crude, DNA should be equally effective.

Blood was collected in 50 mM EDTA pH 8.0 to prevent coagulation. 50 µl of blood was dispensed into a small microcentrifuge tube (0.5 ml Eppendorf or equivalent). 450 µl of TE buffer was added to lyse the red blood cells (haem groups inhibit PCR) and the mix vortexed for 2 seconds. The intact white and residual red blood cells were then centrifuged for 12 seconds at 13,000 g in a microcentrifuge. The supernatant was removed by gentle aspiration using a low pressure vacuum pump system. A further 450 µl of TE buffer was then added to lyse the remaining red blood cells and the white blood cells collected by centrifugation as before. If any redness remained in the pellet, this process was repeated until the pellet was white. After removal of the last drop of supernatant from the pelleted white blood cells, 100 µl of K buffer containing proteinase K was added and the mixture incubated at 55 degrees C. for 2 hours. The mixture was then heated to 95-100 degrees C. for 8 minutes and the DNA lysates stored at −20 degrees C. until needed.

| Reagents | |
|---|---|
| T.E. Buffer: | 10 mM TRIS-HCl pH 8.0 |
| | 1 mM EDTA |
| K Buffer: | 50 mM KCl |
| | 10 mM TRIS-HCl pH 8.3 |
| | 2.5 mM MgCl2 |
| | 0.5% Tween 20 |

PCR to Produce DNA Sequencing Template

The αMSHR gene was amplified for sequence analysis using three primer pairs.

```
Primers MSHR Forward Primer 1:        (SEQ ID NO:9)
(5'-TGT AAA ACG ACG GCC AGT RGT GCC TGG AGG TGT CCA
T-3'); and MSHR Forward Primer 5:                (SEQ ID NO:10)
(5'-CGC CCA GAT GGC CGC GAT GGA CCG-3')
``` amplify a 428 bp fragment from the 5' half of the gene.

```
Primers MSHR Forward Primer 2:        (SEQ ID NO:3)
(5'-CGG CCA TCT GGG CGG GCA GCG TGC-3'); and αMSHR Reverse Primer 2:               (SEQ ID NO:4)
(5'-GGA AGG CGT AGA TGA GGG GGT CCA-3')
``` amplify a 405 bp fragment the 3' half of the gene.

As these two fragments are non-overlapping a third primer pair

```
αMSHR Forward Primer 4                (SEQ ID NO:11)
(5'-TGC GCT ACC ACA GCA TCG TGA CCC TGC-3'); and αMSHR Reverse Primer 4                (SEQ ID NO:12)
(5'-GTA GTA GGC GAT GAA GAG CGT GCT-3')
``` were used to amplify a 98 bp fragment which spans the 50 bp gap. PCR was carried out on a DNA thermal cycler (Perkin Elmer 9600) in a total volume of 20 µl containing 25 ng genomic DNA, 1.0 mM MgCl2, 50 mM KCl, 10 mM Tris-HCl, pH 8.3, 200 (M dNTPs, 0.5 U AmpliTaq Gold (Perkin Elmer) and 10 pmol of both forward and reverse primer. To activate AmpliTaq Gold, initial heat denaturation was carried out at 94 degrees C for 10 minutes followed by 32 cycles each consisting of 45 sec at 94 degrees C, 45 sec at 53 degrees C and 45 sec at 72 degrees C. The final extension lasted for 7 min at 72 degrees C. PCR products were cloned into vector pUC18 using the SureClone ligation kit (Pharmacia).

Preparation of Plasmid DNA

Plasmid DNA was purified from overnight bacterial culture using the Jetstar plasmid midi kit 50 (Genomed) and the resulting DNA diluted to 150 ng/µl.

Sequencing of Plasmid DNA

Cloned plasmid inserts were sequenced using dye primer chemistry. Each cycling reaction was prepared with template and ready reaction mix containing fluorescently labelled M13 forward or reverse primer as described in the ABI Prism protocol P/N 402113 (Perkin Elmer). Cycling and sample pooling was performed using a Catalyst 800 Molecular Biology Workstation (ABI) following the instruments user manual (Document number 903877, Perkin Elmer). The resulting extension products were purified, loaded and analysed using the 377 ABI Prism DNA sequencer as described by the instrument protocol (Perkin Elmer protocol P/N 402078).

Dye Terminator Sequencing of PCR Products

Dye terminator DNA sequencing requires purification of PCR product free from excess dNTPs and residual primers. This was achieved by passage of the template DNA through QiaQuick spin columns (Qiagen) before the purified DNA was diluted to 15 ng/µl. Dye terminator cycle sequencing was performed using AmpliTaq DNA polymerase FS in accordance with the ABI Prism protocol P/N 402078 (Perkin Elmer). Cycle sequencing reactions were performed in a total reaction volume of 10 µl. This comprised 1.6 pmole of either the forward or reverse primer used to amplify the target fragment from genomic DNA, 20 ng of purified template DNA and terminator ready reaction mix (Perkin Elmer) which contains each of four dye terminators, dNTPs, Tris-HCl (pH 9.0), MgCl2, thermal stable pyrophosphate and AmpliTaq DNA polymerase FS. Cycle sequencing was performed with a GeneAmp 9600 machine (Perkin Elmer) over 25 cycles, each consisting of 10 sec at 96 degrees C., 5 sec at 50 degrees C. and 4 min at 60 degrees C. Extension products were purified for gel separation using ethanol precipitation, loaded and run on a 377 ABI Prism DNA sequencer as described by the instrument protocol (Perkin Elmer protocol P/N 402078).

Results

The partial coding region DNA sequence of the porcine αMSHR gene sequence from a number of pig breeds is given in FIG. 1a combined with sequence determined in example 22. The derived amino acid sequence is shown in FIG. 1b.

Example 2

PCR-RFLP Based Discrimination of Alleles at the E Locus

DNA Preparation for PCR

As in example 1.

PCR

Reactions were set up in a 20 µl reaction volume in thin walled 0.25 ml tubes (Perkin Elmer) with the following components:

| | |
|---|---|
| 20 µl reaction volume: | |
| 2 µl template DNA | |
| 1.5 mM MgCl2 | |
| 200 µM each dNTP, | |
| 3 pM each of forward and reverse primers | |
| 0.5 U AmpliTaq Gold (Perkin Elmer) | |

MSHR Forward primer 3 sequence:    (SEQ ID NO:5)
5' GCA CAT CGC CCG GCT CCA CAA GAC 3'

MSHR Reverse primer 3 sequence:    (SEQ ID NO:6)
5' GGG GCA GAG GAC GAC GAG GGA GAG 3'

The reaction tubes were placed on a Perkin Elmer 9600 thermal cycler preheated to 94 degrees C. and PCR carried out according to the regime below:—

| Initial denaturation step of 94° C. for 10 min. | |
| --- | --- |
| 33 cycles: | 94° C. - 45 secs |
|  | 53° C. - 45 secs |
|  | 72° C. - 45 secs |

The last cycle is followed by a final elongation of 72 degrees C. for 7 min. Samples are stored at 4 degrees C. until required.

Restriction Enzyme Digestion and Electrophoresis

The PCR amplification product is 148 bp in length. To test for polymorphism in the amplified products the reaction is split into two aliquots of 10 µl each of which is digested with HhaI (GIBCO-BRL) or BstUI (New England Biolabs). The reactions are set up and incubated as below:

| BstUI digest | HhaI digest |
| --- | --- |
| 10 µl amplified DNA | 10 µl amplified DNA |
| 2.5µ BstUI | 2.5µ HhaI |
| 60 degrees C. 60 minutes | 0.5 µl 10× React 2 buffer (GIBCO-BRL) |
|  | 37 degrees C. 60 minutes |

Following digestion, 2 µl of loading dye is added to each reaction (100 mM Tris pH8.0, 100 mM Boric Acid, 1 mM EDTA, 50% (v/v) glycerol, 0.02% w/v Orange G) and the mixes loaded on a 4% agarose gel (3% NuSieve/1% Seakem, FMC Bioproducts) in 0.5×TBE (44.5 mM Tris pH8.0, 44.5 mM boric acid and 0.5 mM EDTA) and electrophoresed for 1 hour at 150 v.

Products are visualised by ethidium bromide staining.

Results

BstUI and HhaI digestion each result in bands of 61 and 87 bp. The relationship of digestion to the possible allele is as shown in the table below:

Relationship of Restriction Digest Profiles to Individual Allele at the E Locus

| Allele | Digestion with BstUI | Digestion with HhaI |
| --- | --- | --- |
| $E^+/E^p/E^h$ | Yes | Yes |
| $E^m$ | No | Yes |
| e | No | No |

If the uncut alleles are designated as allele 1 and the alleles digesting with each enzyme as allele 2 the various genotypes will be as shown in the table below:

| Actual E genotypes and associated scores | | |
| --- | --- | --- |
| Genotype | BstUI | HhaI |
| $E^m/E^m$ | 1/1 | 2/2 |
| $E^m/E^p$ or $E^m/E^+$ | 1/2 | 2/2 |
| $E^m/e$ | 1/1 | 1/2 |
| $E^p/E^p$ or $E^p/E^+$ or $E^+/E^+$ | 2/2 | 2/2 |
| $E^p/e$ or $E^+/e$ | 1/2 | 1/2 |
| e/e | 1/1 | 1/1 |

Note:
The results for animals carrying the allele $E^h$ will be the same as those carrying $E^p$.

Figure 2:
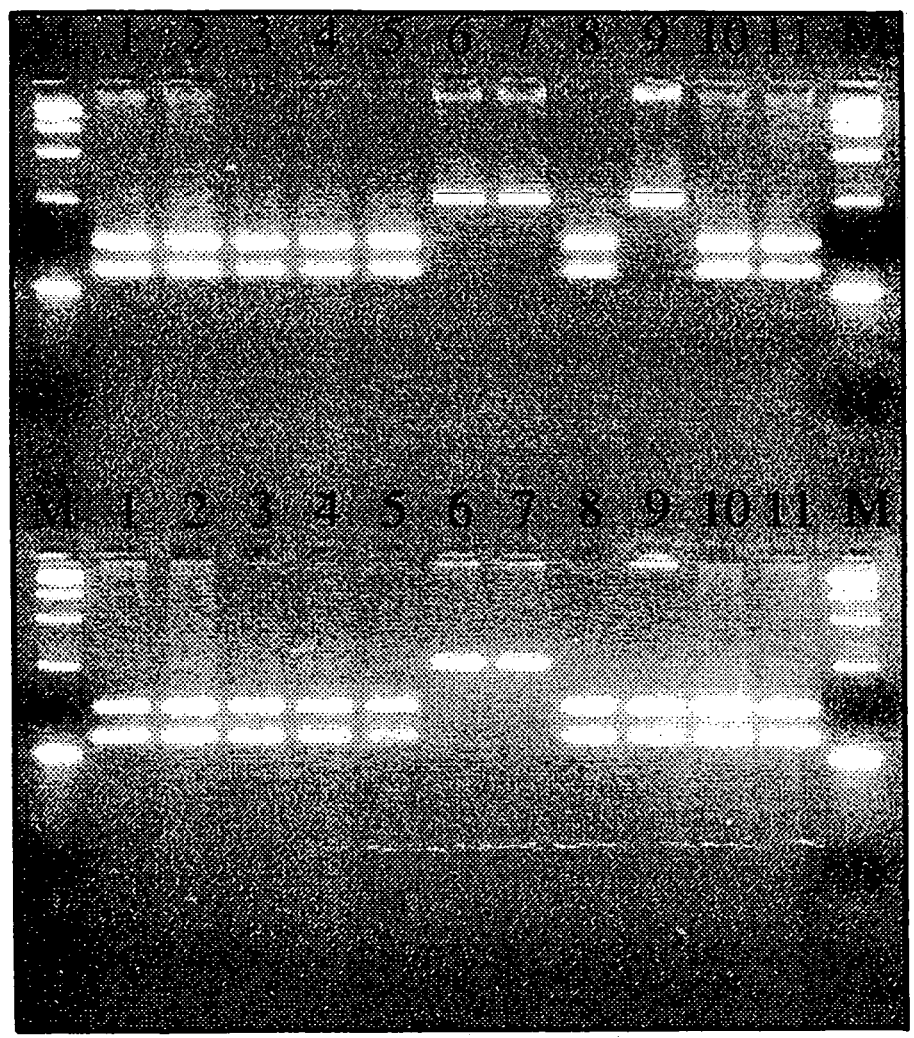

Samples were prepared from a number of pigs and tested according to the above protocol. The results are shown in the table below and FIG. 2 illustrates the patterns seen upon electrophoresis.

E Genotypes Determined for a Range of Breeds Using the BstUI/HbaI Digestion System

| Breed | No Tested | Genotype (see note 1) | αMSHR type BstUI | HhaI |
| --- | --- | --- | --- | --- |
| Hampshire | 9 | $E^h/E^h$ | 2/2 | 2/2 |
| Large White | 4 | $E^p/E^p$ | 2/2 | 2/2 |
| Landrace | 1 | $E^p/E^p$ | 2/2 | 2/2 |
| Pietrain | 3 | $E^p/E^p$ | 2/2 | 2/2 |
| Berkshire | 2 | $E^p/E^p$ | 2/2 | 2/2 |
| Bazna | 4 | $E^p/E^m$ | 1/2 | 2/2 |
|  |  | $E^m/E^m$ | 1/1 | 2/2 |
| Duroc | 4 | e/e | 1/1 | 1/1 |
| Meishan | 3 | $E^m/E^m$ | 1/1 | 2/2 |

Note 1.
The genotype cannot be distinguished from $E^+$ or $E^h$ in this particular test.

As can be seen from the results above the genotypes determined fit with those expected from the sequencing data given in FIG. 1a for Hampshire, Large White, Meishan and Duroc. The additional breeds typed here show the genotypes expected from their phenotype and descriptions in published literature (Ollivier and Sellier, Ann. Génét. Sél. Anim., 14: 481-544, (1982)). The Pietrain is a white breed with black patches of varying extent and has long been considered to be $E^p$ (in agreement with the result here). The Berkshire, originally a spotted breed, is now a mainly black animal with white 'socks' again generally considered to be $E^p$ as was found here. The Landrace is a white animal due to it carrying the dominant white allele at the I locus, however its genotype at the E locus has been shown to be $E^p$ from classical breeding studies. Once again this is in agreement with the results obtained here. The Bazna is a Romanian breed having black base colour with a white belt. It was developed from the Berkshire and Mangalitza, a Hungarian breed with a number of colour variations including black (Porter, Pigs, a handbook to breeds of the world, publ: Helm Information, ISBN 1-873403-17-8 (1993)). The ancestry of the Bazna being based upon a black breed potentially carrying a similar allele to the Meishan, $E^m$, and the Berkshire carrying $E^p$, is in agreement with the alleles found to be present in the breed in this work.

Example 3

Validation of Source Breed, of Retail Meats

DNA Preparation

DNA was prepared from different parts of pork chops from two separate retailers. The DNA was prepared from skin (1 retailer only), fat and muscle using the Promega Wizard Genomic DNA preparation kit according to the manufacturers instructions. Approximately 4 mm³ of each tissue was cut into small fragments for the extraction.

PCR and Restriction Digest Analysis

This was carried out exactly as in example 2.

Results

The results are shown in FIG. 3. It can be seen that DNA extracted from a range of tissue types can be utilised for this DNA based test with results being obtained here for muscle, fat and skin. The genotype of the pig with regard to the (MSHR gene can then be determined. In this case the material from both retailers was derived from an animal of test type BstUI ½ and HhaI ½ using the nomenclature as in example 2. This translates into genotype $E^p$/e or $E^+$/e. Based on our current knowledge of the distribution of the alleles in commercial pig breeds the conclusion can be drawn that both source animals contain genetic material derived from the Duroc.

Example 4

Validation of Source Breeds of Processed Meat Samples

Method

DNA was prepared from heat treated meat samples according to the method of Meyer et al. (Journal of AOAC International, 78 1542-1551). Meat samples were minced with a scalpel and 0.3 g transferred to a sterile 1.5 ml eppendorf tube containing 430 μl of extraction buffer (10 mM Tris-HCl pH 8.0, 150 mM NaCl, 2 mM EDTA, and 1% w/v sodium dodecyl sulphate). Fifty microlitres of 5M guanidine hydrochloride and 20 μl of 20 mg/ml proteinase K (Boehringer) were added and mixed by inversion followed by incubation at 57° C. for 3 h. After digestion samples were centrifuged for 10 min at 13,000×g, and 450 μl of the aqueous phase added to 1 ml Wizard DNA purification resin (Promega). The mixture was mixed by gentle inversion and following the Wizard DNA clean-up procedure carried out according to the manufacturers instructions the purified DNA was eluted with 50 μl of 70° C. water. 1 μl of a 1:10 dilution was then used as template in a 10 μl PCR.

PCR was carried out as described in the previous example.

Results

Meat samples from a Large White based line and a Duroc based line heated at 80° C. for 30 mins could be differentiated on the basis of their genotype at the E locus with the Large White samples giving a pattern characteristic of the $E^P$ allele and the Duroc samples a pattern characteristic of the e allele.

Example 5

Validation of Source Breed, of Semen

Genomic DNA was isolated from porcine semen. 1 ml of semen was centrifuged for 2 min at 13,500×g and the supernatant removed. 1 ml of 2×SSC was added and the mix vortexed to resuspend the sperm. The mix was then centrifuged as before and the supernatant removed. 400 μl of 0.2M NaOAc pH 7.0 was added and the mix vortexed followed by the addition of 34 μl of 6-mercaptoethanol. The mixture was incubated at 40° C. for 30 min followed by the addition of 100 μl of 10% w/v sodium dodecyl sulphate and 50 μl of 15 mg/ml Proteinase K (Boehringer) and further incubation at 40° C. for 3 hours. 500 μl phenol equilibrated with Tris-HCl pH 8.0 was added and the mix vortexed twice followed by centrifugation at 13,500×g for 4 min. 400 μl of the aqueous phase was removed and 800 μl of ethanol added. DNA was allowed to precipitate for 5 min at room temperature followed by centrifugation at 13,500×g for 5 min. The pellet was washed with 800 μl 70% ethanol v/v and air dried followed by resuspension in 200 μl of Wizard DNA resuspension buffer (Promega). 1 μl of a 1/10 dilution was used in a 10 μl PCR PCR was carried out as described in example 2.

Results

Semen form a Hampshire based line and a Duroc based line could be differentiated on the basis of their genotype at the E locus with the Hampshire samples giving a pattern characteristic of the $E^h$ allele and the Duroc samples a pattern characteristic of the e allele.

Example 6

Discrimination of Allele $E^+$ from Alleles $E^p$/$E^h$

DNA preparation

DNA was prepared as described in example 1.

PCR

Reactions were set up in a 20 μl reaction volume in thin walled 0.25 ml tubes (Perkin Elmer) with the following components:

| 10 μl reaction volume: |
| --- |
| 2 μl template DNA |
| 2.5 mM MgCl₂ |
| 200 μM each dNTP, |
| 5 pmol each of forward and reverse primers |
| 0.5 U AmpliTaq Gold (Perkin Elmer) |

```
Forward primer sequence:              (SEQ ID NO:13)
5' CTG CCT GGC CGT GTC GGA CCT G 3'

Reverse primer sequence:              (SEQ ID NO:14)
5' CTG TGG TAG CGC AGC GCG TAG AAG 3'.
```

The reaction tubes were placed on a Strategene Robocycler and PCR carried out according to the regime below:—

| Initial denaturation step of 94° C. for 10 min. | |
| --- | --- |
| 30 cycles: | 94° C. - 60 secs |
| | 61° C. - 60 secs |
| | 72° C. - 60 secs |

The last cycle is followed by a final elongation of 72° C. for 7 min. Samples are held at 6° C. until required.

Restriction Enzyme Digestion and Electrophoresis

The PCR amplification product is 228 in length. To test for polymorphism in the amplified products the reaction is digested with BspHI (New England Biolabs). The reactions are set up and incubated as below:

| BspHI digest |
| --- |
| 10 µl amplified DNA |
| 1 ul 10x React 2 (NEB New England Biolabs) |
| 0.5 µl deionised water |
| 5 units BstUI |
| 37° C. 60 minutes |

Following digestion, 2 µl of loading dye is added to the reaction (100 mM Tris pH8.0, 100 mM Boric Acid, 1 mM EDTA, 50% (v/v) glycerol, 0.02% w/v Orange G) and the mix loaded on a 4% agarose gel (3% NuSieve/1% Seakem, FMC Bioproducts) in 0.5×TBE (44.5 mM Tris pH8.0, 44.5 mM boric acid and 0.5 mM EDTA) and electrophoresed for 1 hours at 150 v.

Products are visualised by ethidium bromide staining.

Results

BspHI digestion each result in bands of 124 and 104 bp. The relationship of digestion to the possible allele is as shown below:

Relationship of Restriction Digest Profiles to Individual Alleles at the E Locus

| Allele | Digestion with BspHI |
| --- | --- |
| $E^h/E^p$ | Yes |
| $E^+$ | No |

Samples were prepared from a number of pigs and tested according to the above protocol and the results are shown below:

E Genotypes Determined for a Range of Breeds Using the BspHI Digestion System

| Breed | No Tested | Genotype (see note 1) | Number |
| --- | --- | --- | --- |
| Wild Boar × Swedish Landrace | 3 | $E^p/E^+$ | 3 |
| Large White | 4 | $E^p/E^p$ | 4 |
| Landrace | 1 | $E^p/E^p$ | 1 |
| Pietrain | 3 | $E^p/E^p$ | 3 |

Note 1.
Where the genotype $E^p$ is listed this cannot be distinguished from $E^h$ in this particular test.

Example 7

Discrimination of Cattle Products by Breed

DNA was prepared from cattle muscle samples as described in example 4. PCR was then carried out in a 100 µl reaction using the primer pair:

5'-TGAGGTAGGAGAGTTTTGGG-3' (SEQ ID NO:15) and
5'-TCGAAATTGAGGGGAAGACC-3' (SEQ ID NO:16)

as described in Kambadur et al. *Genome Research* 7: 910-915 (1997) at a concentration of 500 nM with other reaction components being 2.5 mM $MgCl_2$, 200 µM dNTPs, 50 mM KCl, 10 mM Tris-HCl pH 8.3, 5 units AmpliTaq Gold (Perkin Elmer). 1 µl of bovine genomic DNA was used as template. Denaturation was carried out for 12 min at 94° C. followed by 30 cycles of 94° C. for 1 min, 55° C. for 1 min, 72° 1.5 min followed by 5 min at 72° C. Following PCR 2.0 µl of loading dye (44.5 mM Tris pH 8.0, 44.5 mM boric acid, 0.5 mM EDTA, 50% w/v glycerol, 0.02% w/v Orange G) was added to 10 µl of product and analysis carried out by electrophoresis on a 2% agarose gel prepared in 0.5×TBE buffer (44.5 mM Tris pH 8.0, 44.5 mM boric acid, 0.5 mM EDTA) for 1 hour at 100 V.

The remainder of the PCR was analysed for DNA sequencing using ABI dye terminator chemistry as described in example 1.

Result

| Bovine myostatin DNA polymorphisms and related phenotype | | | |
| --- | --- | --- | --- |
| Breed | Phenotype | nt position 941 | length PCR product (bp) |
| Belgian Blue | Double muscle | G | 482 |
| Piedmontese | normal | A | 493 |
| Holstein-Friesian | Double muscle | G | 493 |

Example 8

RT-PCR of Porcine KIT Exon 16-19 i. mRNA Purification from Blood Samples

Fresh blood samples were collected in citrate tubes from coloured Hampshire pigs and Large White pigs. Leukocytes were isolated from 5 ml blood using Ficoll 100 (Pharmacia Biotech). Isolation of mRNA from leukocytes was then carried out using the Quickprep Micro mRNA purification kit (Pharmacia Biotech). The mRNA was stored as a precipitate under ethanol at −70° C. for up to one month before use in reverse transcriptase (RT)-PCR.

ii. RT-PCR of KIT Exon 16-19

First-strand cDNA synthesis was accomplished using the First-Strand cDNA Synthesis kit (Pharmacia Biotech) so that ~100 ng mRNA was randomly primed by 0.1 µg pd(N6) in a total volume of 15 µl. Two µl of the completed first cDNA strand reaction was then directly used per 12 µl PCR reaction by adding 10 µl PCR mix containing 10 pmol each of the mouse/human derived primers KIT1F and KIT7R (5'-TCR TAC ATA GAA AGA GAY GTG ACT C (SEQ ID NO:17) and 5'-AGC CTT CCT TGA TCA TCT TGT AG (SEQ ID NO:18), respectively; Moller et al. 1996, supra), 1.2 µl 10×PCR-buffer (10 mM Tris-HCl, pH 8.3, 50 mM KCl) and 0.5 U of AmpliTaq polymerase (Perkin-Elmer) incubated with an equal amount Taqstart antibody (Clontech) at 25° C. for 5 min to achieve a hot start PCR. The reaction was covered with 20 µl mineral oil and thermocycled in a Hybaid Touchdown machine (Hybaid) with 40 cycles at 94° C. for 1 min, 55-48° C. (touchdown one degree per cycle the first seven cycles and then 48° C. in the remaining cycles) for 1 min and 72° C. for 1 min. After PCR 2 µl loading dye was added to each sample which were then loaded on 4% agarose gel (Nusieve/Seakem 3:1, FMC Bioproducts) and electrophoresed with 100 V for 80 min. Products were visualised by ethidium bromide staining and UV-illumination.

iii. Cloning and Sequencing of RT-PCR-Products

The RT-PCR products representing KIT exon 16-19 were purified by extraction from 2% agarose gels using the QIAEX gel extraction kit (QIAGEN) and cloned into the pUC18 vector using the Sureclone ligation kit (Pharmacia Biotech). Plasmids were isolated using the QIAFilter plasmid Midi kit (QIAGEN). Cloned plasmid inserts were sequenced using dye primer chemistry. Each cycling reaction was prepared with plasmid template DNA and ready reaction mix containing fluorescently labelled M13 forward or reverse primer as described in the ABI Prism protocol P/N 402113 (Perkin Elmer). Cycling and sample pooling were performed using a Catalyst 800 Molecular Biology Workstation (ABI) following the instruments user manual (Document number 903877, Perkin Elmer). The resulting extension products were purified, loaded and analysed using the 377 ABI Prism sequencer as described by the instrument protocol P/N 402078 (Perkin Elmer).

iv Results and Discussion

A 424 bp fragment including KIT cDNA exon 16-19 was amplified from all pigs. The Hampshire pigs did not show any additional products whereas the Large White pigs (eight tested) all showed a 301 bp truncated cDNA fragment (FIG. 4). Sequence analysis revealed the 424 bp fragment was identical in the two breeds whereas the whole exon 17 (123 bp) was missing from the 301 bp fragment. Apparent differences between individuals regarding the relative amounts of these two products may have been caused either by different genotypes containing differing numbers of copies of the KIT gene sequence, individual differences in mRNA expression levels or random RT-PCR effects.

The two upper fragments present in Large white pigs represent heteroduplexes between the 301 and 424 bp fragments (FIG. 2). This was shown by an experiment where these slow migrating fragments were generated by pooling homoduplexes of the 424 and 301 bp which were then heat denatured and cooled to 25° C. Moreover, cloning of the lower heteroduplex fraction of a Large White pig resulted in clones with insert length corresponding to either of the two homoduplexes.

Example 9

PCR Amplification and Sequencing of KIT Exon 17-Intron 17 (5' Splice Site)

i. PCR to Produce DNA Sequencing Template

A 175 bp region including the boundary between exon17 and intron17 of the KIT gene was amplified for sequence analysis using forward primer KIT21 (5'-GTA TTC ACA GAG ACT TGG CGG C-3') (SEQ ID NO:19) and reverse primer KIT35 (5'-AAA CCT GCA AGG AAA ATC CTT CAC GG-3') (SEQ ID NO:20). PCR was carried out on a DNA thermal cycler (Perkin Elmer 9600) in a total volume of 20 µl containing 25 ng genomic DNA, 1.0 mM $MgCl_2$, 50 mM KCl, 10 mM Tris-HCl, pH 8.3, 200 FM dNTPs, 0.5 U AmpliTaq Gold (Perkin Elmer) and 10 pmol of both KIT21 and KIT35 primer. To activate AmpliTaq Gold, initial heat denaturation was carried out at 94° C. for 10 minutes followed by 32 cycles each consisting of 45 sec at 94° C., 45 sec at 55° C. and 45 sec at 72° C. The final extension lasted for 7 min at 72° C. PCR products were cloned into vector pUC18 using the SureClone ligation kit (Pharmacia Biotech).

ii. Preparation of Plamid DNA

Plasmid DNA was purified from overnight bacterial culture using the Jetstar plasmid midi kit (Genomed) and the resulting DNA diluted to 150 ng/µl.

iii. Sequencing of plasmid DNA

DNA was sequenced as in example 8.

iv. Results

A portion of the DNA sequence from exon 17 and intron 17 of the KIT gene was determined and compared between animals with each of these three alleles. FIG. 5 shows that the I allele carries a splice site mutation at position 1 of intron 17. This G to A base substitution is present in one of the two gene copies carried on each chromosome. The base substitution occurs in the invariant GT dinucleotide which characterises 5' exon/intron boundaries. Analysis of the $I^P$ allele showed the splice site mutation was not present in either the normal (KIT 1) or duplicated copy of the gene (KIT2). We have found the splice site mutation is unique to the I alleles, and therefore makes it possible to distinguish the I-KIT2 sequences.

Example 10

Testing for the Presence of the Splice Site Mutation with PCR RFLP

To easily test for the presence of the G to A splice site mutation, restriction endonuclease NlaIII (CATG) was used to exploit the point substitution identified at position 1 of intron 17 (FIG. 5). The NlaIII recognition sites in the fragment amplified from KIT and the expected restriction products are illustrated in FIGS. 6A and 6B respectively.

i. PCR to Produce DNA for RFLP Test

The PCR to produce DNA for RFLP analysis was performed exactly as described in example 9.

ii. Restriction Enzyme Digestion and Electrophoresis

The PCR amplification product is 175 bp in length. To test for polymorphism at position 1 of intron 17, digestion reactions were set up as below:

| | |
|---|---|
| 3.0 µl | PCR amplified DNA |
| 1.0 µl | 10X NEBuffer 4 |
| 0.1 µl | BSA 100 µg/ml |
| 0.1 µl | NlaIII 10 U/µl |
| 5.8 µl | dH2O |

(1×NEBuffer 4 (New England Biolabs) contains 50 mM potassium acetate, 20 mM Tris acetate, 10 mM magnesium acetate and 1 mM DTT). Following incubation at 37° C. for 90 minutes each 10 µl reaction volume had 2 µl of loading dye added and the mix loaded on a 8% native polyacrylamide gel (Protogel, 37.5:1 acrylamide:bisacrylamide, National Diagnostics, Atlanta) in 0.5×TBE (44.5 mM Tris pH 8.0, 44.5 mM boric acid and 0.5 mM EDTA) and electrophoresed for 3 hours at 200V in a vertical slab unit (SE600 Hoefer Scientific Instruments). Products were visualised by ethidium bromide staining.

iii Results

A PCR RFLP protocol was designed to test for the presence of the splice site mutation as the substitution occurs within the recognition site for restriction endonuclease NlaIII. FIG. 6B illustrates that presence of the G to A base substitution at position 1 of KIT intron 17 results in restriction at each of two NlaIII recognition sites within the 175 bp DNA fragment. Following electrophoresis, this results in fragments of sizes 80 bp, 54 bp and 41 bp. Where the splice site mutation is absent however, incubation with NlaIII results in digestion only at recognition site 1. Following electrophoresis this results in fragments of 134 bp and 41 bp. The invariant NlaII recognition site 1 serves as an internal control to ensure complete digestion has taken place. Results of this PCR RFLP analysis are illustrated in FIG. 6C. Analysis was performed on fragments amplified from clones which either carry the splice site mutation (lane 2) or carry the normal splice site sequence (lane 3). Lane 4 shows the result of analysis where DNA amplified from the genomic DNA of a coloured animal was used. Lane 5 shows the resulting bands where a white animal was tested. The test was used to analyse 121 individuals from seven different breeds of pig. The splice site mutation was found only in the 97 animals with the dominant white phenotype (I|- or I*/i) and none of the 24 coloured ($I^P$ or i) examples (see table below). This analysis confirms I and I* to be unique in that they are the only alleles to carry the splice site mutation.

Distribution of the Splice Site Mutation Between Different Breeds and Coat Phenotype

| Breed | Coat Colour | Assumed Genotype[1] | Animals Tested | Normally spliced KIT[2] | Splice Mutation[2] |
|---|---|---|---|---|---|
| Large White | white | I/— | 33 | 33 | 33 |
| Landrace | white | I/— | 56 | 56 | 56 |
| Hampshire | coloured | i/i | 5 | 5 | 0 |
| Duroc | coloured | i/i | 5 | 5 | 0 |
| Pietrain | coloured | i/i | 8 | 8 | 0 |
| Meishan | coloured | i/i | 5 | 5 | 0 |
| Wild Boar | coloured | i/i | 1 | 1 | 0 |
| Wild Boar × Large White | white | I*/— | 8 | 8 | 8 |
| Totals | | | | | |
| | white | I/— | 89 | 89 | 89 |
| | white | I*/— | 8 | 8 | 8 |
| | coloured | i/i | 24 | 24 | 0 |

[1]White animals may be homozygous or heterozygous for the I allele
[2]Presence of the splice site mutation determined by NlaIII PCR RFLP test

Example 11

Quantification of Normal KIT and Splice Mutant KIT (Intron 17 $nt1^{G \to A}$)

As the splice site mutation is present in only one of the duplicated regions of I and not in the duplicated region of $I^P$, the various genotypes can be expected to have the attributes described in the table below:

| Genotype | Copies of Normal KIT | Copies of KIT containing the splice mutation | Ratio of normal KIT to splice mutant KIT |
|---|---|---|---|
| I/I | 2 | 2 | 1:1 |
| I/i | 2 | 1 | 2:1 |
| i/i | 2 | 0 | 2:0 |
| I/$I^P$ | 3 | 1 | 3:1 |
| $I^P$/i | 3 | 0 | 3:0 |

Due to the dominance of allele I, three of the genotypes in the table are carried by white animals and therefore can not be identified by phenotypic characterisation. Quantification of the relative amounts of the normal KIT gene and the splice mutant KIT gene allows the ratio between the two to be calculated, and therefore the genotype of individual animals predicted. This was achieved by quantification of two DNA fragments following NlaIII digestion. The amount of 134 bp fragment, representative of the normally spliced KIT gene, and of 54 bp fragment, representative of the splice mutant KIT, were measured following electrophoresis using GeneScan software.

i. PCR to Produce DNA for Quantification

As described in example 9 section i. The reverse primer KIT35 is labelled with the ABI fluorescent dye FAM at the 5' end.

ii Restriction Enzyme Digestion

As described in example 9 section ii.

iii Electrophoresis and Quantification of DNA Fragments

Following digestion, 0.5 μl of the reaction volume was mixed with 2.5 μl of deionised formamide, 0.5 μl of GS350 DNA standard (ABI) and 0.4 μl blue dextran solution before being heated to 90° C. for 2 minutes and rapidly cooled on ice. Three μl of this mix was then loaded onto a 377 ABI Prism sequencer and the DNA fragments separated on a 6% polyacrylamide gel in 1×TBE buffer for 2 hours at 700 V, 40 nA, 32 W. The peak area of fragments representative to both the normal and splice mutant forms of KIT were quantitated using the GeneScan (ABI) software.

iv. Ratio Calculations

The peak area value of the 134 bp fragment (normal KIT) was divided by twice the peak area value of the 54 bp fragment (splice mutant KIT) in order to calculate the ratio value for each sample.

v. Results

Analysis was performed on animals from the Swedish wild pig/Large White intercross pedigree for which genotypes at I have been determined by conventional breeding experiments with linked markers. FIG. 7 and the table below show the ratio of normal to mutant KIT calculated for animals from each of the three genotype classes, I/I (expected ratio 1:1), I/i (expected ratio 2:1) and I/$I^P$ (expected ratio 3:1). The results are entirely consistent with the expected ratio values and indicate that the three genotype classes can be distinguished using this method.

Ratio of the Two KIT Forms in Different Dominant White
Genotypes in a Wild Pig/Large White Intercross

| Genotype | Phenotype | Expected Ratio (Normal:Mutant) | Observed Ratio (Normal:Mutant) ± SE | Number Tested |
|---|---|---|---|---|
| I/I | white | 1:1 | 1.15 ± 0.075 | 13 |
| I/I$^P$ | white | 3:1 | 3.11 ± 0.084 | 12 |
| I/I | white | 2:1 | 2.23 ± 0.109 | 14 |

FIG. 7 illustrates that the range of ratio values calculated for the two genotypes I/I and I/I$^P$ do not overlap. This enables animals carrying the I$^P$ allele to be identified and the frequency of the allele within different pig breeds determined. Ratio values were calculated for 56 Landrace and 33 Large White animals and the results are shown in FIG. 8. A clearly bimodal distribution is observed with 7 Landrace and 3 Large White individuals having a ratio value of approximately 3 or above, suggesting them to be heterozygous carriers for the I$^P$ allele (genotype I/I$^P$). This means I$^P$ has gene frequency estimates of 6.25% (7/112 chromosomes tested) and 4.5% (3/66 chromosomes tested) within the Landrace and Large White breeds respectively.

Example 12

(i) DNA Preparation

DNA can be prepared from any source of tissue containing cell nuclei, for example white blood cells, hair follicles, ear notches and muscle. The procedure outlined here relates to blood cell preparations; other tissues can be processed similarly by directly suspending material in K buffer and then proceeding from the same stage of the blood procedure. The method outlined here produces a cell lysate containing crude DNA which is suitable for PCR amplification. However, any method for preparing purified, or crude, DNA should be equally effective.

Blood was collected in 50 mM EDTA pH 8.0 to prevent coagulation. 50 µl of blood was dispersed into a small microcentrifuge tube (0.5 ml Eppendorf or equivalent). 450 µl of TE buffer was added to lyse the red blood cells (haem groups inhibit PCR) and the mix vortexed for 2 seconds. The intact white and residual red blood cells were then centrifuged for 12 seconds at 13,000 g in a microcentrifuge. The supernatant was removed by gentle aspiration using a low pressure vacuum pump system. A further 450 µl of TE buffer was then added to lyse the remaining red blood cells and the white blood cells collected by centrifugation as before. If any redness remained in the pellet, this process was repeated until the pellet was white. After removal of the last drop of supernatant from the pelleted white blood cells, 100 µl of K buffer containing proteinase K was added and the mixture incubated at 55° C. for 2 hours. The mixture was then heated to 95-100° C. for 8 minutes and the DNA lysates stored at −20° C. until needed.

Reagents

| | |
|---|---|
| TE buffer: | 10 mM TRIS-HCl pH 8.0 |
| | 1 mM EDTA |
| K buffer: | 50 mM KCl |
| | 10 mM TRIS-HCl pH 8.3 |
| | 2.5 mM MgCl$_2$ |
| | 0.5% Tween 20 |

Prior to use for lysates, 10 µl of 20 mg/ml proteinase K (Molecular Probes Inc.) per 1.0 ml of K buffer was added.

(ii) PCR

Reactions were set up as follows in thin walled 0.25 ml tubes (Perkin Elmer):

| | |
|---|---|
| 4.0 µl | 5 µM CRC Forward primer; |
| 4.0 µl | 5 µM CRC Reverse primer; |
| 4.0 µl | 5 µM KIT1 - REV primer; |
| 4.0 µl | 5 µM KIT1 - FOR primer; |
| 4.0 µl | 2 mM dNTPs (Pharmacia); |
| 4.0 µl | 35 mM MgCl$_2$. |

A wax bead (PCR Gem 50, Perkin Elmer) was added and the tube placed in a Perkin Elmer 9600 thermal cycler. The tube was then raised to 80° C. for 15 seconds followed by cooling to 4° C. A second set of reagents was then added to each tube as below:—

| | |
|---|---|
| 4.0 µl | 10x buffer; |
| 9.6 µl | sterile deionised water; |
| 0.4 µl | (0.5 units) AmpliTaq DNA polymerase (Perkin Elmer); |
| 2 µl | DNA lysate. |

Reaction tubes were then placed on a Perkin Elmer 9600 thermal cycler preheated to 94° C. and PCR carried out according to the regime indicated below:—

94° C. for 4 minutes;

20 cycles of 94° C. for 30 secs, 62° C. for 30 secs and 72° C. for 30 secs;

0° C. until required.

The number of cycles may vary depending upon the tissue used as the DNA source.

KIT Primers

```
Forward                                   (SEQ ID NO:21)
GAATATTGTTGCTATGGTGATCTCC KIT1-FOR Reverse                                   (SEQ ID NO:22)
    CCGCTTCTGCGTGATCTTCCTG KIT1-REV
```

CRC Primers

```
Forward                                   (SEQ ID NO:23)
CTGGATGTCCTGTGTTCCCTGT CRC-FORWARD Reverse                                   (SEQ ID NO:24)
    AGGTTTGTCTGCAGCAGAAGCTC CRC-REVERSE
```

The reverse KIT primer and the forward CRC primer are labelled with the ABI fluorescent dye FAM at the 5' end.

(iii) Electrophoresis and Quantitation of DNA Fragments

1 µl of the PCR was mixed with 2.5 µl of deionised formamide, 0.5 µl of GS350 DNA standards, 0.4 µl blue dextran solution, heated at 90° C. for 2 minutes followed by rapid cooling on ice. 3 µl of this mix were then loaded onto an AB 1373 DNA sequencer and DNA fragments separated on a 6% polyacrylamide gel in 1×TBE buffer for 2 hours at 700 V, 40 mA, 32 W. The fragments corresponding to the products from the KIT and CRC genes were quantitated using GeneScan software, the peak area for each of the bands being determined.

(iv) Results

The data given in the table below represents the results obtained from an experiment in which DNA lysates were produced from each of 23 animals, with two PCR tests being carried out on each lysate. The ratio of KIT peak area to CRC peak area was calculated for each PCR and the average taken of those samples from the same animal.

| Animal | Genotype | KIT/CRC peak area ratio |
| --- | --- | --- |
| 1 | II | 3.25 |
| 2 | Ii | 2.45 |
| 3 | II | 2.94 |
| 4 | ii | 1.16 |
| 5 | ii | 1.34 |
| 6 | ii | 1.20 |
| 7 | Ii | 2.18 |
| 8 | Ii | 2.19 |
| 9 | II | 2.88 |
| 10 | ii | 1.30 |
| 11 | Ii | 1.84 |
| 12 | II | 2.84 |
| 13 | ii | 1.50 |
| 14 | ii | 1.30 |
| 15 | Ii | 2.07 |
| 16 | ii | 1.31 |
| 17 | ii | 1.14 |
| 18 | Ii | 2.02 |
| 19 | Ii | 1.87 |
| 20 | Ii | 2.00 |
| 21 | ii | 0.99 |
| 22 | ii | 1.15 |
| 23 | II | 2.80 |

The upper and lower limits for the ratio values from animals of the different genotypes II, Ii and ii in this experiment are as below:

| Genotype | Upper Limit | Lower Limit |
| --- | --- | --- |
| I/I | 3.25 | 2.80 |
| I/i | 2.45 | 1.84 |
| i/i | 1.50 | 0.99 |

These results illustrate differentiation of the genotypes using this test.

Example 13

The second test utilises unique sequences of DNA that are present at one end of the duplication (or both ends if the duplicated region is reversed relative to the rest of the gene or if the duplicated region does not occur in direct tandem with the non-duplicated region). Oligonucleotide primers for use in PCR are designed such that at the annealing temperatures used in the PCR process, they will anneal only to the junction regions at the end of the duplicated region. A PCR is then carried out using two pairs of oligonucleotides. One pair consists of the aforementioned primer spanning the junction region and a second primer a suitable distance away which allows amplification to occur only from 1 allele containing duplication. The second pair of primers allow amplification of a sequence present only as a single copy in the haploid genome. The product of this reaction, carried out in the same tube, functions as an internal standard as in the previous test. The ratio of product from the reaction specific to the junction region is measured relative to that from the single copy control sequence.

In this test there is a larger difference between the predicted ratios of the products from the different genotypes. The relative levels of product and their ratios are illustrated below:—

| Genotype | Junction Product | Control Product | Ratio |
| --- | --- | --- | --- |
| II | 2 | 2 | 1:1 |
| Ii | 1 | 2 | 1:2 |
| ii | 0 | 2 | 0:2 |

These larger ratios allow greater differentiation between the ranges of results obtained from the different genotypes, reducing risks of miss-scoring animals.

Example 14

(i) DNA Preparation

DNA can be prepared as described in example 12.

(ii) PCR

Reactions were set up as follows in thin walled 0.25 ml tubes (Perkin Elmer):

| | |
| --- | --- |
| 2.0 µl | 5 mM KITDEL2-FOR primer; |
| 2.0 µl | 5 mM KITDEL2-REV primer; |
| 1.0 µl | 2 mM dNTPs (Pharmacia); |
| 1.2 µl | 25 mM MgCl2 |
| 2.0 µl | 10x buffer (without MgCl2) |
| 0.1 µl | (0.5 units) AmpliTaq DNA polymerase (Perkin Elmer); |
| 2.0 µl | DNA lysate; |
| 9.7 µl | sterile deionised water. |

Reaction tubes were then placed on a Perkin Elmer 9600 thermal cycler and PCR carried out according to the regime indicated below:—

95° C. for 1 minute;

3 cycles of 95° C. for 15 secs, 50° C. for 20 secs and 72° C. for 40 secs;

27 cycles of 94° C. for 15 secs, 50° C. for 20 secs and 72° C. for 50 secs;

72° C. for 5 minutes;

4° C. until required.

The number of cycles may vary depending upon the tissue used as the DNA source.

KIT Primers

```
Forward                                      (SEQ ID NO:25)
GAAAGTGA(C/T)GTCTGGTCCTAT(C/G)GGAT KITDEL2-FOR Reverse                                      (SEQ ID NO:26)
AGCCTTCCTTGATCATCTTGTAG KITDEL2-REV
```

(iii) Electrophoresis

1 µl of the PCR product was mixed with 3 µl loading buffer (95% deionised formamide, 10 mM NaOH, 20 mM EDTA, 0.05% bromophenolblue, 0.05% Xylene-cyanol), heated to 95° C. for 3 minutes followed by rapid cooling on ice. The sample was then loaded on an 8% native polyacrylamide gel (Protogel, 37.5:1 Acrylamide:bisacrylamide, National Diagnostics, Atlanta) in 1×TBE buffer (89 mM Tris, 89 mM boric acid, 2 mM EDTA.Na2). The DNA fragments were separated by electrophoresis for 4.5 hours at 6 W with a constant temperature of 20° C. and 0.6×TBE as running buffer in a vertical slab unit (SE600 Hoefer Scientific Instruments, San Francisco).

(iv) Visualisation of DNA Fragments by Silver Staining

After electrophoresis the gel was incubated, with gentle agitation, in the fix solution for 20 minutes or until the tracking dyes were no longer visible. The gel was rinsed three times (2 minutes each with agitation) in deionised water. The gel was then incubated in the staining solution for 40 minutes, with gentle agitation, followed by a brief wash (5-10 seconds) in deionised water and direct transfer to the developing solution. The gel was incubated in the developing solution until bands were clearly visible and then the development was terminated by adding an equal volume of fix solution. Finally, the gel was rinsed for 2 minutes in deionised water.

Reagents

| | |
|---|---|
| Fix solution: | 10% glacial acetic acid in deionised water |
| Staining solution: | 2 g silver nitrate (AgNO3)<br>3 ml 37% formaldehyde<br>2 litres deionised water |
| Developing solution: | 60 g sodium carbonate (Na2CO3) dissolved in 2 liters deionised water. Immediately before use add 3 ml 37% formaldehyde and 400 ml sodium thiosulfate (10 mg/ml). The solution should be at a temperature of 10–12° C. when used. |

(v) Results

This SSCP analysis reveals an informative polymorphism so far only found in animals with the dominant white phenotype (FIG. 9). In lanes 1 to 8 the analysis was carried out on DNA from Swedish Landrace pigs carrying the dominant white colour and in lanes 9 and 10 DNA was from wild pigs of wild type colour. The polymorphic bands are indicated. The polymorphism is characterised by two unique fragments only present in animals carrying a duplicated KIT gene of allele type I. The fragments represent heteroduplexes of DNA strands from PCR products of unequal length representing the duplicated and non-duplicated copy of the KIT gene. The results of a screening test with this marker using 40 unrelated animals representing five breeds and 190 F2 animals from a Large White/Wild pig intercross are presented in the table below:

| | | | HETERODUPLEX | |
|---|---|---|---|---|
| BREED | COLOUR | NO. OF ANIMALS | PRESENT | NOT PRESENT |
| SWEDISH LANDRACE | WHITE | 10 | 10 | 0 |
| SWEDISH LARGE WHITE | WHITE | 8 | 8 | 0 |
| SWEDISH HAMPSHIRE | COLOURED | 10 | 0 | 10 |
| SWEDISH DUROC | COLOURED | 10 | 0 | 10 |
| WILD PIG | COLOURED | 2 | 0 | 2 |
| LARGE WHITE /WILD PIG INTERCROSS | WHITE | 131 | 106 | 25 |
| | PATCH | 9 | 0 | 9 |
| | COLOURED | 50 | 0 | 50 |

The results show that this particular polymorphism is very closely associated with the presence of the KIT duplication. It is not completely associated with the duplication as some white animals did not show the heteroduplex pattern. The polymorphism is therefore an example of a closely linked genetic marker which by itself or in combination with other linked markers can be used to differentiate genotypes as regards the dominant white coat colour.

Example 15 i) DNA Extraction

DNA was prepared as in example 12.

ii) PCR

Reactions were set up in 0.25 ml thin walled reaction tubes (Perkin Elmer) as follows:

| | |
|---|---|
| 0.5 µl | 5 µM KITDEL1-FOR primer |
| 0.5 µl | 5 µM KITDEL1-REV primer |
| 1.0 µl | 2 mM dNTPs (Pharmacia) |
| 1.0 µl | 15 mM MgCl$_2$ |
| 1.0 µl | 10X buffer |
| 4.9 µl | Sterile distilled water |
| 0.1 µl | AmpliTaq DNA polymerase |
| 1.0 µl | DNA lysate |

Reaction tubes were then placed in a Perkin Elmer 9600 thermal cycler and PCR carried out according to the regime 94° C. for 4 minutes;
21 cycles of 94° C. for 30 sec, 60° C. for 30 sec, and 72° C. for 30 sec
72° C. for 4 min;
4° C. until required.

The number of cycles used may vary depending on the tissue used as the source of the DNA.

Primers

```
forward                                          (SEQ ID NO:27)
TGTGGGAGCTCTTCTCTTTAGG KITDEL1-FOR reverse                                          (SEQ ID NO:28)
CCAGCAGGACAATGGGAACATCT KITDEL1-REV
```

The reverse primer was labelled with the ABI fluorescent dye FAM at the 5' end.

iii) Electrophoresis and Quantitation of DNA Fragments

1 µl of the PCR was mixed with 1.5 µl of deionised formamide, 0.25 µl of GS350 DNA standards, 0.25 µl loading buffer (50 mg/ml blue dextran, 25 mM EDTA) and heated at 90° C. for two minutes followed by rapid cooling on ice. 1.75 µl of this was then loaded onto an ABI 377DNA sequencer and DNA fragments separated on a 4.12% polyacrylamide gel in 1×TBE buffer for two hours at 3000 V, 60 mA, 200 W and 48° C. The 97 bp and 93 bp fragments corresponding to the products from the KIT gene template lacking the deletion and containing the deletion respectively were quantitated using GeneScan software, the peak area for each of the bands being determined.

Results

The data given in the table below represents the results obtained from an experiment in which DNA lysates were produced from each of 20 animals of known genotype with one PCR test being carried out on each lysate. The ratio of the peak area of the product from the DNA template not containing the four base pair deletion to that containing the deletion was calculated.

| ANIMAL | GENOTYPE | Non del/del peak area ratio |
|---|---|---|
| 1 | II | 1.347 |
| 2 | II | 1.21 |
| 3 | II | 1.33 |
| 4 | II | 2.267 |
| 5 | II | 0.444 |
| 6 | II | 0.713 |
| 7 | II | 8.387 |
| 8 | II | 0.994 |
| 9 | II | 1.673 |
| 10 | II | 1.056 |
| 11 | Ii | 1.751 |
| 12 | Ii | 1.73 |
| 13 | Ii | 1.83 |
| 14 | Ii | 0.631 |
| 15 | Ii | 1.975 |
| 16 | Ii | 2.147 |
| 17 | Ii | 1.901 |
| 18 | Ii | 1.749 |
| 19 | Ii | 2.103 |
| 20 | Ii | 2.026 |

For this small sample the value of 1.5 which is midway between the predicted ratio values for each genotype (expected ratio=2 for Ii and 1 for II) might be used as the dividing line for scoring the animals to either genotype. It can be determined from the table that 7/10 II and 9/10 Ii are identified as the correct genotype.

Example 16

Sequencing of KIT cDNA Clones mRNA was isolated from peripheral blood leukocytes from white (Landrace/Large White) and coloured (Hampshire) pigs using the Message Maker mRNA isolation system (Gibco BRL) with one mRNA selection from total RNA. 100 ng poly(A)+ mRNA was reverse-transcribed with random primers (First-Strand cDNA Synthesis kit, Pharmacia Biotech) and the product was used at a 1:10 dilution for RT-PCR using the proof-reading Advantage KlenTaq Polymerase (Clontech) according to the manufacturer's recommendation. The following primers were used to amplify almost the entire coding sequence and some of the 5' untranslated region: KIT40 (5'-GGC TCT GGG GGC TCG GCT TTG C) (SEQ ID NO:29) corresponding to the 5'untranslated region and KIT22S (5'-TCA GAC ATC TTC GTG GAC AAG CAG AGG) (SEQ ID NO:30) corresponding to exon 21; both primers had been designed using consensus sequence of the human and mouse KIT sequences in the GENBANK database. The RT-PCR products were gel purified and cloned using the pGEM-T vector system (Promega). Plasmid clones were sequenced using a set of internal primers and the ABI Prism™ dRhodamine Terminator Cycle Sequencing Kit (PE Applied Biosystems). Two subclones representing each type of KIT sequence were initially sequenced and in those cases where a discrepancy was observed (possibly due to PCR errors) additional clones were sequenced over those particular nucleotide sites. RT-PCR analysis of KIT exon 16-19 was carried out with the primers KIT1F (5'-TCR TAC ATA GAA AGA GAY GTG ACT C) (SEQ ID NO:31) and KIT7R (5'-AGC CTT CCT TGA TCA TCT TGT AG) (SEQ ID NO:32).

Results

The sequence of the KIT gene coding region derived from an animal of the Hampshire Breed is shown in FIG. 10. Differences between KIT cDNA sequences cloned from a Hampshire and a Yorkshire/Landrace pig, respectively are shown in the table below. The sequence comparison includes the whole open reading frame 2919 bp, except for the last 27 bp occupied by the reverse PCR primer. Exon and base pair position number as well as amino acid codon are given for each difference. Polymorphic bases are shown in bold. A dash indicates identity with the Hampshire (i) allele.

| Breed | Coat Colour | Assumed Genotype | Sequence variant | Splicing exon 14 | Splicing exon 17 | Exon 5 821 | Exon 5 828 | Exon 6 978 | Exon 6 984 | Exon 6 1008 | Exon 9 1464 | Exon 18 2502 | Exon 19 2678 | SEQ ID NO: |
|---|---|---|---|---|---|---|---|---|---|---|---|---|---|---|
| Hampshire | coloured | i/i | KIT1*0101 | normal | normal | AGG Arg | ACA Thr | AAC Asn | GGA Gly | GAG Glu | ACG Thr | CCT Pro | GCG Ala | 33 34 |
| Yorkshire/ Landrace | white | I/I[1] | KIT1*0201 | normal | normal | — | — | AAT Asn | GGC Gly | GAA Glu | ACA Thr | CCC Pro | GTG Val | 35 36 |
| | | | KIT1*0202 | normal | normal | AAC Arg | ACG Thr | — | — | GAA Glu | ACA Thr | CCC Pro | GTG Val | 37 38 |
| | | | KIT2*0101 | normal | skipped | — | — | AAT Asn | GGC Gly | GAA Glu | ACA Thr | CCC Pro | GTG Val | 39 40 |
| | | | KIT2 splice variant | skipped[2] | skipped | — | — | AAT Asn | GGC Gly | GAA Glu | ACA Thr | CCC[2] | GTG[2] | 41 42 |

[1]Genotype I/I, I/I* or I*/I* inferred by the pig being a sow that got a 100% white farrow following mating to a Hampshire (i/i) boar.
[2]The skipping of exon 14 (151 bp) cause a nonsense translation with termination at position 2161.

Example 17

DNA Preparation

Genomic DNA was prepared as described in example 12.

PCR

A 158 bp fragemnt covering 99 bp of the end of exon 19 and 59 bp of the KIT gene was amplified using forward primer LA93 (5'-GAG CAG CCC CTA CCC CGG AAT GCC AGT TGA-3') (SEQ ID NO:7) and reverse primer KIT56 (5'-CTT TAA AAC AGA ACA TAA AAG CGG AAA CAT CAT GCG AAG G-3') (SEQ ID NO:8). PCR was carried out on a Perkin Elmer 9600 Thermal Cycler in a total volume of 20 μl containing 25 ng genomic DNA, 1.5 mM $MgCl_2$, 50 mM Kcl, 10 mM Tris-HCl, pH 8.3, 200 μM dNTPs, 0.5 u AmpliTaq Gold (Perkin Elmer) and 10 pmol of both LA93 and KIT56 primer. To activate AmpliTaq Gold, initial heat denaturation was carried out at 94° C. for 10 minutes followed by 32 cycles each consisting of 45 sec at 94° C., 45 sec at 55° C. and 45 sec at 72° C.

Restriction Digestion and Electrophoresis

The PCR amplification product is 158 bp in length. To test for polymorphism at position 93 of this product (corresponding to position 2678 of the KIT cDNA sequence) digestion reactions were set up and incubated as below:

| | |
|---|---|
| 6.0 µl | PCR product |
| 1.0 µl | 10x reaction buffer 3 (New England Biolabs) |
| 0.2 µl | AciI (5u/µl) |
| 2.8 µl | deionised water |

Following digestion at 37° C. for 120 minutes each 10 µl reaction volume had 2 µl of loading dye aded and the mix was loaded on an 8% native polyacrylamide gel (Protogel, 37.5:1 acrylamide:bisacrylamide, National Diagnostics, Atlanta) in 0.5×TBE (44.5 mM Tris pH8.0, 44.5 mM boric acid and 0.5 mM EDTA) and electrophoresed for 3 hours at 200v in a vertical slab gel unit (SE600 Hoefer Scientific Instruments). Products are visualised by ethidium bromide staining.

Results

The reverse primer is designed such that an AciI site is introduced into the amplified sequence. This results in digestion of amplicon with AciI releasing a fragment of 23 bp that allows confirmation of the digestion process. Digestion of the remaining 135 bp fragment into fragments of 92 and 43 bp is dependant on the nucleotide at the position corresponding to position 2678 of the KIT cDNA sequence. T at this position prevents digestion while a C at this position allows digestion. Gel resolution is not sufficient to allow resolution of the 23 bp fragment but comparison to undigested product allows confirmation of the process.

FIG. 11 illustrates the results obtained with animals of a range of genotypes.

The test was used to analyse a total of 66 unrelated individuals from seven breeds of pig. The results are shown in the table below:

| | | KIT | Genotype at pos'n 2678 | | |
|---|---|---|---|---|---|
| Breed | No. | Genotype[1] | C/C | C/T | T/T |
| Hampshire | 4 | i/i | 1 | 1 | 2 |
| Polish Wild Boar | 13 | i/i | 0 | 1 | 12 |
| Duroc | 11 | i/i | 0 | 1 | 10 |
| Pietrain | 1 | i/i | 0 | 0 | 1 |
| Swedish Wild Boar | 1 | i/i | 1 | 0 | 0 |
| Swedish Landrace | 12 | I/I | 0 | 0 | 12 |
| | 5 | I/IP | 0 | 2 | 3 |
| Swedish Yorkshire | 14 | I/I | 0 | 1 | 13 |
| | 5 | I/IP | 0 | 1 | 4 |

[1]Genotype based on NlaIII RFLP analysis as described in example 11.

Example 18

Determination of Genotype at the I Locus Using a Rapid DNA Based Test

Crude DNA lysates were prepared from hair samples from animals of three breeding lines, a Hampshire based line, a Large White line, and white animals from a cross bred line originally produced from the two former lines. Four hair follicles were placed into 100 µl of K buffer (50 mM KCl, 10 mM Tris-HCl pH 8.3, 2.5 mM MgCl$_2$, 0.5% w/v Tween 20) and 1 µl Proteinase K (15 mg/ml) (Boehringer) added. This mix was incubated for 2 hours at 55° C. followed by 16 min at 95° C. DNA was also prepared as described in example 12.

Allelic discrimination reactions were set up using the PE Applied Biosystems TaqMan™ system. 25 µl reactions contained the primers E19FOR (5-GAGCAGCCCCTAC-CCCGGAATGCCAGTTGA-3') (SEQ ID NO:43) and E19REV (5-CTTTAAAACAGAACATAAAAGCGGAAA-CATCATGCGAAGG-3') (SEQ ID NO:44) at 300 nM, 8% glycerol (w/v) 1×TaqMan™ buffer A (PE Applied Biosystems), 5 mM MgCl$_2$, 200 µM dATP, dGTP, dCTP and dUTP, 0.65 units AmpliTaq Gold™ (PE Applied Biosystems), 0.25 units AmpErase™ UNG (PE Applied Biosystems) and the TaqMan™ probes E19PC (5'-CATACATTTCCGCAGGTG-CATGC-FAM) (SEQ ID NO:68) and E19PT (5'-TCATA-CATTTCCACAGGTGCATGC-TET) (SEQ ID NO:69) at a concentration of 10 mM. 1 µl of crude lysate DNA was used as template. PCR amplification was carried out using a PE9600 thermal cycler (PE Applied Biosystems) or a the ABI7700 Prism (PE Applied Biosystems) with a thermal cycling regime of 50° C. for 2 min followed by 95° C. for 10 min followed by 40 cycles of 95° C. 15 sec, 62° C. 1 min. 8 control samples of each homozygote genotype, 2678C and 2678T, and 8 no template controls where deionized water was substituted for template controls were used per 96 well plate. Allele identification based on these reactions was carried out using the allelic discrimination function of the ABI7700 Prism (PE Applied Biosystems).

Results

The test was used to analyse a total of 20 unrelated individuals from four breeds of pig. The results are shown in the table below:

| | | Assumed KIT | Genotype at pos'n 2678 | | |
|---|---|---|---|---|---|
| Breed | No. | Genotype | C/C | C/T | T/T |
| Hampshire | 5 | i/i | 1 | 1 | 3 |
| Landrace | 5 | I/I | 0 | 0 | 5 |
| Duroc | 5 | i/i | 0 | 0 | 5 |
| Pietrain | 1 | i/i | 0 | 0 | 5 |

Example 19

Complete Cosegregation of the Belt Coat Colour Locus and KIT

Method

Hampshire pigs have a characteristic coat colour phenotype with a white belt on a solid black background. Belt is determined by a dominant allele (Be). The segregation of the Belt locus was investigated in a backcross between Hampshire (Be/Be) and Pietrain (be/be) pigs. F1 sows (Be/be) were back-crossed to pure-bred Pietrain (be/be) boars. DNA preparations were carried out exactly as described in Example 3.

KIT Exon 19 PCR RFLP i) PCR to Produce DNA for the RFLP Test

A 158 bp fragment covering 99 bp of the 3' end of exon 19 and 59 bp of intron 19 of the KIT gene was amplified using the following primers:

forward LA93 (5'-GAGCAGCCCCTACCCCGGAATGC-CAGTTGA-3') (SEQ ID NO:7); and reverse

KIT56 (5'-CTTTAAAACAGAACATAAAAGCGGAAA-CATCATGCGAAGG-3') (SEQ ID NO:8). PCR was carried out in a total volume of 20 µl containg 25 ng genomic DNA, 1.5 mM MgCl$_2$, 50 mM KCl, 10 mM tris-HCl, pH 8.3, 200 µM dNTPs, 0.5 U AmpliTaq Gold (Perkin Elmer) and 10 pmol of both LA93 and KIT56 primer. To activate Amplitaq Gold, initial heat denaturation was carried out at 94° C. for 10 minutes followed by 32 cycles each consisting of 45 sec at 94° C., 45 sec at 55° C. and 45 sec at 72° C.

ii) Restriction Enzyme Digestion and Electrophoresis

The PCR amplification product is 158 bp in length. To test for polymorphism at position 93 of this product, digestion reactions were set up and incubated as follows:

| | |
|---|---|
| 6.0 µl | PCR amplified DNA |
| 1.0 µl | 10X NEBuffer 3 |
| 0.2 µl | AciI (5 U/µl) |
| 2.8 µl | dH2O |

(1×NEBuffer (New England Biolabs) contains 100 mM sodium chloride, 50 mM Tris-HCl, 10 mM magnesium chloride, and 1 mM DTT). Following digestion at 37° C. for 120 minutes, two µl loading dye was added to each sample and the mix loaded on a 12% native polyacrylamide gel in 0.5% TBE (44.5 mM Tris pH 8.0, 44.5 boric acid and 0.5 mM EDTA) and electrophoresed for 3 hours at 200 V in a vertical slab unit. Products were visualised by Ethidium bromide staining.

Results

KIT nucleotide 2678 is polymorphic and a C or T occurs at this position. The presence of a C creates a restriction site for Aci I which is absent when a T is present. A second AciI site has been engineered into the reverse primer KIT56 to serve as an internal control of digestion and is therefore invariant. The polymorphism can be detected by a simple PCR-RFLP analysis as described in the table below.

Detection of KIT Single Nucleotide Polymorphism (SNP) at Position 2678

| Nucleotide | Size in bp of DNA fragments after digestion |
|---|---|
| C | 23 + 43 + 92 |
| T | 23 + 135 |

The cosegregation of the Belt and KIT loci in this pedigree is summarised in the table below.

Cosegregation between KIT and Belt in a Hampshire/Pietrain backcross

| Animal | No tested | Phenotype | Belt locus | KIT SNP2678 |
|---|---|---|---|---|
| F1 sows | 14 | Belt | Be/be | C/T |
| Pietrain sires | 2 | non-Belt | be/be | T/T |
| Offspring | 41 | Belt | Be/be | C/T |
| Offspring | 41 | non-Belt | be/be | T/T |

The complete cosegregation between the Belt phenotype and the KIT polymorphism shows that this phenotype most likely is controlled by a mutation at the KIT locus. This means that detection of KIT polymorphism can be used to identify animal products derived from Hampshire pigs since the Belt is the most important breed determinant in Hampshire pigs. It is likely that the Belt phenotype present in Saddleback and Hannover-Braunschweig pigs is controlled by the same locus.

Example 20

Determination of the Sequence of the 5' Untranslated and 5' Coding Region of the αMSHR Gene.

The entire coding region of the αMSHR gene was determined and compared between pig breeds known to carry the different at the E locus, $E^h$, $E^+$ and $E^p$. Hampshire carries $E^h$ and has a solid black body interrupted with a white belt. This belt is the result of another coat colour locus. The Wild Boar which carries allele $E^+$ has a wildtype phenotype while the Pietrain breed carries allele $E^p$ and is characterized by having black spots on a white body.

PCR to Produce DNA for Clone Construction

The entire coding region of the αMSHR gene was amplified from genomic DNA using primers EPIG10 and EPIG16. These primers have sequence:

EPIG5'-GGT CTA GAT CAC CAG GAG CAC TGC AGCACC-3' (SEQ ID NO:45)

EPIG5'-GGG AAG CTT GAC CCC CGA GAG CGA CGC GCC-3' (SEQ ID NO:46)

PCR was carried out on a DNA thermal cycler (Perkin Elmer 9600) in a total volume of 20 µl containing 25 ng genomic DNA, 1.5 mM MgCl$_2$, 50 nM KCl, 10 mM TriHCl, pH 8.3, 200 µM dNTPs, 5.0% DMSO (dimethyl sulfoxide), 0.5 U AmpliTaq Gold (Perkin Elmer) and 10 pmol of both EPIG10 and EPIG16. To activate AmpliTaq Gold, initial heat denaturation was carried out at 96° C. for 10 minutes followed by 32 cycles each consisting of 45 sec at 94° C., 45 sec at 55° C. and 45 sec at 72° C. The final extension lasted for 7 min at 72° C.

Cloning of PCR Products

To facilitate cloning of PCR products, both primers were designed with restriction endonuclease recognition sites located at the 5' end. Primer EPIG10 has sequence TCTAGA which is cut using enzyme XbaI and EPIG16 contains sequence AAGCTT which is cut using enzyme HindIII. Following PCR as described above, the entire reaction volume was electrophoresed and purified using the Qiaex II gel extraction kit following the manufacturers instructions (Qiagen). The purified PCR product was digested prior to ligation as follows:

| | |
|---|---|
| PCR product | 17.0 µl |
| 5.0 u HindIII (Amersham) | 1.0 µl |
| 5.0 u XbaI (Amersham) | 1.0 µl |
| x10 reaction buffer M (Amersham) | 3.0 µl |
| x10 bovine serum albumin (Amersham) | 3.0 µl |
| H$_2$O | 5.0 µl |

The reactions were incubated at 37 degrees C. for 16 hours before the digested DNA was purified by passage through a QIAquick spin column following the manufacturers instructions (Qiagen). PCR products were ligated into 100 ng of vector pRc/CMV (Invitrogen) using 400 U T4 DNA ligase (New England Biolabs) in a total reaction volume of 20 µl containing 10 mM MgCl$_2$, 50 mM Tris-HCl, pH7.5, 10 mM dithiothreitol, 1 mM ATP and 25 µl/ml bovine serum albumin. Ligation reactions proceeded at 16 degrees for 16 hours.

Preparation and Sequencing of Plasmid DNA

Plasmid DNA was purified from overnight bacterial culture using the Jetstar plasmid midi kit 50 (Genomed) and the resulting DNA diluted to 15 µl/pl. Dye terminator cycle sequencing was performed using AmpliTaq DNA polymerase in accordance with the ABI Prism protocol P/N 402078 (perkin Elmer). Cycle sequencing reactions comprised 1.6 pmole of either T7 or SP6 sequencing primer (Promega), 15 ng of plasmid DNA and the terminator ready reaction mix (Perkin Elmer). The cycle sequencing reactions were performed in a GeneAmp 9600 machine over 25 cycles, each consisting of 10 sec at 96° C., 5 sec at 50° C. and 4 min at 60° C. Extension products were purified for gel separation using ethanol precipitation, loaded and run on a 377 ABI Prism DNA sequencer as described by the instrument protocol (Perkin Elmer protocol P/N 402178).

Results

A 2 bp insertion was identified in the αMSHR gene of pigs of the Pietrain breed which carry the $E^p$ allele between nucleotide positions equivalent to 66 and 67 in the Wild Boar αMSHR sequence. This results in a shift in the translation frame and creates a TGA stop codon at nucleotide positions equivalent to 161 to 163 in the Wild Boar αMSHR sequence. The 5' portion of the αMSHR coding sequence compared between three breeds is shown below. This comparison illustrates the two base pair insertion present within the alleles carried by the Pietrain animal when compared with either the Hampshire or Wild Boar alleles. The ATG start codon is highlighted in bold, the 3' end of primer EPIG16 is shown in italics and bases in common with the Pietrain sequence are marked with a dash. Missing bases are marked with:

```
Pietrain
CGACGCGCCC TCCCTGCTCC CTGGCGGGAC GATGCCTGTG CTTGGC-
CCGG
Meishan
---------- ---------- ---------- ---------- -------
---
Wild Boar
---------- ---------- ---------- ---------- -------
---
Pietrain
AGAGGAGGCT GCTGGCTTCC CTCAGCTCCG CGCCCCCAGC CGC-
CCCCCCC
Meishan
---------- ---------- ---------- --------:: -------
---
Wild Boar
---------- ---------- ---------- --------:: -------
---
Pietrain
GCCTCGGGCT GGCCGCCAAC CAGACCAACC AGACGGGCCC CCAGT-
GCCTG
Meishan
---------- ---------- ---------- ---------- -------
---
Wild Boar
---------- ---------- ---------- ---------- -------
---
Pietrain
GAGGTGTCCA TT (SEQ ID NO:47)
Meishan
---------- -- (SEQ ID NO:48)
Wild Boar
---------- -- (SEQ ID NO:48)
```

These results are also incorporated into FIG. 1a

Example 21

A rapid DNA test for the presence of the 2 bp insertion mutation in the porcine αMSHR gene allowing rapid distinction of the $E^p$ allele from all other alleles identified at this locus.

PCR was conducted with forward primer EPIG16 (see above) and reverse primer MC1R121A exactly as described above. The reverse primer was labeled with ABI dye Hex and has sequence: MC1R121A 5'-Hex-GGA CTC CAT GGA GCC GCA GAT GAG CAC GGT 3' (SEQ ID NO:49).

Following PCR cycling, 0.2 µl of the reaction volume was mixed with 2.5 µl of deionised formamide, 0.5 µl of GS500 DNA standard (ABI) and 0.4 µl blue dextran solution before being heated to 90° C. for 2 minutes and rapidly cooled on ice. 1 µl of this mix was then loaded onto a 377 ABI Prism sequencer and the DNA fragments separated on a 6% polyacrylamide gel in 1×TBE buffer for 2 hours at 700 V, 40 mA, 32 W. The length of the resulting PCR products were determined using the GeneScan software (ABI).

Results

A test was devised to assay genomic DNA directly for the presence of the identified 2 bp insertion. Primers EPIG16 and MC1R121A were used to PCR amplify 448 bp of the 5' portion of the wildtype porcine MC1R gene. To facilitate fluorescent detection of amplified products, the ABI dye HEX was covalently attached to the 5' end of primer MC1R121A. PCR was conducted on a number of unrelated individuals from three breeds and the resulting PCR products size determined using the GeneScan software (ABI). The results are presented in the table below:

| Breed | Number tested | Extension Genotype | Size of PCR product | |
|---|---|---|---|---|
| Pietrain | 5 | $E^p/E^p$ | 0 | 5 |
| Large White | 3 | $E^p/E^p$ | 0 | 3 |
| Hampshire | 5 | $E^h/E^h$ | 5 | 0 |

Analysis of the length of PCR products amplified between individuals showed either a 448 bp or 450 bp product resulted The expected 448 bp fragment was amplified from each Hampshire animal, however a product 2 bp longer was detected from each Pietrain and Large White animal tested. This indicates the 2 bp insertion identified via sequence analysis to be present in the genomic DNA of Pietrain and Large White, two breeds ascribed the $E^p$ allele, but not in Hampshire which carries $E^h$.

Example 22

In addition to the coding region of the αMSHR gene, DNA sequence polymorphism may exist between breeds within the untranslated regions (UTR). Sequence information was collected from the 3' UTR and compared between six breeds of pigs which display a variety of coat color phenotypes.

PCR to Produce DNA for Sequencing

A 454 bp product containing 38 coding nucleotides from the 3' portion of the molecule and 416 bp of 3' untranslated region (not including primer binding sites) was amplified using primers EPIG13 and EPIG14. These primers have sequence:

EPIG13 5'-GCA AGA CCC TCC AGG AGG TG-3' (SEQ ID NO:50)
EPIG14 5'-CAC TGA GCC GTA GAA GAG AG- 3' (SEQ ID NO:51)

PCR was carried out on a DNA thermal cycler (Perkin Elmer 9600) in a total volume of 20 µl containing 25 ng genomic DNA, 1.5 mM MgCl$_2$, 50 mM KCl, 10 mM Tris-HCl, pH8.3, 200 µM dNTPs, 0.5 U AmpliTaq Gold (Perkin Elmer) and 10 pmol of both EPIG13 and EPIG14. To activate AmpliTaq Gold, initial heat denaturation was carried out at 96° C. for 10 minutes followed by 32 cycles each consisting of 45 sec at 94° C., 45 sec at 55° C. and 45 sec at 72° C. The final extension lasted for 7 min at 72° C.

Sequencing of PCR Products

PCR products were sequenced using dye terminator chemisty. This first requires purification of PCR product free from excess dNTPs and primers. This was achieved by passage of the template DNA through a QIAquick spin column following the manufacturers instructions (Qiagen). Cycle sequencing reactions were performed on 20 ng of purified template using either EPIG13 or EPIG14 as described in Example 1.

Results

Primers EPIG13 and EPIG14 were used to amplify a 454 bp region of DNA which comprises both the 3' terminal coding region of the MC1R gene and the immediately adjacent 3' UTR. The sequence information collected is displayed in FIG. 15 and two polymorphic positions were identified.

The first polymorphism identified is a 1 bp deletion common to Meishan and Large Black which occurs seven positions downstream from the stop codon at the equivalent of nucleotide position 1007 in the Wild Boar sequence. As this deletion occurs outside the translated region it is not expected to alter the amino acid composition of the resulting receptor molecule, however its influence on mRNA stability and 3' end formation through endonucleolytic cleavage is unknown. It is unique to two breeds which carry $E^m$ and which carry a variant of the αMSHR gene not found in any other breed examined to date.

The second polymorphism is a base substitution at nucleotide position 1162 unique to the European Wild boar. FIG. 12 shows five breeds to have a G base at this position and the Wild boar to contain an A. This sequence difference offers the possibility to distinguish the European Wild boar from the other breeds analysed with a DNA based test.

The invention claimed is:

1. A method for:
   (a) differentiating animals and animal products on the basis of breed origin; or
   (b) determining or testing the breed origin of an animal product; or
   (c) validating an animal product;
      comprising the steps of:
      (i) providing a sample of the animal product; and
      (ii) analysing the allele(s) of one or more breed determinant genes present in the sample;
   wherein said animal is a pig;
   wherein said breed determinant gene is coat colour gene αMSHR; and
   wherein the step of analysing the αMSHR gene comprises: (1) restriction fragment length polymorphism (RFLP) analysis, involving digesting the pig nucleic acid with one or more of the restriction enzymes BstUI, HhaI, and/or BspHI, and/or (2) the identification of a polymorphism at nucleotide position 283, 305, 363, 370, 491, 727, 729, 1162, or between nucleotide positions 60 and 70, or between nucleotide positions 1005 and 1010 of the sequence of pig αMSHR gene.

2. A method of determining the coat colour genotype of a pig comprises:
   (i) obtaining a sample of pig nucleic acid; and
   (ii) analysing the nucleic acid obtained in (i) to determine which allele or alleles of the αMSHR gene is/are present,
   wherein the analysis step (ii) comprises restriction fragment length polymorphism (RFLP) analysis, involving digesting the pig nucleic acid with one or more of the restriction enzymes BstUI, HhaI, and/or BspHI, and/or the analysis step involves identification of a polymorphism at nucleotide position 283, 305, 363, 370, 491, 727, 729, 1162, or between nucleotide positions 60 and 70, or between nucleotide positions 1005 and 1010 of the sequence of pig αMSHR gene.

* * * * *

SEQUENCE LISTING

```
<160> NUMBER OF SEQ ID NOS: 69

<210> SEQ ID NO 1
<211> LENGTH: 33
<212> TYPE: DNA
<213> ORGANISM: Artificial Sequence
<220> FEATURE:
<223> OTHER INFORMATION: aMSHR Forward Primer 1

<400> SEQUENCE: 1
tgtaaaacga cggccagtrg tgcctggagg tgt                              33

<210> SEQ ID NO 2
<211> LENGTH: 24
<212> TYPE: DNA
<213> ORGANISM: Artificial Sequence
<220> FEATURE:
<223> OTHER INFORMATION: aMSHR Reverse Primer 5

<400> SEQUENCE: 2
cgcccagatg gccgcgatgg accg                                        24

<210> SEQ ID NO 3
<211> LENGTH: 24
<212> TYPE: DNA
<213> ORGANISM: Artificial Sequence
<220> FEATURE:
<223> OTHER INFORMATION: aMSHR Forward Primer 2

<400> SEQUENCE: 3
cggccatctg ggcgggcagc gtgc                                        24

<210> SEQ ID NO 4
<211> LENGTH: 24
<212> TYPE: DNA
<213> ORGANISM: Artificial Sequence
<220> FEATURE:
<223> OTHER INFORMATION: aMSHR Reverse Primer 2
```

```
<400> SEQUENCE: 4
ggaaggcgta gatgaggggg tcca                                        24

<210> SEQ ID NO 5
<211> LENGTH: 24
<212> TYPE: DNA
<213> ORGANISM: Artificial Sequence
<220> FEATURE:
<223> OTHER INFORMATION: aMSHR Forward Primer 3

<400> SEQUENCE: 5
gcacatcgcc cggctccaca agac                                        24

<210> SEQ ID NO 6
<211> LENGTH: 24
<212> TYPE: DNA
<213> ORGANISM: Artificial Sequence
<220> FEATURE:
<223> OTHER INFORMATION: aMSHR Reverse Primer 3

<400> SEQUENCE: 6
ggggcagagg acgacgaggg agag                                        24

<210> SEQ ID NO 7
<211> LENGTH: 30
<212> TYPE: DNA
<213> ORGANISM: Artificial Sequence
<220> FEATURE:
<223> OTHER INFORMATION: LA93 Forward Primer

<400> SEQUENCE: 7
gagcagcccc tacccggaa tgccagttga                                   30

<210> SEQ ID NO 8
<211> LENGTH: 40
<212> TYPE: DNA
<213> ORGANISM: Artificial Sequence
<220> FEATURE:
<223> OTHER INFORMATION: KIT56 Reverse Primer

<400> SEQUENCE: 8
ctttaaaaca gaacataaaa gcggaaacat catgcgaagg                       40

<210> SEQ ID NO 9
<211> LENGTH: 37
<212> TYPE: DNA
<213> ORGANISM: Artificial Sequence
<220> FEATURE:
<223> OTHER INFORMATION: MSHR Forward Primer 1

<400> SEQUENCE: 9
tgtaaaacga cggccagtrg tgcctggagg tgtccat                          37

<210> SEQ ID NO 10
<211> LENGTH: 24
<212> TYPE: DNA
<213> ORGANISM: Artificial Sequence
<220> FEATURE:
<223> OTHER INFORMATION: MSHR Forward Primer 5

<400> SEQUENCE: 10
cgcccagatg gccgcgatgg accg                                        24

<210> SEQ ID NO 11
```

```
<211> LENGTH: 27
<212> TYPE: DNA
<213> ORGANISM: Artificial Sequence
<220> FEATURE:
<223> OTHER INFORMATION: aMSHR Forward Primer 4

<400> SEQUENCE: 11
tgcgctacca cagcatcgtg accctgc                                          27

<210> SEQ ID NO 12
<211> LENGTH: 24
<212> TYPE: DNA
<213> ORGANISM: Artificial Sequence
<220> FEATURE:
<223> OTHER INFORMATION: aMSHR Reverse Primer 4

<400> SEQUENCE: 12
gtagtaggcg atgaagagcg tgct                                             24

<210> SEQ ID NO 13
<211> LENGTH: 22
<212> TYPE: DNA
<213> ORGANISM: Artificial Sequence
<220> FEATURE:
<223> OTHER INFORMATION: Forward Primer

<400> SEQUENCE: 13
ctgcctggcc gtgtcggacc tg                                               22

<210> SEQ ID NO 14
<211> LENGTH: 24
<212> TYPE: DNA
<213> ORGANISM: Artificial Sequence
<220> FEATURE:
<223> OTHER INFORMATION: Reverse Primer

<400> SEQUENCE: 14
ctgtggtagc gcagcgcgta gaag                                             24

<210> SEQ ID NO 15
<211> LENGTH: 20
<212> TYPE: DNA
<213> ORGANISM: Artificial Sequence
<220> FEATURE:
<223> OTHER INFORMATION: Example 7 Primer

<400> SEQUENCE: 15
tgaggtagga gagttttggg                                                  20

<210> SEQ ID NO 16
<211> LENGTH: 20
<212> TYPE: DNA
<213> ORGANISM: Artificial Sequence
<220> FEATURE:
<223> OTHER INFORMATION: Example 7 Primer

<400> SEQUENCE: 16
tcgaaattga ggggaagacc                                                  20

<210> SEQ ID NO 17
<211> LENGTH: 25
<212> TYPE: DNA
<213> ORGANISM: Artificial Sequence
<220> FEATURE:
<223> OTHER INFORMATION: KIT1F Primer

<400> SEQUENCE: 17
```

```
tcrtacatag aaagagaygt gactc                                          25

<210> SEQ ID NO 18
<211> LENGTH: 23
<212> TYPE: DNA
<213> ORGANISM: Artificial Sequence
<220> FEATURE:
<223> OTHER INFORMATION: KIT7R Primer

<400> SEQUENCE: 18
agccttcctt gatcatcttg tag                                            23

<210> SEQ ID NO 19
<211> LENGTH: 22
<212> TYPE: DNA
<213> ORGANISM: Artificial Sequence
<220> FEATURE:
<223> OTHER INFORMATION: KIT21 Primer

<400> SEQUENCE: 19
gtattcacag agacttggcg gc                                             22

<210> SEQ ID NO 20
<211> LENGTH: 26
<212> TYPE: DNA
<213> ORGANISM: Artificial Sequence
<220> FEATURE:
<223> OTHER INFORMATION: KIT35 Primer

<400> SEQUENCE: 20
aaacctgcaa ggaaaatcct tcacgg                                         26

<210> SEQ ID NO 21
<211> LENGTH: 25
<212> TYPE: DNA
<213> ORGANISM: Artificial Sequence
<220> FEATURE:
<223> OTHER INFORMATION: Example 12 KIT Forward Primer

<400> SEQUENCE: 21
gaatattgtt gctatggtga tctcc                                          25

<210> SEQ ID NO 22
<211> LENGTH: 22
<212> TYPE: DNA
<213> ORGANISM: Artificial Sequence
<220> FEATURE:
<223> OTHER INFORMATION: Example 12 KIT reverse primer

<400> SEQUENCE: 22
ccgcttctgc gtgatcttcc tg                                             22

<210> SEQ ID NO 23
<211> LENGTH: 22
<212> TYPE: DNA
<213> ORGANISM: Artificial Sequence
<220> FEATURE:
<223> OTHER INFORMATION: Example 12 CRC Forward Primer

<400> SEQUENCE: 23
ctggatgtcc tgtgttccct gt                                             22

<210> SEQ ID NO 24
<211> LENGTH: 23
<212> TYPE: DNA
```

<213> ORGANISM: Artificial Sequence
<220> FEATURE:
<223> OTHER INFORMATION: Example 12 CRC Reverse Primer

<400> SEQUENCE: 24
aggtttgtct gcagcagaag ctc                                    23

<210> SEQ ID NO 25
<211> LENGTH: 26
<212> TYPE: DNA
<213> ORGANISM: Artificial Sequence
<220> FEATURE:
<223> OTHER INFORMATION: Example 14 KITDEL2 Forward Primer

<400> SEQUENCE: 25
gaaagtgayg tctggtccta tsggat                                 26

<210> SEQ ID NO 26
<211> LENGTH: 23
<212> TYPE: DNA
<213> ORGANISM: Artificial Sequence
<220> FEATURE:
<223> OTHER INFORMATION: Example 14 KITDEL2 Reverse Primer

<400> SEQUENCE: 26
agccttcctt gatcatcttg tag                                    23

<210> SEQ ID NO 27
<211> LENGTH: 22
<212> TYPE: DNA
<213> ORGANISM: Artificial Sequence
<220> FEATURE:
<223> OTHER INFORMATION: Example 15 KITDEL1 Forward Primer

<400> SEQUENCE: 27
tgtgggagct cttctcttta gg                                     22

<210> SEQ ID NO 28
<211> LENGTH: 23
<212> TYPE: DNA
<213> ORGANISM: Artificial Sequence
<220> FEATURE:
<223> OTHER INFORMATION: Example 15 KITDEL1 Reverse Primer

<400> SEQUENCE: 28
ccagcaggac aatgggaaca tct                                    23

<210> SEQ ID NO 29
<211> LENGTH: 22
<212> TYPE: DNA
<213> ORGANISM: Artificial Sequence
<220> FEATURE:
<223> OTHER INFORMATION: KIT40 Primer

<400> SEQUENCE: 29
ggctctgggg gctcggcttt gc                                     22

<210> SEQ ID NO 30
<211> LENGTH: 27
<212> TYPE: DNA
<213> ORGANISM: Artificial Sequence
<220> FEATURE:
<223> OTHER INFORMATION: KIT22S Primer

<400> SEQUENCE: 30
tcagacatct tcgtggacaa gcagagg                                27

<210> SEQ ID NO 31
<211> LENGTH: 25
<212> TYPE: DNA
<213> ORGANISM: Artificial Sequence
<220> FEATURE:
<223> OTHER INFORMATION: KIT1F Primer

<400> SEQUENCE: 31
tcrtacatag aaagagaygt gactc                                    25

<210> SEQ ID NO 32
<211> LENGTH: 23
<212> TYPE: DNA
<213> ORGANISM: Artificial Sequence
<220> FEATURE:
<223> OTHER INFORMATION: KIT7R Primer

<400> SEQUENCE: 32
agccttcctt gatcatcttg tag                                      23

<210> SEQ ID NO 33
<211> LENGTH: 24
<212> TYPE: DNA
<213> ORGANISM: Sus sp.

<400> SEQUENCE: 33
aggacaaacg gagagacgcc tgcg                                     24

<210> SEQ ID NO 34
<211> LENGTH: 8
<212> TYPE: PRT
<213> ORGANISM: Sus sp.

<400> SEQUENCE: 34

Arg Thr Asn Gly Glu Thr Pro Ala
 1               5

<210> SEQ ID NO 35
<211> LENGTH: 18
<212> TYPE: DNA
<213> ORGANISM: Sus sp.

<400> SEQUENCE: 35
aatggcgaaa cacccgtg                                            18

<210> SEQ ID NO 36
<211> LENGTH: 6
<212> TYPE: PRT
<213> ORGANISM: Sus sp.

<400> SEQUENCE: 36

Asn Gly Glu Thr Pro Val
 1               5

<210> SEQ ID NO 37
<211> LENGTH: 18
<212> TYPE: DNA
<213> ORGANISM: Sus sp.

<400> SEQUENCE: 37
aagacggaaa cacccgtg                                            18

<210> SEQ ID NO 38

```
<211> LENGTH: 6
<212> TYPE: PRT
<213> ORGANISM: Sus sp.

<400> SEQUENCE: 38

Arg Thr Glu Thr Pro Val
1               5

<210> SEQ ID NO 39
<211> LENGTH: 18
<212> TYPE: DNA
<213> ORGANISM: Sus sp.

<400> SEQUENCE: 39
aatggcgaaa cacccgtg                                                 18

<210> SEQ ID NO 40
<211> LENGTH: 6
<212> TYPE: PRT
<213> ORGANISM: Sus sp.

<400> SEQUENCE: 40

Asn Gly Glu Thr Pro Val
1               5

<210> SEQ ID NO 41
<211> LENGTH: 18
<212> TYPE: DNA
<213> ORGANISM: Sus sp.

<400> SEQUENCE: 41
aatggcgaaa cacccgtg                                                 18

<210> SEQ ID NO 42
<211> LENGTH: 4
<212> TYPE: PRT
<213> ORGANISM: Sus sp.

<400> SEQUENCE: 42

Asn Gly Glu Thr
1

<210> SEQ ID NO 43
<211> LENGTH: 30
<212> TYPE: DNA
<213> ORGANISM: Artificial Sequence
<220> FEATURE:
<223> OTHER INFORMATION: E19FOR Primer

<400> SEQUENCE: 43
gagcagcccc taccccggaa tgccagttga                                    30

<210> SEQ ID NO 44
<211> LENGTH: 40
<212> TYPE: DNA
<213> ORGANISM: Artificial Sequence
<220> FEATURE:
<223> OTHER INFORMATION: E19REV Primer

<400> SEQUENCE: 44
ctttaaaaca gaacataaaa gcggaaacat catgcgaagg                         40

<210> SEQ ID NO 45
<211> LENGTH: 30
<212> TYPE: DNA
```

<210> SEQ ID NO 45
<211> LENGTH: 30
<212> TYPE: DNA
<213> ORGANISM: Artificial Sequence
<220> FEATURE:
<223> OTHER INFORMATION: EPIG10 Primer

<400> SEQUENCE: 45
ggtctagatc accaggagca ctgcagcacc                               30

<210> SEQ ID NO 46
<211> LENGTH: 30
<212> TYPE: DNA
<213> ORGANISM: Artificial Sequence
<220> FEATURE:
<223> OTHER INFORMATION: EPIG16 Primer

<400> SEQUENCE: 46
gggaagcttg accccgaga gcgacgcgcc                                30

<210> SEQ ID NO 47
<211> LENGTH: 162
<212> TYPE: DNA
<213> ORGANISM: Sus sp.

<400> SEQUENCE: 47
cgacgcgccc tccctgctcc ctggcgggac gatgcctgtg cttggcccgg agaggaggct    60
gctggcttcc ctcagctccg cgccccagc cgcccccccc gcctcgggct ggccgccaac   120
cagaccaacc agacgggccc ccagtgcctg gaggtgtcca tt                     162

<210> SEQ ID NO 48
<211> LENGTH: 160
<212> TYPE: DNA
<213> ORGANISM: Sus sp.

<400> SEQUENCE: 48
cgacgcgccc tccctgctcc ctggcgggac gatgcctgtg cttggcccgg agaggaggct    60
gctggcttcc ctcagctccg cgccccacg ccccccccgc tcgggctgg ccgccaacca   120 gaccaaccag acgggccccc agtgcctgga ggtgtccatt                        160

<210> SEQ ID NO 49
<211> LENGTH: 30
<212> TYPE: DNA
<213> ORGANISM: Artificial Sequence
<220> FEATURE:
<223> OTHER INFORMATION: MC1R121A Primer

<400> SEQUENCE: 49
ggactccatg gagccgcaga tgagcacggt                               30

<210> SEQ ID NO 50
<211> LENGTH: 20
<212> TYPE: DNA
<213> ORGANISM: Artificial Sequence
<220> FEATURE:
<223> OTHER INFORMATION: EPIG13 Primer

<400> SEQUENCE: 50
gcaagaccct ccaggaggtg                                          20

<210> SEQ ID NO 51
<211> LENGTH: 20
<212> TYPE: DNA
<213> ORGANISM: Artificial Sequence
<220> FEATURE:
<223> OTHER INFORMATION: EPIG14 Primer

```
<400> SEQUENCE: 51
cactgagccg tagaagagag                                                  20

<210> SEQ ID NO 52
<211> LENGTH: 914
<212> TYPE: DNA
<213> ORGANISM: Sus sp.

<400> SEQUENCE: 52
ctccctgctc cctgctccct ggcgggacga tgcctgtgct tggcccggag aggaggctgc      60
tggcttccct cagctccgcg cccccagccg cccccggcc gccaacgcct cgggctcaga      120
ccaaccagac gggcccccag tgcctggagg tgtccattcc cgacgggctc ttcctcagcc      180
tggggctggt gagcctcgtg gagaacgtgc tggtggtggc cgccatcgcc aagaaccgca      240
acctgcactc gcccatgtac tacttcgtct gctgcctggc cgtgtcggac ctgctggtga      300
gcgtgagcaa cgtgctggag acggccgtgc tgctgctgct ggaggcgggc gccctggccg      360
cccaggccgc cgtggtgcag cagctggaca atgtcatgga cgtgctcatc tgcggctcca      420
tggtgtccag cctctgcttc ctgggcgcca tcgccgtgga ccgctacgtg tccatcttct      480
acgcgctgcg ctaccacagc atcgtgacgc tgccccgcgc ggggcgggct atcgcggcga      540
tctgggcggg cagcgtgctc tccagcaccc tcttcatcgc ctactaccac cacacggccg      600
tcctgctggg cctcgtcagc ttcttcgtgg ccatgctggc gctcatggcg gtactgtacg      660
tccacatgct ggcccgggcc tgccagcacg ccggcacat cgcccggctc cacaagacgc      720
agcaccccac ccgccagggc tgcggcctca agggcgcggc caccctcacc atcctgctgg      780
gcgtcttcct cctctgctgg gcaccttct cctgcacct ctcccgtc gtcctctgcc      840 cccagcaccc cacctgcggc tgcgtcttca agaacgtcaa cctcttctg gccctcgtca      900 tctgcaactc catc                                                       914

<210> SEQ ID NO 53
<211> LENGTH: 914
<212> TYPE: DNA
<213> ORGANISM: Sus sp.

<400> SEQUENCE: 53
ctccctgctc cctgctccct ggcgggacga tgcctgtgct tggcccggag aggaggctgc      60
tggcttccct cagctccgcg cccccagccg cccccggcc gccaacgcct cgggctcaga      120
ccaaccagac gggcccccag tgcctggagg tgtccattcc cgacgggctc ttcctcagcc      180
tggggctggt gagcctcgtg gagaacgtgc tggtggtggc cgccatcgcc aagaaccgca      240
acctgcactc gcccatgtac tacttcgtct gctgcctggc cgtgtcggac ctgctggtga      300
gcgtgagcaa catgctggag acggccgtgc tgccgtgct ggaggcgggc gccctggccg      360
cccaggccgc cgtggtgcag cagctggaca acgtcatgga cgtgctcatc tgcggctcca      420
tggtgtccag cctctgcttc ctgggcgcca tcgccgtgga ccgctacgtg tccatcttct      480
acgcgctgcg ctaccacagc atcgtgacgc tgccccgcgc ggggcgggct atcgcggcga      540
tctgggcggg cagcgtgctc tccagcaccc tcttcatcgc ctactaccac cacacgccg      600 tcctgctggg cctcgtcagc ttcttcgtgg ccatgctggc gctcatggcg gtactgtacg      660
tccacatgct ggcccgggcc tgccagcacg ccggcacat cgcccggctc cacaagacgc      720
agcaccccac ccgccagggc tgcggcctca agggcgcagc caccctcacc atcctgctgg      780
```

```
gcgtcttcct cctctgctgg gcacccttct tcctgcacct ctccctcgtc gtcctctgcc      840
cccagcaccc cacctgcggc tgcgtcttca agaacgtcaa cctctttctg gccctcgtca      900
tctgcaactc catc                                                        914

<210> SEQ ID NO 54
<211> LENGTH: 916
<212> TYPE: DNA
<213> ORGANISM: Sus sp.

<400> SEQUENCE: 54
ctccctgctc cctgctccct ggcgggacga tgcctgtgct tggcccggag aggaggctgc       60
tggcttccct cagctccgcg cccccagccg ccccccccgg ccgccaacgc ctcgggctca      120
gaccaaccag acgggccccc agtgcctgga ggtgtccatt cccgacgggc tcttcctcag      180
cctggggctg gtgagcctcg tggagaacgt gctggtggtg gccgccatcg ccaagaaccg      240
caacctgcac tcgcccatgt actacttcgt ctgctgcctg gccgtgtcgg acctgctggt      300
gagcgtgagc aacgtgctgg agacggccgt gctgctgctg ctggaggcgg cgccctggc       360 cgcccaggcc gccgtggtgc agcagctgga caatgtcatg aacgtgctca tctgcggctc      420
catggtgtcc agcctctgct tcctgggcgc catcgccgtg gaccgctacg tgtccatctt      480
ctacgcgctg cgctaccaca gcatcgtgac gctgccccgc gcggggcggg ctatcgcggc      540
gatctgggcg ggcagcgtgc tctccagcac cctcttcatc gcctactacc accacacggc      600
cgtcctgctg ggcctcgtca gcttcttcgt ggccatgctg gcgctcatgg cggtactgta      660
cgtccacatg ctggcccggg cctgccagca cggccggcac atcgcccggc tccacaagac      720
gcagcacccc acccgccagg gctgcggcct caagggcgcg gccaccctca ccatcctgct      780
gggcgtcttc ctcctctgct gggcacccct cttcctgcac ctctccctcg tcgtcctctg      840 ccccccagcac cccacctgcg gctgcgtctt caagaacgtc aacctctttc tggccctcgt      900
catctgcaac tccatc                                                      916

<210> SEQ ID NO 55
<211> LENGTH: 756
<212> TYPE: DNA
<213> ORGANISM: Sus sp.

<400> SEQUENCE: 55
cccgacgggc tcttcctcag cctggggctg gtgagcctcg tggagaacgt gctggtggtg       60
gccgccatcg ccaagaaccg caacctgcac tcgcccatgt actacttcgt ctgctgcctg      120
gccgtgtcgg acctgctggt gagcgtgagc aacgtgctgg agacggccgt gctgctgctg      180
ctggaggcgg cgccctggc cgcccaggcc gccgtggtgc agcagctgga caatgtcatg      240
aacgtgctca tctgcggctc catggtgtcc agcctctgct tcctgggcgc catcgccgtg      300
gaccgctacg tgtccatctt ctacgcgctg cgctaccaca gcatcgtgac gctgccccgc      360
gcggggcggg ctatcgcggc gatctgggcg ggcagcgtgc tctccagcac cctcttcatc      420
gcctactacc accacacggc cgtcctgctg ggcctcgtca gcttcttcgt ggccatgctg      480
gcgctcatgg cggtactgta cgtccacatg ctggcccggg cctgccagca cggccggcac      540
atcgcccggc tccacaagac gcagcacccc acccgccagg gctgcggcct caagggcgcg      600
gccaccctca ccatcctgct gggcgtcttc ctcctctgct gggcacccct tcctgcac       660 ctctccctcg tcgtcctctg ccccccagcac cccacctgcg gctgcgtctt caagaacgtc      720
aacctctttc tggccctcgt catctgcaac tccatc                                756
```

<210> SEQ ID NO 56
<211> LENGTH: 759
<212> TYPE: DNA
<213> ORGANISM: Sus sp.

<400> SEQUENCE: 56

```
attcccgacg ggctcttcct cagcctgggg ctggtgagcc tcgtggagaa cgtgctggtg     60
gtggccgcca tcgccaagaa ccgcaacctg cactcgccca tgtactactt cgtctgctgc    120
ctggccgtgt cggacctgct ggtgagcgtg agcaacgtgc tggagacggc cgtgctgctg    180
ctgctggagg cgggcgccct ggccgcccag gccgccgtgg tgcagcagct ggacaatgtc    240
atgaacgtgc tcatctgcgg ctccatggtg tccagcctct gcttcctggg cgccatcgcc    300
gtggaccgct acgtgtccat cttctacgcg ctgcgctacc acagcatcgt gacgctgccc    360
cgcgcggggc gggctatcgc ggcgatctgg cgggcagcg tgctctccag caccctcttc    420
atcgcctact accaccacac ggccgtcctg ctgggcctcg tcagcttctt cgtggccatg    480
ctggcgctca tggcggtact gtacgtccac atgctggccc gggcctgcca gcacggccgg    540
cacatcgccc ggctccacaa gacgcagcac cccacccgcc agggctgcgg cctcaagggc    600
gcggccaccc tcaccatcct gctgggcgtc ttcctcctct gctgggcacc cttcttcctg    660
cacctctccc tcgtcgtcct ctgccccag caccccacct gcggctgcgt cttcaagaac    720
gtcaacctct ttctggccct cgtcatctgc aactccatc                           759
```

<210> SEQ ID NO 57
<211> LENGTH: 759
<212> TYPE: DNA
<213> ORGANISM: Sus sp.

<400> SEQUENCE: 57

```
attcccgacg ggctcttcct cagcctgggg ctggtgagcc tcgtggagaa cgtgctggtg     60
gtggccgcca tcgccaagaa ccgcaacctg cactcgccca tgtactactt cgtctgctgc    120
ctggccgtgt cggacctgct ggtgagcgtg agcaacgtgc tggagacggc cgtgctgctg    180
ctgctggagg cgggcgccct ggccgcccag gccgccgtgg tgcagcagct ggacaatgtc    240
atggacgtgc tcatctgcgg ctccatggtg tccagcctct gcttcctggg cgccatcgcc    300
gtggaccgct acgtgtccat cttctacgcg ctgcgctacc acagcatcgt gacgctgccc    360
cgcgtggggc gggctatcgc ggcgatctgg cgggcagcg tgctctccag caccctcttc    420
atcgcctact accaccacac ggccgtcctg ctgggcctcg tcagcttctt cgtggccatg    480
ctggcgctca tggcggtact gtacgtccac atgctggccc gggcctgcca gcacggccgg    540
cacatcgccc ggctccacaa gacgcagcac cccacccgcc agggctgcgg cctcaagggc    600
acggccaccc tcaccatcct gctgggcgtc ttcctcctct gctgggcacc cttcttcctg    660
cacctctccc tcgtcgtcct ctgccccag caccccacct gcggctgcgt cttcaagaac    720
gtcaacctct ttctggccct cgtcatctgc aactccatc                           759
```

<210> SEQ ID NO 58
<211> LENGTH: 253
<212> TYPE: PRT
<213> ORGANISM: Sus sp.
<220> FEATURE:
<221> NAME/KEY: misc_feature
<222> LOCATION: (1)..(1)
<223> OTHER INFORMATION: Xaa can be any naturally occurring amino acid

<400> SEQUENCE: 58

| Xaa | Pro | Asn | Gly | Leu | Phe | Leu | Ser | Leu | Gly | Leu | Val | Ser | Leu | Val | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Asn Val Leu Val Val Ala Ala Ile Ala Lys Asn Arg Asn Leu His Ser
            20                  25                  30

Pro Met Tyr Tyr Phe Val Cys Cys Leu Ala Val Ser Asp Leu Leu Val
            35                  40                  45

Ser Val Ser Asn Val Leu Glu Thr Ala Val Leu Leu Leu Glu Ala
        50                  55                  60

Gly Ala Leu Ala Ala Gln Ala Ala Val Val Gln Gln Leu Asp Asn Val
65                      70                  75                  80

Met Asp Val Leu Ile Cys Gly Ser Met Val Ser Ser Leu Cys Phe Leu
                    85                  90                  95

Gly Ala Ile Ala Val Asp Arg Tyr Val Ser Ile Phe Tyr Ala Leu Arg
                100                 105                 110

Tyr His Ser Ile Val Thr Leu Pro Arg Ala Gly Arg Ala Ile Ala Ala
                115                 120                 125

Ile Trp Ala Gly Ser Val Leu Ser Ser Thr Leu Phe Ile Ala Tyr Tyr
    130                 135                 140

His His Thr Ala Val Leu Leu Gly Leu Val Ser Phe Phe Val Ala Met
145                 150                 155                 160

Leu Ala Leu Met Ala Val Leu Tyr Val His Met Leu Ala Arg Ala Cys
                165                 170                 175

Gln His Gly Arg His Ile Ala Arg Leu His Lys Thr Gln His Pro Thr
            180                 185                 190

Arg Gln Gly Cys Gly Leu Lys Gly Ala Ala Thr Leu Thr Ile Leu Leu
            195                 200                 205

Gly Val Phe Leu Leu Cys Trp Ala Pro Phe Phe Leu His Leu Ser Leu
210                 215                 220

Val Val Leu Cys Pro Gln His Pro Thr Cys Gly Cys Val Phe Lys Asn
225                 230                 235                 240

Val Asn Leu Phe Leu Ala Leu Val Ile Cys Asn Ser Ile
                245                 250

<210> SEQ ID NO 59
<211> LENGTH: 253
<212> TYPE: PRT
<213> ORGANISM: Sus sp.
<220> FEATURE:
<221> NAME/KEY: misc_feature
<222> LOCATION: (1)..(1)
<223> OTHER INFORMATION: Xaa can be any naturally occurring amino acid

<400> SEQUENCE: 59

Xaa Pro Asn Gly Leu Phe Leu Ser Leu Gly Leu Val Ser Leu Val Glu
1               5                   10                  15

Asn Val Leu Val Val Ala Ala Ile Ala Lys Asn Arg Asn Leu His Ser
            20                  25                  30

Pro Met Tyr Tyr Phe Val Cys Cys Leu Ala Val Ser Asp Leu Leu Val
            35                  40                  45

Ser Val Ser Asn Met Leu Glu Thr Ala Val Leu Pro Leu Leu Glu Ala
        50                  55                  60

Gly Ala Leu Ala Ala Gln Ala Ala Val Val Gln Gln Leu Asp Asn Val
65                      70                  75                  80

Met Asp Val Leu Ile Cys Gly Ser Met Val Ser Ser Leu Cys Phe Leu
                    85                  90                  95

```
Gly Ala Ile Ala Val Asp Arg Tyr Val Ser Ile Phe Tyr Ala Leu Arg
            100                 105                 110

Tyr His Ser Ile Val Thr Leu Pro Arg Ala Gly Arg Ala Ile Ala Ala
            115                 120                 125

Ile Trp Ala Gly Ser Val Leu Ser Ser Thr Leu Phe Ile Ala Tyr Tyr
        130                 135                 140

His His Thr Ala Val Leu Leu Gly Leu Val Ser Phe Val Ala Met
145                 150                 155                 160

Leu Ala Leu Met Ala Val Leu Tyr Val His Met Leu Ala Arg Ala Cys
                165                 170                 175

Gln His Gly Arg His Ile Ala Arg Leu His Lys Thr Gln His Pro Thr
            180                 185                 190

Arg Gln Gly Cys Gly Leu Lys Gly Ala Ala Thr Leu Thr Ile Leu Leu
            195                 200                 205

Gly Val Phe Leu Leu Cys Trp Ala Pro Phe Phe Leu His Leu Ser Leu
        210                 215                 220

Val Val Leu Cys Pro Gln His Pro Thr Cys Gly Cys Val Phe Lys Asn
225                 230                 235                 240

Val Asn Leu Phe Leu Ala Leu Val Ile Cys Asn Ser Ile
                245                 250
```

<210> SEQ ID NO 60
<211> LENGTH: 253
<212> TYPE: PRT
<213> ORGANISM: Sus sp.
<220> FEATURE:
<221> NAME/KEY: misc_feature
<222> LOCATION: (1)..(1)
<223> OTHER INFORMATION: Xaa can be any naturally occurring amino acid

<400> SEQUENCE: 60

```
Xaa Pro Asn Gly Leu Phe Leu Ser Leu Gly Leu Val Ser Leu Val Glu
1               5                   10                  15

Asn Val Leu Val Val Ala Ala Ile Ala Lys Asn Arg Asn Leu His Ser
                20                  25                  30

Pro Met Tyr Tyr Phe Val Cys Cys Leu Ala Val Ser Asp Leu Leu Val
            35                  40                  45

Ser Val Ser Asn Val Leu Glu Thr Ala Val Leu Leu Leu Glu Ala
        50                  55                  60

Gly Ala Leu Ala Ala Gln Ala Ala Val Val Gln Gln Leu Asp Asn Val
65                  70                  75                  80

Met Asn Val Leu Ile Cys Gly Ser Met Val Ser Ser Leu Cys Phe Leu
                85                  90                  95

Gly Ala Ile Ala Val Asp Arg Tyr Val Ser Ile Phe Tyr Ala Leu Arg
            100                 105                 110

Tyr His Ser Ile Val Thr Leu Pro Arg Ala Gly Arg Ala Ile Ala Ala
            115                 120                 125

Ile Trp Ala Gly Ser Val Leu Ser Ser Thr Leu Phe Ile Ala Tyr Tyr
        130                 135                 140

His His Thr Ala Val Leu Leu Gly Leu Val Ser Phe Val Ala Met
145                 150                 155                 160

Leu Ala Leu Met Ala Val Leu Tyr Val His Met Leu Ala Arg Ala Cys
                165                 170                 175

Gln His Gly Arg His Ile Ala Arg Leu His Lys Thr Gln His Pro Thr
            180                 185                 190
```

```
Arg Gln Gly Cys Gly Leu Lys Gly Ala Ala Thr Leu Thr Ile Leu Leu
        195                 200                 205

Gly Val Phe Leu Leu Cys Trp Ala Pro Phe Phe Leu His Leu Ser Leu
210                 215                 220

Val Val Leu Cys Pro Gln His Pro Thr Cys Gly Cys Val Phe Lys Asn
225                 230                 235                 240

Val Asn Leu Phe Leu Ala Leu Val Ile Cys Asn Ser Ile
                245                 250
```

<210> SEQ ID NO 61
<211> LENGTH: 253
<212> TYPE: PRT
<213> ORGANISM: Sus sp.
<220> FEATURE:
<221> NAME/KEY: misc_feature
<222> LOCATION: (1)..(1)
<223> OTHER INFORMATION: Xaa can be any naturally occurring amino acid

<400> SEQUENCE: 61

```
Xaa Pro Asn Gly Leu Phe Leu Ser Leu Gly Leu Val Ser Leu Val Glu
1               5                   10                  15

Asn Val Leu Val Val Ala Ala Ile Ala Lys Asn Arg Asn Leu His Ser
            20                  25                  30

Pro Met Tyr Tyr Phe Val Cys Cys Leu Ala Val Ser Asp Leu Leu Val
        35                  40                  45

Ser Val Ser Asn Val Leu Glu Thr Ala Val Leu Leu Leu Glu Ala
    50                  55                  60

Gly Ala Leu Ala Ala Gln Ala Ala Val Val Gln Gln Leu Asp Asn Val
65                  70                  75                  80

Met Asp Val Leu Ile Cys Gly Ser Met Val Ser Ser Leu Cys Phe Leu
                85                  90                  95

Gly Ala Ile Ala Val Asp Arg Tyr Val Ser Ile Phe Tyr Ala Leu Arg
            100                 105                 110

Tyr His Ser Ile Val Thr Leu Pro Arg Val Gly Arg Ala Ile Ala Ala
        115                 120                 125

Ile Trp Ala Gly Ser Val Leu Ser Ser Thr Leu Phe Ile Ala Tyr Tyr
130                 135                 140

His His Thr Ala Val Leu Leu Gly Leu Val Ser Phe Phe Val Ala Met
145                 150                 155                 160

Leu Ala Leu Met Ala Val Leu Tyr Val His Met Leu Ala Arg Ala Cys
                165                 170                 175

Gln His Gly Arg His Ile Ala Arg Leu His Lys Thr Gln His Pro Thr
            180                 185                 190

Arg Gln Gly Cys Gly Leu Lys Gly Thr Ala Thr Leu Thr Ile Leu Leu
        195                 200                 205

Gly Val Phe Leu Leu Cys Trp Ala Pro Phe Phe Leu His Leu Ser Leu
210                 215                 220

Val Val Leu Cys Pro Gln His Pro Thr Cys Gly Cys Val Phe Lys Asn
225                 230                 235                 240

Val Asn Leu Phe Leu Ala Leu Val Ile Cys Asn Ser Ile
                245                 250
```

<210> SEQ ID NO 62
<211> LENGTH: 48
<212> TYPE: DNA
<213> ORGANISM: Sus sp.

<400> SEQUENCE: 62

```
aattacgtgg tcaaaggaaa cgtgagtacc cacgctctcc tgacagtc          48
```

<210> SEQ ID NO 63
<211> LENGTH: 48
<212> TYPE: DNA
<213> ORGANISM: Sus sp.

<400> SEQUENCE: 63

```
aattacgtgg tcaaaggaaa catgagtacc cacgctctcc tgacagtc          48
```

<210> SEQ ID NO 64
<211> LENGTH: 2919
<212> TYPE: DNA
<213> ORGANISM: Sus sp.

<400> SEQUENCE: 64

```
atgagaggcg ctcgccgcgc ctgggatttt ctcttcgtcc tgcagctctt gcttcgcgtc     60
cagacaggct cttctcagcc atctgtgagt ccagaggaac tgtctccacc atccatccat    120
ccagcaaaat cagagttaat cgtcagtgct ggcgatgaga ttaggctgtt ctgcaccgat    180
ccaggatctg tcaaatggac ttttgagacc ctgggtcagc tgagtgagaa tacacacgca    240
gagtggatcg tggagaaagc agaggccatg aatacaggca attatacatg caccaatgaa    300
ggcggtttaa gcagttccat ttatgtgttt gttagagatc ctgagaagct tttcctcgtc    360
gaccctccct tgtatgggaa ggaggacaat gacgcgctgg tccgatgtcc tctgacggac    420
ccagaggtga ccaattactc cctcacgggc tgcgagggga accccttcc caaggatttg     480
accttcgtcg cggaccccaa ggccggcatc accatcagaa acgtgaagcg cgagtatcat    540
cggctctgtc tccactgctc cgccaaccag ggggcaagt ccgtgctgtc gaagaaattc     600
accctgaaag tgagggcagc catcagagct gtacctgttg tggctgtgtc caaagcaagc    660
taccttctca gggaagggga ggaatttgcc gtgatgtgct tgatcaaaga cgtgtctagt    720
tccgtggact ccatgtggat cagggagaac agccagacta agcacaggt gaagaggaat     780
agctggcatc agggtgactt caattttctg cggcaggaaa ggctgacaat cagctcagca    840
agagttaatg attctggcgt gttcatgtgt tacgccaata atacttttgg atctgcaaat    900
gtcacaacca cctagaagt agtagataaa ggattcatta atatcttccc tatgatgaat     960
accactgtgt ttgtaaacga tggagaggat gtggatctaa ttgttgagta cgaggcgtac   1020
cccaaacctg aacaccgaca gtggatatat atgaaccgca ctgccactga taagtgggag   1080
gattatccca gtctgagaa tgaaagtaac atcagatatg taagtgaact tcacttgacc   1140
agattaaaag ggaccgaagg aggcacttac acatttctcg tgtccaatgc tgatgtcaat   1200
tcttctgtga catttaatgt ttacgtgaac acaaaaccag aaatcctgac tcatgacagg   1260
ctcatgaacg gcatgctcca gtgtgtggcg gcaggcttcc cagagcccac catcgattgg   1320
tatttctgtc aggcaccga gcagagatgt tccgttcccg ttgggccagt ggacgtgcag   1380
atccaaaact catctgtatc accgtttgga aaactagtga ttcacagctc cattgattac   1440
agtgcattca acacaacgg cacggtggag tgcagggctt acaacgatgt gggcaagagt   1500
tctgccttt ttaactttgc atttaaagaa caaatccatg cccacaccct cttcacgcct   1560
ttgctgattg gttttgtgat cgcagcgggt atgatgtgta tcatcgtgat gattctcacc   1620
tataaatatc tacagaagcc catgtatgaa gtacagtgga aggttgtcga ggagataaat   1680
ggaaacaatt atgtctacat agacccaacg caacttcctt atgatcacaa atgggaattt   1740
```

```
cccaggaaca ggctgagttt tggcaaaacc ttgggtgctg gcgccttcgg gaaagtcgtt    1800
gaggccactg catacggctt aattaagtca gatgcggcca tgaccgttgc cgtgaagatg    1860
ctcaaaccaa gtgcccattt aacgaacga gaagccctaa tgtctgaact caaagtctta    1920
agttacctcg gtaatcacat gaatattgtg aatcttctcg gcgcctgcac cattggaggg    1980 cccacccctgg tcattacaga atattgttgc tatggtgatc tcctgaattt tttgagacgg    2040
aaacgtgatt cgtttatttg ctcaaagcag gaagatcacg cagaagcggc gctttataag    2100
aaccttctgc attcaaagga gtcttcctgc agtgacagta ctaacgagta catggacatg    2160
aaacccggag tgtcttatgt ggtaccaacc aaggcagaca aaggagatc tgcgagaata    2220 ggctcataca tagaacgaga tgtgactcct gccatcatgg aagatgatga gttggcccta    2280
gacctggagg acttgctcag cttttcttac caagtggcaa agggcatggc cttcctcgcc    2340
tcgaagaatt gtattcacag agacttggcg gccagaaata tcctccttac tcatggtcga    2400
atcacaaaga tttgtgattt tggtctagcc agagacatca gaatgattc taattacgtg    2460 gtcaaaggaa acgctcggct acccgtgaag tggatggcac ctgagagcat tttcaactgt    2520
gtctacacat ttgaaagcga tgtctggtcc tatgggattt ttctgtggga gctcttctct    2580
ttagggagca gccctaccc cggaatgcca gttgattcta aattctacaa gatgatcaag    2640 gagggttttcc gaatgctcag ccctgagcat gcacctgcgg aaatgtatga catcatgaag    2700
acttgctggg atgcggatcc cctcaaaaga ccaacgttta gcagatcgt gcagctgatt    2760 gagaagcaga tttcggagag caccaatcac atttattcca acttagcgaa ctgcagcccc    2820
caccgggaga accccgcggt ggatcattct gtgcggatca actccgtggg cagcagtgcc    2880
tcctccacgc agcctctgct tgtccacgaa gatgtctga                           2919

<210> SEQ ID NO 65
<211> LENGTH: 434
<212> TYPE: DNA
<213> ORGANISM: Sus sp.

<400> SEQUENCE: 65
ctgcagtgct cctggtgagg ggggacgggc gctggagcca ggctgcgggg ctgagggcag     60
tggtgccgtc ctgcggcccg gttcctacgt ggctgggcag ccccttggca gagaggacgg    120
gccggacatc tctgaaggta tggacgctgg accctctggg gcccgacaga ggaagagcca    180
gcacttccag gaggcatggg gagtggggga ggctggagag acggcgggga gcgccacctc    240
catccagaga ccaccacgcc cgcctttggg gcgcgctctg gggactttgc ccccactgg    300 ggtgggacgt gtgcgggcag aagctgtccg ggtgttgctc actgcaggac ctcaggggaa    360
ggccttcgtg actgctagga agcaggcgca gcgccccggc ggagggcggg gcccctctct    420
tctacggctc agtg                                                      434

<210> SEQ ID NO 66
<211> LENGTH: 433
<212> TYPE: DNA
<213> ORGANISM: Sus sp.

<400> SEQUENCE: 66
ctgcagtgct cctggtgagg gggcgggcg ctggagccag gctgcgggc tgagggcagt      60 ggtgccgtcc tgcggcccgg ttcctacgtg gctgggcagc cccttggcag agaggacggg   120
ccggacatct ctgaaggtat ggacgctgga ccctctgggg cccgacagag gaagagccgg   180
cacttccagg aggcatgggg agtgggggag gctggagaga cggcggggag cgccacctcc   240
```

-continued

```
atccagagac caccacgccc gcctttgggg cgcgctctgg ggactttgcc ccccactggg      300
gtgggacgtg tgcgggcaga agctgtccgg gtgttgctca ctgcaggacc tcaggggaag      360
gccttcgtga ctgctaggaa gcaggcgcag cgccccggcg gagggcgggg ccccctctctt    420 ctacggctca gtg                                                         433
```

<210> SEQ ID NO 67
<211> LENGTH: 434
<212> TYPE: DNA
<213> ORGANISM: Sus sp.

<400> SEQUENCE: 67

```
ctgcagtgct cctggtgagg ggggacgggc gctggagcca ggctgcgggg ctgagggcag       60
tggtgccgtc ctgcggcccg gttcctacgt ggctgggcag ccccttggca gagaggacgg     120
gccggacatc tctgaaggta tggacgctgg accctctggg gcccgacaga ggaagagccg    180
gcacttccag gaggcatggg gagtggggga ggctggagag acggcgggga gcgccacctc    240
catccagaga ccaccacgcc cgcctttggg gcgcgctctg gggactttgc ccccactgg     300 ggtgggacgt gtgcgggcag aagctgtccg ggtgttgctc actgcaggac ctcagggaa     360 ggccttcgtg actgctagga agcaggcgca gcgccccggc ggagggcggg gcccctctct    420
tctacggctc agtg                                                       434
```

<210> SEQ ID NO 68
<211> LENGTH: 23
<212> TYPE: DNA
<213> ORGANISM: Artificial Sequence
<220> FEATURE:
<223> OTHER INFORMATION: E19PC Probe

<400> SEQUENCE: 68

```
catacatttc cgcaggtgca tgc                                              23
```

<210> SEQ ID NO 69
<211> LENGTH: 24
<212> TYPE: DNA
<213> ORGANISM: Artificial Sequence
<220> FEATURE:
<223> OTHER INFORMATION: E19PT Probe

<400> SEQUENCE: 69

```
tcatacattt ccacaggtgc atgc                                             24
```